US007449321B2

(12) United States Patent
Ng et al.

(10) Patent No.: US 7,449,321 B2
(45) Date of Patent: Nov. 11, 2008

(54) MOLECULES, COMPOSITIONS, METHODS AND KITS FOR APPLICATIONS ASSOCIATED WITH FLAVIVIRUSES

(75) Inventors: Mary Mah Lee Ng, Singapore (SG); Justin Jan Hann Chu, Singapore (SG)

(73) Assignee: National University of Singapore, Singapore (SG)

( * ) Notice: Subject to any disclaimer, the term of this patent is extended or adjusted under 35 U.S.C. 154(b) by 164 days.

(21) Appl. No.: 10/769,565

(22) Filed: Jan. 29, 2004

(65) Prior Publication Data

US 2004/0242483 A1 Dec. 2, 2004

Related U.S. Application Data

(63) Continuation-in-part of application No. 10/763,450, filed on Jan. 22, 2004, now abandoned.

(60) Provisional application No. 60/442,157, filed on Jan. 22, 2003.

(51) Int. Cl.
 *C12N 7/00* (2006.01)
(52) U.S. Cl. .................................................. 435/235.1
(58) Field of Classification Search .............. 424/186.1, 424/218.1, 199.1, 320.1, 185.1, 159.1
 See application file for complete search history.

(56) References Cited

U.S. PATENT DOCUMENTS 4,376,110 A 3/1983 David et al.

OTHER PUBLICATIONS

Wu et al., "Neutralizing peptide ligands selected from phage-displayed libraries mimic the conformational epitope on domain III of the Japanese encephalitis virus envelope protein," Virus Research, 76, pp. 59-69 (2001).*
Result 2, 20.rge.*
Result 2, 21.rup.*
Result 2, 20.rge, (Jun. 12, 2006).*
Result 2, 21.rup, (Jun. 10, 2006).*
Bhardwaj et al (Journal of Virology 75:4002-4007, 2001).*
Chu et al (Journal of General Virology 86:405-412, 2005).*
Adlish et al.; Identification of a putative cell receptor for human cytomegalovirus; Virology; 1990; vol. 176; pp. 337-345.
Agnello et al.; Hepatitis C virus and other Flaviviridae viruses enter cells via low density lipoprotein receptor, Proc Natl Acad Sci; Oct. 26, 1996; vol. 96, No. 22; pp. 12766-12771.
Atkinson et al.; Purification and properties of HeLa cell plasma membranes; J Biol Chem; Aug. 25, 1971; vol. 246, No. 16; pp. 5162-5175.
Beasley et al.; Identification of neutralizing epitopes within structural domain III of the West Nile virus envelop protein; J. Virol.; Dec. 2002; vol. 76, No. 24; pp. 13097-13100.
Bielefeldt-Ohmann et al.; Dengue virus binding to human leukocyte cell lines: receptor usage differs between cell types and virus strains; Virus Res.; 2001; vol. 73; pp. 81-89.
Blau et al.; Entry and release of measles virus are polarized in epithelial cells; Virology; 1995; vol. 210; pp. 91-99.
Borrow et al.; Characterization of lymphocytic choriomeningitis virus-binding protein(s): a candidate cellular receptor for the virus; J Virol.; Dec. 1992; vol. 66, No. 12; pp. 7270-7281.
Bruett et al.; Characterization of a membrane-associated protein implicated in visna virus binding and infection; Virology; 2000; vol. 271; pp. 132-141.
Cao et al.; Identification of α-Dystroglycan as a receptor for lymphocytic choriomeningitis virus and Lassa fever virus; Science; Dec. 11, 1998; vol. 282; pp. 2079-2081.
Castle et al.; Primary structure of the West Nile flavivirus genome region coding for all nonstructural proteins. Virology; 1986; vol. 149; pp. 10-26.
Castle et al.; Sequence analysis of the viral core protein and the membrane-associated proteins VI and NV2 of the flavivirus West Nile virus and of the genome sequence for these proteins; Virology; 1985; vol. 145; pp. 227-236.
Chen et al.; Dengue virus infectivity depends on envelope protein binding to target cell heparan sulfate; Nat Med; Aug. 1997; vol. 139, No. 8; pp. 239-251.
Choi et al.; Reovirus binds to multiple plasma membrane proteins of mouse L fibroblasts; Virology; 1990; vol. 178; pp. 316-320.
Chu et al.; Infection of polarized epithelial cells with flavivirus West Nile: Polarized entry and egress of virus occur through apical surface; J Gen Virol.; 2002; vol. 83; pp. 2427-2435.
Chu et al.; Trafficking mechanism of West Nile (Sarafend) virus structural proteins; J Med Virol.; 2002; vol. 67; pp. 127-1 36.
Cote et al.; Generation of human monoclonal antibodies reactive with cellular antigens; Proc. Natl. Acad. Sci. USA; Apr. 1983; vol. 80; pp. 2026-2030.
Crane et al.; Identification of cell membrane proteins that bind visna virus; J Virol.; Nov. 1991; vol. 65, No. 11; pp. 6137-6143.
Crill et al.; Monoclonal antibodies that bind to domain III of dengue virus E glycoprotein are the most efficient blockers of virus adsorption to Vero cells; J Virol.; Aug. 2001; vol. 75, No. 16; pp. 7769-7773.
Hasegawa et al.; Mutations in the envelope protein of Japanese encephalitis virus affect entry into cultured cells and virulence in mice; Virology; 1992; vol. 191; pp. 158-165.
Helenius; Alphavirus and flavivirus glycoproteins: structures and functions; Cell; Jun. 2, 1995; vol. 81, pp. 651-653.
Kimura et al.; Analysis of virus-cell binding characteristics on the determination of Japanese encephalitis virus susceptibility; Arch Virol; 1994; vol. 139; pp. 239-251.
Lee et al.; Substitutions at the Putative Receptor-Binding Site of an Encephalitic Flavivirus Alter Virulence and Host Cell Tropism and Reveal for Glycosaminoglycans in Entry; J. of Virology; Oct. 2000; vol. 74, No. 19; pp. 8867-8875.
Martinez-Barragán et al.; Identification of a putative coreceptor on Vero cells that participates in dengue 4 virus infection; J Virol.; Sep. 2001; vol. 75, No. 17; pp. 7818-7827.
Ng et al.; Possible involvement of receptors in the entry of Kunjin virus into Vero cells; Arch Virol.; 1988; vol. 100; pp. 199-211.
Ng et al.; Transport and budding at two distinct sites of visible nucleocpasids of West Nile (Sarafend) virus; J Med Virol.; 2001; vol. 65; pp. 758-764.

(Continued)

*Primary Examiner*—Mary E Mosher
(74) *Attorney, Agent, or Firm*—Seed IP Law Group PLLC

(57) ABSTRACT

A method for controlling a flavivirus entry into a cell, kits for assaying the flavivirus entry into the cell, and methods of treating and preventing flaviviruses infections are disclosed, together with vaccine and pharmaceutical compositions.

13 Claims, 16 Drawing Sheets

OTHER PUBLICATIONS

Putnak et al.; A putative cellular receptor for dengue viruses; Nat Med.; Aug. 1997; vol. 3, No. 8; pp. 828-829.

Rappole et al.; Migratory birds and spread of West Nile virus in the Western Hemisphere; Emerg Infect Dis; Jul.-Aug. 2000; vol. 6, No. 4; pp. 319-328.

Sagara et al.; 71-kilodalton heat shock cognate protein acts as a cellular receptor for syncytium formation induced by human Tcell lymphotropic virus type 1; J Virol; Jan. 1998; vol. 72, No. 1; pp. 535-541.

Salas-Benito et al.; Identification of two surface proteins from C6/36 cells that bind dengue type 4 virus; J Virol; Oct. 1997; vol. 71, No. 10; pp. 7246-7252.

Schneider-Schaulies; Cellular receptors for viruses: links to tropism and pathogenesis; J Gen Virol.; 2000; vol. 81, pp. 1413-1429.

Se-Thoe et al.; Alteration of virus entry mode: a neutralization mechanism for Dengue-2 virus; J Med Virol; 2000; vol. 62, pp. 364-376.

Taylor et al.; The human cytomegalovirus receptor on fibroblasts is a 30-kilodalton membrane protein; J Virol; Jun. 1990; vol. 64, No. 6; pp. 2484-2490.

Thullier et al.; Mapping of a dengue virus neutralizing epitope critical for the infectivity of all serotypes: insight into the neutralization mechanism; J Gen Virol; 2001; vol. 82, pp. 1885-1892.

Verdin et al.; Characterization of a common high-affinity receptor for reovirus serotypes 1 and 3 on endothelial cells; J Virol; Mar. 1989; vol. 63, No. 3; pp. 1318-1 325.

Castle et al; Nucleotide sequence of the 5'-terminal untranslated part of the genome of the flavivirus West Nile virus; Arch Virol; vol. 92; 1987; pp. 309-313.

Cole et al; The EBV-Hybridoma Technique and Its Application to Human Lung Cancer; Monoclonal Antibodies And Cancer Therapy; Alen R. Liss, Inc.; 1985; pp. 77-96.

Cote et al; Generation of human monoclonal antibodies reactive with cellular antigens; Proc. Natl Acad. Sci. USA; vol. 80; Apr. 1983; pp. 2026-2030.

De Madrid et al; The flaviviruses (group B arboviruses): a cross-neutralization study; J Gen Virol; vol. 23; 1974; pp. 91-96.

George et al; Isolation of West Nile virus from the brains of children who had died of encephalitis; Bull World Health Organ; vol. 62, No. 6; 1984; pp. 879-882.

Gollins et al; Flavivirus infection enhancement in macrophages: an electron microscopic study of viral cellular entry; J Gen Virol; vol. 66; 1985; pp. 1969-I 982.

Hase et al; A comparative study of entry modes in C 6/36 cells by Semliki Forest and Japanese encephalitis viruses; Archives of Virology; vol. 108; 1989; pp. 101-114.

Hase et al; Entry and replication of Japanese encephalitis virus in cultured neurogenic cells; J Virol Methods; vol. 30; 1990; pp. 205-214.

Hase et al; Flavivirus entry into cultured mosquito cells and human peripheral blood monocytes; Arch Virol; vol. 104; 1989; pp. 129-143.

Hase et al; Morphogenesis of flaviviruses; Subcell Biochem; vol. 15; 1989; pp. 275-305.

Heinz et al; The interactions of the flavivirus envelope proteins: implications for virus entry and release; Arch Virol Suppl; vol. 9, Suppl; 1994; pp. 339-348.

Köhler et al; Continuous cultures of fused cells secreting antibody of predefined specificity; Nature; vol. 256; Aug. 7, 1975; pp. 495-497.

Kopecky et al; A putative host cell receptor for tick-borne encephalitis virus identified by anti-idiotypic antibodies and virus affinoblotting; Intervirology; vol. 42; 1999; pp. 9-16.

Kozbor et al; The production of monoclonal antibodies from human lymphocytes; Immunology Today; 1983; vol. 4, No. 3; pp. 72-79.

Ramos-Castaneda et al; A 65-kDa trypsin-sensible membrane cell protein as a possible receptor for dengue virus in cultured neuroblastoma cells; J Neurovirol; vol. 3; 1997; pp. 435-440.

Rey et al; THe envelope glycoprotein from tick-borne encephalitis virus at 2 Å resolution; Nature; vol. 375; May 25, 1995; pp. 291-298.

Rice; *Flaviviridae*: the viruses and their replication; Fields Virology, Third Edition; Fields, et al editorsI; Lippincott-Raven; Philadelphia, PA.; Chapter 30; pp. 931-959.

Shi et al; Actions of neurotensin:a review of the electrophysiological studies; Ann NY Acad. Sci.; vol. 668; 1992; 1129-145.

Tokuyasu; Immuno-cryoultramicrotomy; Immunolabelling for Electron Microscopy; Polak et al. editors; Amsterdam; Elsevier Science; Chapter 6; pp. 71-82.

Wengler et al; Sequence analysis of the membrane protein V3 of the flavivirus West Nile virus and of its gene; Virology; vol. 147; 1985; pp. 264-274.

Wengler et al; Studies on virus-specific nucleic acids synthesized in vertebrate and mosquito cells infected with flaviviruses; Virology; vol. 89; 1978; pp. 423-437.

Berditchevski et al.; "Generation of Monoclonal Antibodies to integrin-associated Proteins;" J. Biol. Chem.; vol. 272, No. 46; Nov. 14, 1997; pp. 29174-29180.

Berthet et al.; "Role of Endoproteolytic Processing in the Adhesive and Signaling Functions of $\alpha_v\beta_5$ Intergrin;" J. Biol. Chem.; vol. 275, No. 43; Oct. 27, 2000; pp. 33308-33313.

Borges et al.; "Platelet-derived Growth Factor Receptor β and Vascular Endothelial Growth Factor Receptor 2 Bind to the $\beta_3$ Intergrin through Its Extracellular Domain;" J. Biol. Chem.; vol. 275, No. 51; Dec. 22, 2000; pp. 39867-39873.

Chu et al.; "Characterization of a 105-kDa plasma membrane associated gylycoprotein that is involved in West Nile virus binding and infection;" Virology; vol. 312; 2003; pp. 458-469.

Eigenthaler et al.; "A Conserved Sequence Motif in the Integrin $\beta_3$ Cytoplasmic Domain Is Required for Its Specific Interaction with $\beta_3$-Endonexin;" J. Biol. Chem.; vol. 272, No. 12; Mar. 21, 1997; pp. 7693-7698.

Humphries; "Integrin Structure;" Biochemical Society Transactions; vol. 28, Part 4; 2000; pp. 311-339.

Hynes; "Cell adhesion: old and new questions;" TCB; vol. 9, No. 12; pp. 0962-8924.

Jenkins et al.; "Tyrosine Phosphorylation of the $\beta_3$ Cytoplasmic Domain Mediates Integrin-Cytoskeletal Interactions;" J. Biol. Chem; vol. 273, No. 22; May 29, 1998; pp. 13878-13885.

Le Naour et al.; "Severely Reduced Female Fertility in CD9-Deficient Mice;" Science; vol. 287; Jan. 14, 2000; pp. 319-321.

Lin et al.; "Integrin-mediated Activation of MAP Kinase Is Independent of FAK: Evidence for Dual Integrin Signaling Pathways in Fibroblast;" J. Cell Biol.; vol. 136, No. 6; Mar. 24, 1997; pp. 1385-1395.

Liu et al.; "Integrin cytoplasmic domain-binding proteins;" J. Cell Sci.; vol. 113; 2000; pp. 3563-3571.

Poter et al.; "Integrin take partners: cross-talk between integrins and other membranes recepters;" Cell Biol.; vol. 8; Oct. 1998; pp. 390-396.

Renshaw et al.; "Growth factor activation of MAP kinase requires cell adhesion;" EMBO J.; vol. 16, No. 18; 1997; pp. 5592-5599.

Roovers et al.; "Integrating the MAP kinase signal into the GI phase cell cycle machinery;" BioEssays; vol. 22, No. 9; 2000; pp. 818-826.

Schneller et al.; "$\alpha_v\beta_3$ Integrin associates with activated insulin and PDGFβ receptors and potentiates the biological activity of PDGF;" vol. 16, No. 18; 1997; pp. 5600-5607.

Schwartz et al.; "Interactions between mitogenic stimuli, or, a thousand and one connections;" Curr. Opin. Cell Biol.; vol. 11; 1999; pp. 197-202.

Skinner et al.; "$\beta_1$ Integrin Binds the 16-kDa Subunit of Vacuolar $H^+$-ATPase at a Site Important for Human Papillomavirus E5 and Platelet-derived Growth Factor Signaling;" J. Biol. Chem.; vol. 274, No. 33; Aug. 13, 1999; pp. 23119-23127.

Timpl; "Macromolecular organization of basement membranes;" Curr. Opin. Cell Biol.; vol. 8; 1996; pp. 618-624.

Vallar et al.; "Divalent Cations Differentially Regulate Integrin $\alpha_{nb}$ Cytoplasmic Tail Binding $\beta_3$ and to Calcium- and Integrin-binding Protein;" J. Biol. Chem; vol. 274, No. 24; Jun. 11, 199; pp. 17257-17266.

Varner et al.; "Integrins and cancer;" Curr. Opin. Cell Biol.; vol. 8; 1996; pp. 724-730.

\* cited by examiner

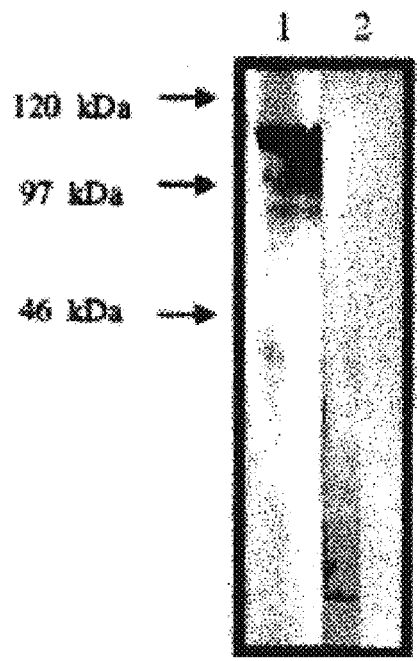 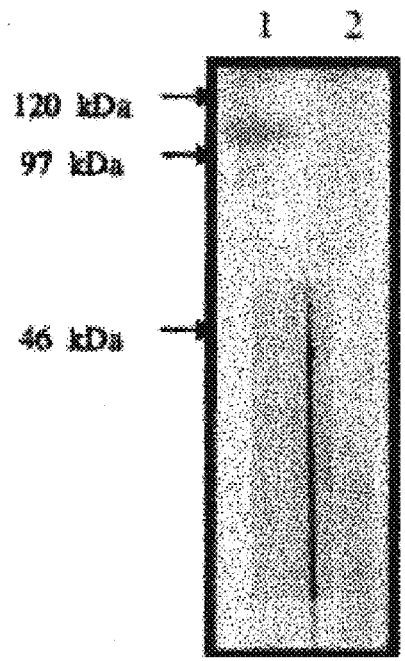
FIG. 2A  FIG. 2B
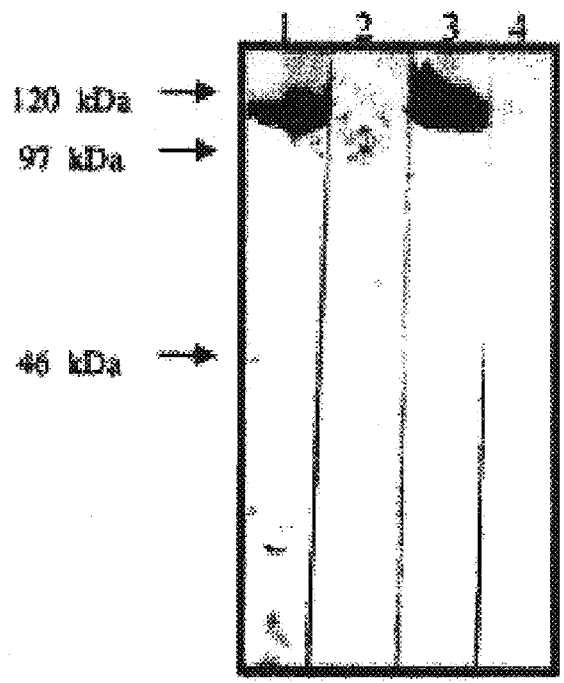
FIG. 3

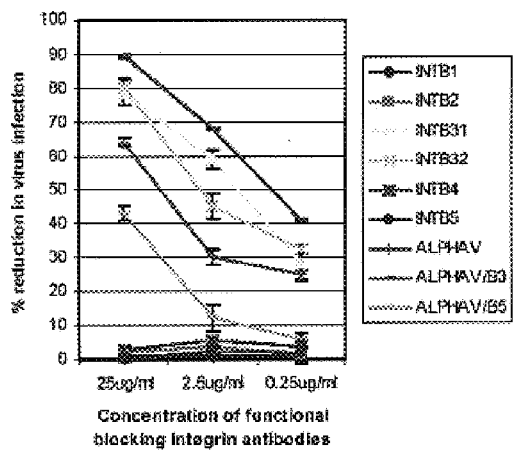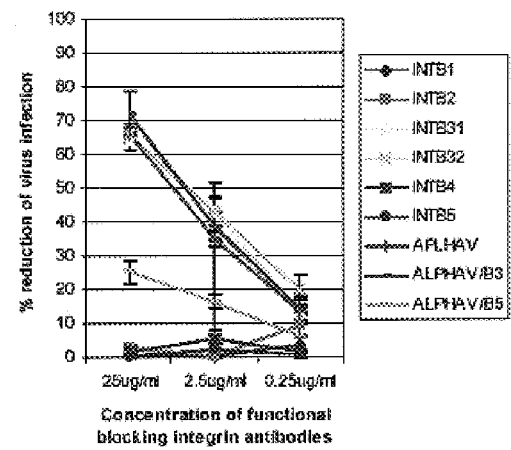
FIG. 11A  FIG. 11B
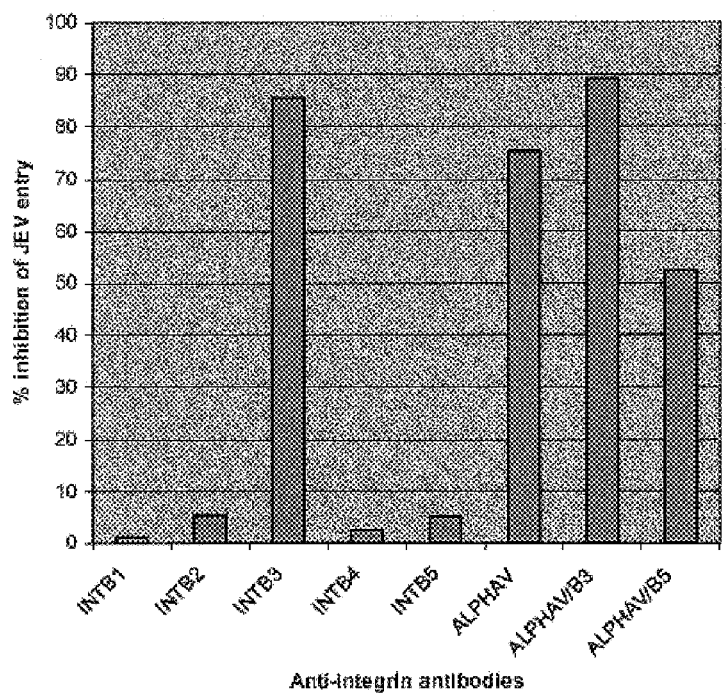
FIG. 12

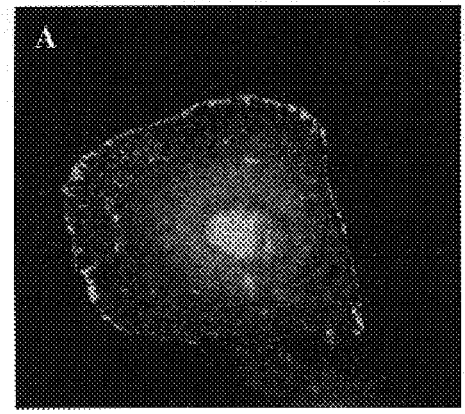
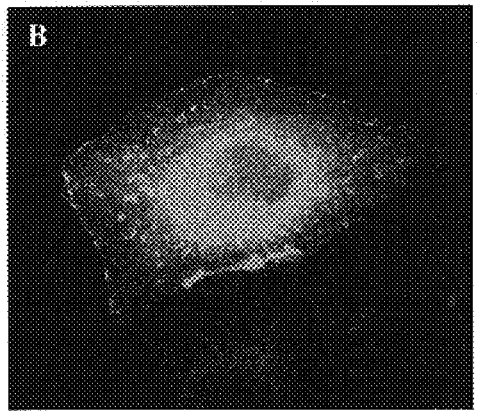
FIG. 15A    FIG. 15B
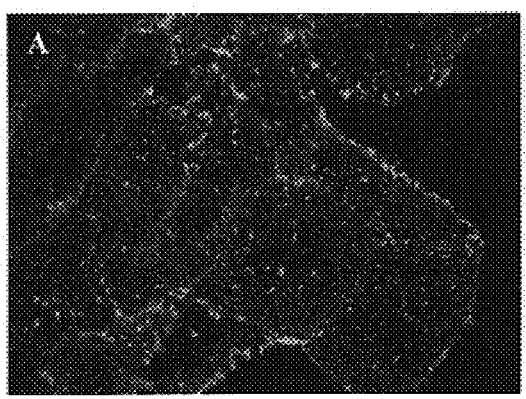
FIG. 16A    FIG. 16B
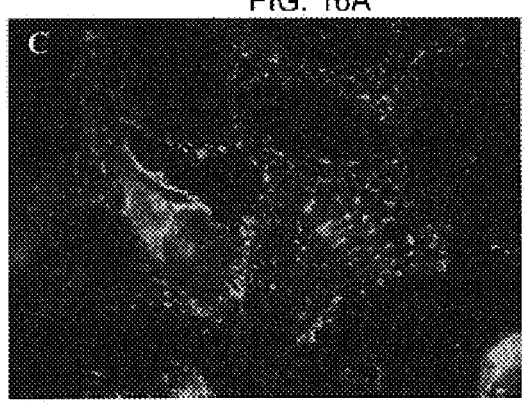
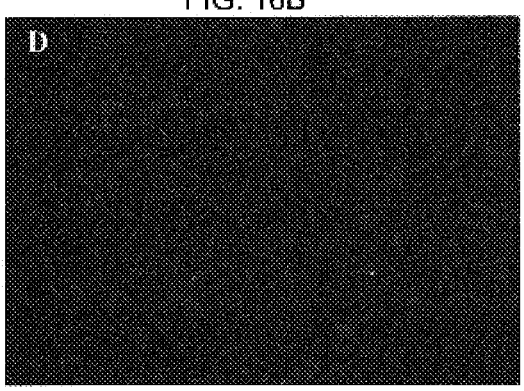
FIG. 16C    FIG. 16D

WNV

FIG. 20

SEQUENCE LISTING

```
<160> NUMBER OF SEQ ID NOS: 21

<210> SEQ ID NO 1
<211> LENGTH: 14
<212> TYPE: PRT
<213> ORGANISM: Vero cells
<220> FEATURE:
```

```
<221> NAME/KEY: misc_feature
<222> LOCATION: (10)..(10)
<223> OTHER INFORMATION: Xaa can be any naturally occurring amino acid

<400> SEQUENCE: 1

Asp Thr Pro Lys Leu Glu Ile Ala Gly Xaa Phe Lys Asp Leu
1               5                   10

<210> SEQ ID NO 2
<211> LENGTH: 14
<212> TYPE: PRT
<213> ORGANISM: Vero cells
<220> FEATURE:
<221> NAME/KEY: misc_feature
<222> LOCATION: (10)..(10)
<223> OTHER INFORMATION: Xaa can be any naturally occurring amino acid

<400> SEQUENCE: 2

Ser Ile Pro Lys Leu Glu Ile Ala Gly Xaa Phe Lys Asp Leu
1               5                   10

<210> SEQ ID NO 3
<211> LENGTH: 20
<212> TYPE: PRT
<213> ORGANISM: Vero cells

<400> SEQUENCE: 3

Met Tyr Ile Ser Pro Leu Glu Ala Leu Glu Gly Asn Pro Cys Tyr Asp
1               5                   10                  15

Met Lys Thr Cys
            20

<210> SEQ ID NO 4
<211> LENGTH: 20
<212> TYPE: PRT
<213> ORGANISM: Vero cells

<400> SEQUENCE: 4

Val Val Ser Asp Asn His Tyr Ser Ala Ser Thr Thr Met Asp Tyr Pro
1               5                   10                  15

Leu Leu Gly Leu
            20

<210> SEQ ID NO 5
<211> LENGTH: 20
<212> TYPE: PRT
<213> ORGANISM: Vero cells

<400> SEQUENCE: 5

Gln Gly Gln Leu Ile Ser Asp Gln Val Ala Glu Ile Ile Ser Lys Tyr
1               5                   10                  15

Asp Pro Asn Val
            20

<210> SEQ ID NO 6
<211> LENGTH: 4
<212> TYPE: PRT
<213> ORGANISM: Synthetic peptide

<400> SEQUENCE: 6

Arg Phe Asp Ser
1

<210> SEQ ID NO 7
```

-continued

```
<211> LENGTH: 5
<212> TYPE: PRT
<213> ORGANISM: Synthetic peptide

<400> SEQUENCE: 7

Gly Arg Gly Asp Ser
1               5

<210> SEQ ID NO 8
<211> LENGTH: 3147
<212> TYPE: DNA
<213> ORGANISM: Homo Sapiens
<220> FEATURE:
<221> NAME/KEY: CDS
<222> LOCATION: (1)..(3144)
<223> OTHER INFORMATION: Sequence coding for integrin alpha V subunit

<400> SEQUENCE: 8 atg gct ttt ccg ccg cgg cga cgg ctg cgc ctc ggt ccc cgc ggc ctc       48
Met Ala Phe Pro Pro Arg Arg Arg Leu Arg Leu Gly Pro Arg Gly Leu
1               5                   10                  15 ccg ctt ctt ctc tcg gga ctc ctg cta cct ctg tgc cgc gcc ttc aac       96
Pro Leu Leu Leu Ser Gly Leu Leu Leu Pro Leu Cys Arg Ala Phe Asn
            20                  25                  30 cta gac gtg gac agt cct gcc gag tac tct ggc ccc gag gga agt tac      144
Leu Asp Val Asp Ser Pro Ala Glu Tyr Ser Gly Pro Glu Gly Ser Tyr
        35                  40                  45 ttc ggc ttc gcc gtg gat ttc ttc gtg ccc agc gcg tct tcc cgg atg      192
Phe Gly Phe Ala Val Asp Phe Phe Val Pro Ser Ala Ser Ser Arg Met
    50                  55                  60 ttt ctt ctc gtg gga gct ccc aaa gca aac acc acc cag cct ggg att      240
Phe Leu Leu Val Gly Ala Pro Lys Ala Asn Thr Thr Gln Pro Gly Ile
65                  70                  75                  80 gtg gaa gga ggg cag gtc ctc aaa tgt gac tgg tct tct acc cgc cgg      288
Val Glu Gly Gly Gln Val Leu Lys Cys Asp Trp Ser Ser Thr Arg Arg
                85                  90                  95 tgc cag cca att gaa ttt gat gca aca ggc aat aga gat tat gcc aag      336
Cys Gln Pro Ile Glu Phe Asp Ala Thr Gly Asn Arg Asp Tyr Ala Lys
            100                 105                 110 gat gat cca ttg gaa ttt aag tcc cat cag tgg ttt gga gca tct gtg      384
Asp Asp Pro Leu Glu Phe Lys Ser His Gln Trp Phe Gly Ala Ser Val
        115                 120                 125 agg tcg aaa cag gat aaa att ttg gcc tgt gcc cca ttg tac cat tgg      432
Arg Ser Lys Gln Asp Lys Ile Leu Ala Cys Ala Pro Leu Tyr His Trp
    130                 135                 140 aga act gag atg aaa cag gag cga gag cct gtt gga aca tgc ttt ctt      480
Arg Thr Glu Met Lys Gln Glu Arg Glu Pro Val Gly Thr Cys Phe Leu
145                 150                 155                 160 caa gat gga aca aag act gtt gag tat gct cca tgt aga tca caa gat      528
Gln Asp Gly Thr Lys Thr Val Glu Tyr Ala Pro Cys Arg Ser Gln Asp
                165                 170                 175 att gat gct gat gga cag gga ttt tgt caa gga gga ttc agc att gat      576
Ile Asp Ala Asp Gly Gln Gly Phe Cys Gln Gly Gly Phe Ser Ile Asp
            180                 185                 190 ttt act aaa gct gac aga gta ctt ctt ggt ggt cct ggt agc ttt tat      624
Phe Thr Lys Ala Asp Arg Val Leu Leu Gly Gly Pro Gly Ser Phe Tyr
        195                 200                 205 tgg caa ggt cag ctt att tcg gat caa gtg gca gaa atc gta tct aaa      672
Trp Gln Gly Gln Leu Ile Ser Asp Gln Val Ala Glu Ile Val Ser Lys
    210                 215                 220 tac gac ccc aat gtt tac agc atc aag tat aat aac caa tta gca act      720
Tyr Asp Pro Asn Val Tyr Ser Ile Lys Tyr Asn Asn Gln Leu Ala Thr
```

```
                        225                 230                 235                 240
cgg act gca caa gct att ttt gat gac agc tat ttg ggt tat tct gtg       768
Arg Thr Ala Gln Ala Ile Phe Asp Asp Ser Tyr Leu Gly Tyr Ser Val
                245                 250                 255 gct gtc gga gat ttc aat ggt gat ggc ata gat gac ttt gtt tca gga       816
Ala Val Gly Asp Phe Asn Gly Asp Gly Ile Asp Asp Phe Val Ser Gly
            260                 265                 270 gtt cca aga gca gca agg act ttg gga atg gtt tat att tat gat ggg       864
Val Pro Arg Ala Ala Arg Thr Leu Gly Met Val Tyr Ile Tyr Asp Gly
        275                 280                 285 aag aac atg tcc tcc tta tac aat ttt act ggc gag cag atg gct gca       912
Lys Asn Met Ser Ser Leu Tyr Asn Phe Thr Gly Glu Gln Met Ala Ala
    290                 295                 300 tat ttc gga ttt tct gta gct gcc act gac att aat gga gat gat tat       960
Tyr Phe Gly Phe Ser Val Ala Ala Thr Asp Ile Asn Gly Asp Asp Tyr
305                 310                 315                 320 gca gat gtg ttt att gga gca cct ctc ttc atg gat cgt ggc tct gat      1008
Ala Asp Val Phe Ile Gly Ala Pro Leu Phe Met Asp Arg Gly Ser Asp
                325                 330                 335 ggc aaa ctc caa gag gtg ggg cag gtc tca gtg tct cta cag aga gct      1056
Gly Lys Leu Gln Glu Val Gly Gln Val Ser Val Ser Leu Gln Arg Ala
            340                 345                 350 tca gga gac ttc cag acg aca aag ctg aat gga ttt gag gtc ttt gca      1104
Ser Gly Asp Phe Gln Thr Thr Lys Leu Asn Gly Phe Glu Val Phe Ala
        355                 360                 365 cgg ttt ggc agt gcc ata gct cct ttg gga gat ctg gac cag gat ggt      1152
Arg Phe Gly Ser Ala Ile Ala Pro Leu Gly Asp Leu Asp Gln Asp Gly
    370                 375                 380 ttc aat gat att gca att gct gct cca tat ggg ggt gaa gat aaa aaa      1200
Phe Asn Asp Ile Ala Ile Ala Ala Pro Tyr Gly Gly Glu Asp Lys Lys
385                 390                 395                 400 gga att gtt tat atc ttc aat gga aga tca aca ggc ttg aac gca gtc      1248
Gly Ile Val Tyr Ile Phe Asn Gly Arg Ser Thr Gly Leu Asn Ala Val
                405                 410                 415 cca tct caa atc ctt gaa ggg cag tgg gct gct cga agc atg cca cca      1296
Pro Ser Gln Ile Leu Glu Gly Gln Trp Ala Ala Arg Ser Met Pro Pro
            420                 425                 430 agc ttt ggc tat tca atg aaa gga gcc aca gat ata gac aaa aat gga      1344
Ser Phe Gly Tyr Ser Met Lys Gly Ala Thr Asp Ile Asp Lys Asn Gly
        435                 440                 445 tat cca gac tta att gta gga gct ttt ggt gta gat cga gct atc tta      1392
Tyr Pro Asp Leu Ile Val Gly Ala Phe Gly Val Asp Arg Ala Ile Leu
    450                 455                 460 tac agg gcc aga cca gtt atc act gta aat gct ggt ctt gaa gtg tac      1440
Tyr Arg Ala Arg Pro Val Ile Thr Val Asn Ala Gly Leu Glu Val Tyr
465                 470                 475                 480 cct agc att tta aat caa gac aat aaa acc tgc tca ctg cct gga aca      1488
Pro Ser Ile Leu Asn Gln Asp Asn Lys Thr Cys Ser Leu Pro Gly Thr
                485                 490                 495 gct ctc aaa gtt tcc tgt ttt aat gtt agg ttc tgc tta aag gca gat      1536
Ala Leu Lys Val Ser Cys Phe Asn Val Arg Phe Cys Leu Lys Ala Asp
            500                 505                 510 ggc aaa gga gta ctt ccc agg aaa ctt aat ttc cag gtg gaa ctt ctt      1584
Gly Lys Gly Val Leu Pro Arg Lys Leu Asn Phe Gln Val Glu Leu Leu
        515                 520                 525 ttg gat aaa ctc aag caa aag gga gca att cga cga gca ctg ttt ctc      1632
Leu Asp Lys Leu Lys Gln Lys Gly Ala Ile Arg Arg Ala Leu Phe Leu
    530                 535                 540 tac agc agg tcc cca agt cac tcc aag aac atg act att tca agg ggg      1680
```

-continued

```
Tyr Ser Arg Ser Pro Ser His Ser Lys Asn Met Thr Ile Ser Arg Gly
545                 550                 555                 560 gga ctg atg cag tgt gag gaa ttg ata gcg tat ctg cgg gat gaa tct    1728
Gly Leu Met Gln Cys Glu Glu Leu Ile Ala Tyr Leu Arg Asp Glu Ser
                565                 570                 575 gaa ttt aga gac aaa ctc act cca att act att ttt atg gaa tat cgg    1776
Glu Phe Arg Asp Lys Leu Thr Pro Ile Thr Ile Phe Met Glu Tyr Arg
            580                 585                 590 ttg gat tat aga aca gct gct gat aca aca ggc ttg caa ccc att ctt    1824
Leu Asp Tyr Arg Thr Ala Ala Asp Thr Thr Gly Leu Gln Pro Ile Leu
        595                 600                 605 aac cag ttc acg cct gct aac att agt cga cag gct cac att cta ctt    1872
Asn Gln Phe Thr Pro Ala Asn Ile Ser Arg Gln Ala His Ile Leu Leu
    610                 615                 620 gac tgt ggt gaa gac aat gtc tgt aaa ccc aag ctg gaa gtt tct gta    1920
Asp Cys Gly Glu Asp Asn Val Cys Lys Pro Lys Leu Glu Val Ser Val
625                 630                 635                 640 gat agt gat caa aag aag atc tat att ggg gat gac aac cct ctg aca    1968
Asp Ser Asp Gln Lys Lys Ile Tyr Ile Gly Asp Asp Asn Pro Leu Thr
                645                 650                 655 ttg att gtt aag gct cag aat caa gga gaa ggt gcc tac gaa gct gag    2016
Leu Ile Val Lys Ala Gln Asn Gln Gly Glu Gly Ala Tyr Glu Ala Glu
            660                 665                 670 ctc atc gtt tcc att cca ctg cag gct gat ttc atc ggg gtt gtc cga    2064
Leu Ile Val Ser Ile Pro Leu Gln Ala Asp Phe Ile Gly Val Val Arg
        675                 680                 685 aac aat gaa gcc tta gca aga ctt tcc tgt gca ttt aag aca gaa aac    2112
Asn Asn Glu Ala Leu Ala Arg Leu Ser Cys Ala Phe Lys Thr Glu Asn
    690                 695                 700 caa act cgc cag gtg gta tgt gac ctt gga aac cca atg aag gct gga    2160
Gln Thr Arg Gln Val Val Cys Asp Leu Gly Asn Pro Met Lys Ala Gly
705                 710                 715                 720 act caa ctc tta gct ggt ctt cgt ttc agt gtg cac cag cag tca gag    2208
Thr Gln Leu Leu Ala Gly Leu Arg Phe Ser Val His Gln Gln Ser Glu
                725                 730                 735 atg gat act tct gtg aaa ttt gac tta caa atc caa agc tca aat cta    2256
Met Asp Thr Ser Val Lys Phe Asp Leu Gln Ile Gln Ser Ser Asn Leu
            740                 745                 750 ttt gac aaa gta agc cca gtt gta tct cac aaa gtt gat ctt gct gtt    2304
Phe Asp Lys Val Ser Pro Val Val Ser His Lys Val Asp Leu Ala Val
        755                 760                 765 tta gct gca gtt gag ata aga gga gtc tcg agt cct gat cat atc ttt    2352
Leu Ala Ala Val Glu Ile Arg Gly Val Ser Ser Pro Asp His Ile Phe
    770                 775                 780 ctt ccg att cca aac tgg gag cac aag gag aac cct gag act gaa gaa    2400
Leu Pro Ile Pro Asn Trp Glu His Lys Glu Asn Pro Glu Thr Glu Glu
785                 790                 795                 800 gat gtt ggg cca gtt gtt cag cac atc tat gag ctg aga aac aat ggt    2448
Asp Val Gly Pro Val Val Gln His Ile Tyr Glu Leu Arg Asn Asn Gly
                805                 810                 815 cca agt tca ttc agc aag gca atg ctc cat ctt cag tgg cct tac aaa    2496
Pro Ser Ser Phe Ser Lys Ala Met Leu His Leu Gln Trp Pro Tyr Lys
            820                 825                 830 tat aat aat aac act ctg ttg tat atc ctt cat tat gat att gat gga    2544
Tyr Asn Asn Asn Thr Leu Leu Tyr Ile Leu His Tyr Asp Ile Asp Gly
        835                 840                 845 cca atg aac tgc act tca gat atg gag atc aac cct ttg aga att aag    2592
Pro Met Asn Cys Thr Ser Asp Met Glu Ile Asn Pro Leu Arg Ile Lys
    850                 855                 860
```

```
atc tca tct ttg caa aca act gaa aag aat gac acg gtt gcc ggg caa      2640
Ile Ser Ser Leu Gln Thr Thr Glu Lys Asn Asp Thr Val Ala Gly Gln
865                 870                 875                 880 ggt gag cgg gac cat ctc atc act aag cgg gat ctt gcc ctc agt gaa      2688
Gly Glu Arg Asp His Leu Ile Thr Lys Arg Asp Leu Ala Leu Ser Glu
            885                 890                 895 gga gat att cac act ttg ggt tgt gga gtt gct cag tgc ttg aag att      2736
Gly Asp Ile His Thr Leu Gly Cys Gly Val Ala Gln Cys Leu Lys Ile
        900                 905                 910 gtc tgc caa gtt ggg aga tta gac aga gga aag agt gca atc ttg tac      2784
Val Cys Gln Val Gly Arg Leu Asp Arg Gly Lys Ser Ala Ile Leu Tyr
    915                 920                 925 gta aag tca tta ctg tgg act gag act ttt atg aat aaa gaa aat cag      2832
Val Lys Ser Leu Leu Trp Thr Glu Thr Phe Met Asn Lys Glu Asn Gln
930                 935                 940 aat cat tcc tat tct ctg aag tcg tct gct tca ttt aat gtc ata gag      2880
Asn His Ser Tyr Ser Leu Lys Ser Ser Ala Ser Phe Asn Val Ile Glu
945                 950                 955                 960 ttt cct tat aag aat ctt cca att gag gat atc acc aac tcc aca ttg      2928
Phe Pro Tyr Lys Asn Leu Pro Ile Glu Asp Ile Thr Asn Ser Thr Leu
            965                 970                 975 gtt acc act aat gtc acc tgg ggc att cag cca gcg ccc atg cct gtg      2976
Val Thr Thr Asn Val Thr Trp Gly Ile Gln Pro Ala Pro Met Pro Val
        980                 985                 990 cct gtg tgg gtg atc att tta gca gtt cta gca gga ttg ttg cta ctg      3024
Pro Val Trp Val Ile Ile Leu Ala Val Leu Ala Gly Leu Leu Leu Leu
    995                 1000                1005 gct gtt ttg gta ttt gta atg tac agg atg ggc ttt ttt aaa cgg         3069
Ala Val Leu Val Phe Val Met Tyr Arg Met Gly Phe Phe Lys Arg
    1010                1015                1020 gtc cgg cca cct caa gaa gaa caa gaa agg gag cag ctt caa cct         3114
Val Arg Pro Pro Gln Glu Glu Gln Glu Arg Glu Gln Leu Gln Pro
    1025                1030                1035 cat gaa aat ggt gaa gga aac tca gaa act taa                         3147
His Glu Asn Gly Glu Gly Asn Ser Glu Thr
    1040                1045

<210> SEQ ID NO 9
<211> LENGTH: 1048
<212> TYPE: PRT
<213> ORGANISM: Homo Sapiens

<400> SEQUENCE: 9

Met Ala Phe Pro Pro Arg Arg Leu Arg Leu Gly Pro Arg Gly Leu
1               5                   10                  15

Pro Leu Leu Leu Ser Gly Leu Leu Pro Leu Cys Arg Ala Phe Asn
                20                  25                  30

Leu Asp Val Asp Ser Pro Ala Glu Tyr Ser Gly Pro Glu Gly Ser Tyr
            35                  40                  45

Phe Gly Phe Ala Val Asp Phe Val Pro Ser Ala Ser Ser Arg Met
        50                  55                  60

Phe Leu Leu Val Gly Ala Pro Lys Ala Asn Thr Thr Gln Pro Gly Ile
65                  70                  75                  80

Val Glu Gly Gly Gln Val Leu Lys Cys Asp Trp Ser Ser Thr Arg Arg
                85                  90                  95

Cys Gln Pro Ile Glu Phe Asp Ala Thr Gly Asn Arg Asp Tyr Ala Lys
            100                 105                 110

Asp Asp Pro Leu Glu Phe Lys Ser His Gln Trp Phe Gly Ala Ser Val
        115                 120                 125
```

-continued

```
Arg Ser Lys Gln Asp Lys Ile Leu Ala Cys Ala Pro Leu Tyr His Trp
    130                 135                 140
Arg Thr Glu Met Lys Gln Arg Glu Pro Val Gly Thr Cys Phe Leu
145                 150                 155                 160
Gln Asp Gly Thr Lys Thr Val Glu Tyr Ala Pro Cys Arg Ser Gln Asp
                165                 170                 175
Ile Asp Ala Asp Gly Gln Gly Phe Cys Gln Gly Gly Phe Ser Ile Asp
            180                 185                 190
Phe Thr Lys Ala Asp Arg Val Leu Leu Gly Gly Pro Gly Ser Phe Tyr
        195                 200                 205
Trp Gln Gly Gln Leu Ile Ser Asp Gln Val Ala Glu Ile Val Ser Lys
    210                 215                 220
Tyr Asp Pro Asn Val Tyr Ser Ile Lys Tyr Asn Asn Gln Leu Ala Thr
225                 230                 235                 240
Arg Thr Ala Gln Ala Ile Phe Asp Asp Ser Tyr Leu Gly Tyr Ser Val
                245                 250                 255
Ala Val Gly Asp Phe Asn Gly Asp Gly Ile Asp Asp Phe Val Ser Gly
            260                 265                 270
Val Pro Arg Ala Ala Arg Thr Leu Gly Met Val Tyr Ile Tyr Asp Gly
        275                 280                 285
Lys Asn Met Ser Ser Leu Tyr Asn Phe Thr Gly Glu Gln Met Ala Ala
    290                 295                 300
Tyr Phe Gly Phe Ser Val Ala Ala Thr Asp Ile Asn Gly Asp Asp Tyr
305                 310                 315                 320
Ala Asp Val Phe Ile Gly Ala Pro Leu Phe Met Asp Arg Gly Ser Asp
                325                 330                 335
Gly Lys Leu Gln Glu Val Gly Gln Val Ser Val Ser Leu Gln Arg Ala
            340                 345                 350
Ser Gly Asp Phe Gln Thr Thr Lys Leu Asn Gly Phe Glu Val Phe Ala
        355                 360                 365
Arg Phe Gly Ser Ala Ile Ala Pro Leu Gly Asp Leu Asp Gln Asp Gly
    370                 375                 380
Phe Asn Asp Ile Ala Ile Ala Ala Pro Tyr Gly Gly Glu Asp Lys Lys
385                 390                 395                 400
Gly Ile Val Tyr Ile Phe Asn Gly Arg Ser Thr Gly Leu Asn Ala Val
                405                 410                 415
Pro Ser Gln Ile Leu Glu Gly Gln Trp Ala Ala Arg Ser Met Pro Pro
            420                 425                 430
Ser Phe Gly Tyr Ser Met Lys Gly Ala Thr Asp Ile Asp Lys Asn Gly
        435                 440                 445
Tyr Pro Asp Leu Ile Val Gly Ala Phe Gly Val Asp Arg Ala Ile Leu
    450                 455                 460
Tyr Arg Ala Arg Pro Val Ile Thr Val Asn Ala Gly Leu Glu Val Tyr
465                 470                 475                 480
Pro Ser Ile Leu Asn Gln Asp Asn Lys Thr Cys Ser Leu Pro Gly Thr
                485                 490                 495
Ala Leu Lys Val Ser Cys Phe Asn Val Arg Phe Cys Leu Lys Ala Asp
            500                 505                 510
Gly Lys Gly Val Leu Pro Arg Lys Leu Asn Phe Gln Val Glu Leu Leu
        515                 520                 525
Leu Asp Lys Leu Lys Gln Lys Gly Ala Ile Arg Arg Ala Leu Phe Leu
    530                 535                 540
```

-continued

```
Tyr Ser Arg Ser Pro Ser His Ser Lys Asn Met Thr Ile Ser Arg Gly
545                 550                 555                 560
Gly Leu Met Gln Cys Glu Glu Leu Ile Ala Tyr Leu Arg Asp Glu Ser
                565                 570                 575
Glu Phe Arg Asp Lys Leu Thr Pro Ile Thr Ile Phe Met Glu Tyr Arg
            580                 585                 590
Leu Asp Tyr Arg Thr Ala Ala Asp Thr Thr Gly Leu Gln Pro Ile Leu
        595                 600                 605
Asn Gln Phe Thr Pro Ala Asn Ile Ser Arg Gln Ala His Ile Leu Leu
    610                 615                 620
Asp Cys Gly Glu Asp Asn Val Cys Lys Pro Lys Leu Glu Val Ser Val
625                 630                 635                 640
Asp Ser Asp Gln Lys Lys Ile Tyr Ile Gly Asp Asp Asn Pro Leu Thr
                645                 650                 655
Leu Ile Val Lys Ala Gln Asn Gln Gly Glu Gly Ala Tyr Glu Ala Glu
            660                 665                 670
Leu Ile Val Ser Ile Pro Leu Gln Ala Asp Phe Ile Gly Val Val Arg
        675                 680                 685
Asn Asn Glu Ala Leu Ala Arg Leu Ser Cys Ala Phe Lys Thr Glu Asn
    690                 695                 700
Gln Thr Arg Gln Val Val Cys Asp Leu Gly Asn Pro Met Lys Ala Gly
705                 710                 715                 720
Thr Gln Leu Leu Ala Gly Leu Arg Phe Ser Val His Gln Gln Ser Glu
                725                 730                 735
Met Asp Thr Ser Val Lys Phe Asp Leu Gln Ile Gln Ser Ser Asn Leu
            740                 745                 750
Phe Asp Lys Val Ser Pro Val Val Ser His Lys Val Asp Leu Ala Val
        755                 760                 765
Leu Ala Ala Val Glu Ile Arg Gly Val Ser Ser Pro Asp His Ile Phe
    770                 775                 780
Leu Pro Ile Pro Asn Trp Glu His Lys Glu Asn Pro Glu Thr Glu Glu
785                 790                 795                 800
Asp Val Gly Pro Val Val Gln His Ile Tyr Glu Leu Arg Asn Asn Gly
                805                 810                 815
Pro Ser Ser Phe Ser Lys Ala Met Leu His Leu Gln Trp Pro Tyr Lys
            820                 825                 830
Tyr Asn Asn Asn Thr Leu Leu Tyr Ile Leu His Tyr Asp Ile Asp Gly
        835                 840                 845
Pro Met Asn Cys Thr Ser Asp Met Glu Ile Asn Pro Leu Arg Ile Lys
    850                 855                 860
Ile Ser Ser Leu Gln Thr Thr Glu Lys Asn Asp Thr Val Ala Gly Gln
865                 870                 875                 880
Gly Glu Arg Asp His Leu Ile Thr Lys Arg Asp Leu Ala Leu Ser Glu
                885                 890                 895
Gly Asp Ile His Thr Leu Gly Cys Gly Val Ala Gln Cys Leu Lys Ile
            900                 905                 910
Val Cys Gln Val Gly Arg Leu Asp Arg Gly Lys Ser Ala Ile Leu Tyr
        915                 920                 925
Val Lys Ser Leu Leu Trp Thr Glu Thr Phe Met Asn Lys Glu Asn Gln
    930                 935                 940
Asn His Ser Tyr Ser Leu Lys Ser Ser Ala Ser Phe Asn Val Ile Glu
945                 950                 955                 960
Phe Pro Tyr Lys Asn Leu Pro Ile Glu Asp Ile Thr Asn Ser Thr Leu
```

```
                965              970              975
Val Thr Thr Asn Val Thr Trp Gly Ile Gln Pro Ala Pro Met Pro Val
            980              985              990

Pro Val Trp Val Ile Ile Leu Ala Val Leu Ala Gly Leu Leu Leu Leu
            995             1000             1005

Ala Val Leu Val Phe Val Met Tyr Arg Met Gly Phe Phe Lys Arg
           1010             1015             1020

Val Arg Pro Pro Gln Glu Glu Gln Glu Arg Glu Gln Leu Gln Pro
           1025             1030             1035

His Glu Asn Gly Glu Gly Asn Ser Glu Thr
           1040             1045

<210> SEQ ID NO 10
<211> LENGTH: 2367
<212> TYPE: DNA
<213> ORGANISM: Homo Sapiens
<220> FEATURE:
<221> NAME/KEY: CDS
<222> LOCATION: (1)..(2364)
<223> OTHER INFORMATION: Sequence coding for integrin beta 3 subunit

<400> SEQUENCE: 10 atg cga gcg cgg ccg cgg ccc cgg ccg ctc tgg gcg act gtg ctg gcg       48
Met Arg Ala Arg Pro Arg Pro Arg Pro Leu Trp Ala Thr Val Leu Ala
1               5                  10                  15 ctg ggg gcg ctg gcg ggc gtt ggc gta gga ggg ccc aac atc tgt acc       96
Leu Gly Ala Leu Ala Gly Val Gly Val Gly Gly Pro Asn Ile Cys Thr
            20                  25                  30 acg cga ggt gtg agc tcc tgc cag cag tgc ctg gct gtg agc ccc atg      144
Thr Arg Gly Val Ser Ser Cys Gln Gln Cys Leu Ala Val Ser Pro Met
        35                  40                  45 tgt gcc tgg tgc tct gat gag gcc ctg cct ctg ggc tca cct cgc tgt      192
Cys Ala Trp Cys Ser Asp Glu Ala Leu Pro Leu Gly Ser Pro Arg Cys
    50                  55                  60 gac ctg aag gag aat ctg ctg aag gat aac tgt gcc cca gaa tcc atc      240
Asp Leu Lys Glu Asn Leu Leu Lys Asp Asn Cys Ala Pro Glu Ser Ile
65                  70                  75                  80 gag ttc cca gtg agt gag gcc cga gta cta gag gac agg ccc ctc agc      288
Glu Phe Pro Val Ser Glu Ala Arg Val Leu Glu Asp Arg Pro Leu Ser
                85                  90                  95 gac aag ggc tct gga gac agc tcc cag gtc act caa gtc agt ccc cag      336
Asp Lys Gly Ser Gly Asp Ser Ser Gln Val Thr Gln Val Ser Pro Gln
            100                 105                 110 agg att gca ctc cgg ctc cgg cca gat gat tcg aag aat ttc tcc atc      384
Arg Ile Ala Leu Arg Leu Arg Pro Asp Asp Ser Lys Asn Phe Ser Ile
        115                 120                 125 caa gtg cgg cag gtg gag gat tac cct gtg gac atc tac tac ttg atg      432
Gln Val Arg Gln Val Glu Asp Tyr Pro Val Asp Ile Tyr Tyr Leu Met
    130                 135                 140 gac ctg tct tac tcc atg aag gat gat ctg tgg agc atc cag aac ctg      480
Asp Leu Ser Tyr Ser Met Lys Asp Asp Leu Trp Ser Ile Gln Asn Leu
145                 150                 155                 160 ggt acc aag ctg gcc acc cag atg cga aag ctc acc agt aac ctg cgg      528
Gly Thr Lys Leu Ala Thr Gln Met Arg Lys Leu Thr Ser Asn Leu Arg
                165                 170                 175 att ggc ttc ggg gca ttt gtg gac aag cct gtg tca cca tac atg tat      576
Ile Gly Phe Gly Ala Phe Val Asp Lys Pro Val Ser Pro Tyr Met Tyr
            180                 185                 190 atc tcc cca cca gag gcc ctc gaa aac ccc tgc tat gat atg aag acc      624
Ile Ser Pro Pro Glu Ala Leu Glu Asn Pro Cys Tyr Asp Met Lys Thr
```

-continued

|  |  |  |  |  |  |  |  |  |  |  |  |  |  |  |  |
|---|---|---|---|---|---|---|---|---|---|---|---|---|---|---|---|
|  |  | 195 |  |  |  | 200 |  |  |  | 205 |  |  |  |  |  |
| acc | tgc | ttg | ccc | atg | ttt | ggc | tac | aaa | cac | gtg | ctg | acg | cta | act | gac | 672 |
| Thr | Cys | Leu | Pro | Met | Phe | Gly | Tyr | Lys | His | Val | Leu | Thr | Leu | Thr | Asp |  |
|  | 210 |  |  |  | 215 |  |  |  |  | 220 |  |  |  |  |  |  |
| cag | gtg | acc | cgt | ttc | aat | gag | gaa | gtg | aag | aag | cag | agt | gtg | tca | cgg | 720 |
| Gln | Val | Thr | Arg | Phe | Asn | Glu | Glu | Val | Lys | Lys | Gln | Ser | Val | Ser | Arg |  |
| 225 |  |  |  |  | 230 |  |  |  |  | 235 |  |  |  |  | 240 |  |
| aac | cga | gat | gcc | cca | gag | ggt | ggc | ttt | gat | gcc | atc | atg | cag | gct | aca | 768 |
| Asn | Arg | Asp | Ala | Pro | Glu | Gly | Gly | Phe | Asp | Ala | Ile | Met | Gln | Ala | Thr |  |
|  |  |  |  | 245 |  |  |  |  | 250 |  |  |  |  | 255 |  |  |
| gtc | tgt | gat | gaa | aag | att | ggc | tgg | agg | aat | gat | gca | tcc | cac | ttg | ctg | 816 |
| Val | Cys | Asp | Glu | Lys | Ile | Gly | Trp | Arg | Asn | Asp | Ala | Ser | His | Leu | Leu |  |
|  |  |  |  | 260 |  |  |  |  | 265 |  |  |  |  | 270 |  |  |
| gtg | ttt | acc | act | gat | gcc | aag | act | cat | ata | gca | ttg | gac | gga | agg | ctg | 864 |
| Val | Phe | Thr | Thr | Asp | Ala | Lys | Thr | His | Ile | Ala | Leu | Asp | Gly | Arg | Leu |  |
|  |  |  | 275 |  |  |  |  | 280 |  |  |  |  | 285 |  |  |  |
| gca | ggc | att | gtc | cag | cct | aat | gac | ggg | cag | tgt | cat | gtt | ggt | agt | gac | 912 |
| Ala | Gly | Ile | Val | Gln | Pro | Asn | Asp | Gly | Gln | Cys | His | Val | Gly | Ser | Asp |  |
|  |  | 290 |  |  |  |  | 295 |  |  |  |  | 300 |  |  |  |  |
| aat | cat | tac | tct | gcc | tcc | act | acc | atg | gat | tat | ccc | tct | ttg | ggg | ctg | 960 |
| Asn | His | Tyr | Ser | Ala | Ser | Thr | Thr | Met | Asp | Tyr | Pro | Ser | Leu | Gly | Leu |  |
| 305 |  |  |  |  | 310 |  |  |  |  | 315 |  |  |  |  | 320 |  |
| atg | act | gag | aag | cta | tcc | cag | aaa | aac | atc | aat | ttg | atc | ttt | gca | gtg | 1008 |
| Met | Thr | Glu | Lys | Leu | Ser | Gln | Lys | Asn | Ile | Asn | Leu | Ile | Phe | Ala | Val |  |
|  |  |  |  | 325 |  |  |  |  | 330 |  |  |  |  | 335 |  |  |
| act | gaa | aat | gta | gtc | aat | ctc | tat | cag | aac | tat | agt | gag | ctc | atc | cca | 1056 |
| Thr | Glu | Asn | Val | Val | Asn | Leu | Tyr | Gln | Asn | Tyr | Ser | Glu | Leu | Ile | Pro |  |
|  |  |  |  | 340 |  |  |  |  | 345 |  |  |  |  | 350 |  |  |
| ggg | acc | aca | gtt | ggg | gtt | ctg | tcc | atg | gat | tcc | agc | aat | gtc | ctc | cag | 1104 |
| Gly | Thr | Thr | Val | Gly | Val | Leu | Ser | Met | Asp | Ser | Ser | Asn | Val | Leu | Gln |  |
|  |  |  | 355 |  |  |  |  | 360 |  |  |  |  | 365 |  |  |  |
| ctc | att | gtt | gat | gct | tat | ggg | aaa | atc | cgt | tct | aaa | gta | gag | ctg | gaa | 1152 |
| Leu | Ile | Val | Asp | Ala | Tyr | Gly | Lys | Ile | Arg | Ser | Lys | Val | Glu | Leu | Glu |  |
|  |  | 370 |  |  |  |  | 375 |  |  |  |  | 380 |  |  |  |  |
| gtg | cgt | gac | ctc | cct | gaa | gag | ttg | tct | cta | tcc | ttc | aat | gcc | acc | tgc | 1200 |
| Val | Arg | Asp | Leu | Pro | Glu | Glu | Leu | Ser | Leu | Ser | Phe | Asn | Ala | Thr | Cys |  |
| 385 |  |  |  |  | 390 |  |  |  |  | 395 |  |  |  |  | 400 |  |
| ctc | aac | aat | gag | gtc | atc | cct | ggc | ctc | aag | tct | tgt | atg | gga | ctc | aag | 1248 |
| Leu | Asn | Asn | Glu | Val | Ile | Pro | Gly | Leu | Lys | Ser | Cys | Met | Gly | Leu | Lys |  |
|  |  |  |  | 405 |  |  |  |  | 410 |  |  |  |  | 415 |  |  |
| att | gga | gac | acg | gtg | agc | ttc | agc | att | gag | gcc | aag | gtg | cga | ggc | tgt | 1296 |
| Ile | Gly | Asp | Thr | Val | Ser | Phe | Ser | Ile | Glu | Ala | Lys | Val | Arg | Gly | Cys |  |
|  |  |  | 420 |  |  |  |  | 425 |  |  |  |  | 430 |  |  |  |
| ccc | cag | gag | aag | gag | aag | tcc | ttt | acc | ata | aag | ccc | gtg | ggc | ttc | aag | 1344 |
| Pro | Gln | Glu | Lys | Glu | Lys | Ser | Phe | Thr | Ile | Lys | Pro | Val | Gly | Phe | Lys |  |
|  |  |  | 435 |  |  |  |  | 440 |  |  |  |  | 445 |  |  |  |
| gac | agc | ctg | atc | gtc | cag | gtc | acc | ttt | gat | tgt | gac | tgt | gcc | tgc | cag | 1392 |
| Asp | Ser | Leu | Ile | Val | Gln | Val | Thr | Phe | Asp | Cys | Asp | Cys | Ala | Cys | Gln |  |
| 450 |  |  |  |  | 455 |  |  |  |  | 460 |  |  |  |  |  |  |
| gcc | caa | gct | gaa | cct | aat | agc | cat | cgc | tgc | aac | aat | ggc | aat | ggg | acc | 1440 |
| Ala | Gln | Ala | Glu | Pro | Asn | Ser | His | Arg | Cys | Asn | Asn | Gly | Asn | Gly | Thr |  |
| 465 |  |  |  |  | 470 |  |  |  |  | 475 |  |  |  |  | 480 |  |
| ttt | gag | tgt | ggg | gta | tgc | cgt | tgt | ggg | cct | ggc | tgg | ctg | gga | tcc | cag | 1488 |
| Phe | Glu | Cys | Gly | Val | Cys | Arg | Cys | Gly | Pro | Gly | Trp | Leu | Gly | Ser | Gln |  |
|  |  |  |  | 485 |  |  |  |  | 490 |  |  |  |  | 495 |  |  |
| tgt | gag | tgc | tca | gag | gag | gac | tat | cgc | cct | tcc | cag | cag | gac | gaa | tgc | 1536 |
| Cys | Glu | Cys | Ser | Glu | Glu | Asp | Tyr | Arg | Pro | Ser | Gln | Gln | Asp | Glu | Cys |  |
|  |  |  | 500 |  |  |  |  | 505 |  |  |  |  | 510 |  |  |  |
| agc | ccc | cgg | gag | ggt | cag | ccc | gtc | tgc | agc | cag | cgg | ggc | gag | tgc | ctc | 1584 |

```
                Ser Pro Arg Glu Gly Gln Pro Val Cys Ser Gln Arg Gly Glu Cys Leu
                    515                 520                 525 tgt ggt caa tgt gtc tgc cac agc agt gac ttt ggc aag atc acg ggc      1632
Cys Gly Gln Cys Val Cys His Ser Ser Asp Phe Gly Lys Ile Thr Gly
530                 535                 540 aag tac tgc gag tgt gac gac ttc tcc tgt gtc cgc tac aag ggg gag      1680
Lys Tyr Cys Glu Cys Asp Asp Phe Ser Cys Val Arg Tyr Lys Gly Glu
545                 550                 555                 560 atg tgc tca ggc cat ggc cag tgc agc tgt ggg gac tgc ctg tgt gac      1728
Met Cys Ser Gly His Gly Gln Cys Ser Cys Gly Asp Cys Leu Cys Asp
                565                 570                 575 tcc gac tgg acc ggc tac tac tgc aac tgt acc acg cgt act gac acc      1776
Ser Asp Trp Thr Gly Tyr Tyr Cys Asn Cys Thr Thr Arg Thr Asp Thr
            580                 585                 590 tgc atg tcc agc aat ggg ctg ctg tgc agc ggc cgc ggc aag tgt gaa      1824
Cys Met Ser Ser Asn Gly Leu Leu Cys Ser Gly Arg Gly Lys Cys Glu
        595                 600                 605 tgt ggc agc tgt gtc tgt atc cag ccg ggc tcc tat ggg gac acc tgt      1872
Cys Gly Ser Cys Val Cys Ile Gln Pro Gly Ser Tyr Gly Asp Thr Cys
    610                 615                 620 gag aag tgc ccc acc tgc cca gat gcc tgc acc ttt aag aaa gaa tgt      1920
Glu Lys Cys Pro Thr Cys Pro Asp Ala Cys Thr Phe Lys Lys Glu Cys
625                 630                 635                 640 gtg gag tgt aag aag ttt gac cgg gag ccc tac atg acc gaa aat acc      1968
Val Glu Cys Lys Lys Phe Asp Arg Glu Pro Tyr Met Thr Glu Asn Thr
                645                 650                 655 tgc aac cgt tac tgc cgt gac gag att gag tca gtg aaa gag ctt aag      2016
Cys Asn Arg Tyr Cys Arg Asp Glu Ile Glu Ser Val Lys Glu Leu Lys
            660                 665                 670 gac act ggc aag gat gca gtg aat tgt acc tat aag aat gag gat gac      2064
Asp Thr Gly Lys Asp Ala Val Asn Cys Thr Tyr Lys Asn Glu Asp Asp
        675                 680                 685 tgt gtc gtc aga ttc cag tac tat gaa gat tct agt gga aag tcc atc      2112
Cys Val Val Arg Phe Gln Tyr Tyr Glu Asp Ser Ser Gly Lys Ser Ile
    690                 695                 700 ctg tat gtg gta gaa gag cca gag tgt ccc aag ggc cct gac atc ctg      2160
Leu Tyr Val Val Glu Glu Pro Glu Cys Pro Lys Gly Pro Asp Ile Leu
705                 710                 715                 720 gtg gtc ctg ctc tca gtg atg ggg gcc att ctg ctc att ggc ctt gcc      2208
Val Val Leu Leu Ser Val Met Gly Ala Ile Leu Leu Ile Gly Leu Ala
                725                 730                 735 gcc ctg ctc atc tgg aaa ctc ctc atc acc atc cac gac cga aaa gaa      2256
Ala Leu Leu Ile Trp Lys Leu Leu Ile Thr Ile His Asp Arg Lys Glu
            740                 745                 750 ttc gct aaa ttt gag gaa gaa cgc gcc aga gca aaa tgg gac aca gcc      2304
Phe Ala Lys Phe Glu Glu Glu Arg Ala Arg Ala Lys Trp Asp Thr Ala
        755                 760                 765 aac aac cca ctg tat aaa gag gcc acg tct acc ttc acc aat atc acg      2352
Asn Asn Pro Leu Tyr Lys Glu Ala Thr Ser Thr Phe Thr Asn Ile Thr
    770                 775                 780 tac cgg ggc act taa                                                  2367
Tyr Arg Gly Thr
785

<210> SEQ ID NO 11
<211> LENGTH: 788
<212> TYPE: PRT
<213> ORGANISM: Homo Sapiens

<400> SEQUENCE: 11
```

```
Met Arg Ala Arg Pro Arg Pro Arg Pro Leu Trp Ala Thr Val Leu Ala
1               5                   10                  15

Leu Gly Ala Leu Ala Gly Val Gly Val Gly Gly Pro Asn Ile Cys Thr
            20                  25                  30

Thr Arg Gly Val Ser Ser Cys Gln Gln Cys Leu Ala Val Ser Pro Met
            35                  40                  45

Cys Ala Trp Cys Ser Asp Glu Ala Leu Pro Leu Gly Ser Pro Arg Cys
50                  55                  60

Asp Leu Lys Glu Asn Leu Leu Lys Asp Asn Cys Ala Pro Glu Ser Ile
65                  70                  75                  80

Glu Phe Pro Val Ser Glu Ala Arg Val Leu Glu Asp Arg Pro Leu Ser
                85                  90                  95

Asp Lys Gly Ser Gly Asp Ser Ser Gln Val Thr Gln Val Ser Pro Gln
                100                 105                 110

Arg Ile Ala Leu Arg Leu Arg Pro Asp Asp Ser Lys Asn Phe Ser Ile
            115                 120                 125

Gln Val Arg Gln Val Glu Asp Tyr Pro Val Asp Ile Tyr Tyr Leu Met
            130                 135                 140

Asp Leu Ser Tyr Ser Met Lys Asp Asp Leu Trp Ser Ile Gln Asn Leu
145                 150                 155                 160

Gly Thr Lys Leu Ala Thr Gln Met Arg Lys Leu Thr Ser Asn Leu Arg
                165                 170                 175

Ile Gly Phe Gly Ala Phe Val Asp Lys Pro Val Ser Pro Tyr Met Tyr
            180                 185                 190

Ile Ser Pro Pro Glu Ala Leu Glu Asn Pro Cys Tyr Asp Met Lys Thr
            195                 200                 205

Thr Cys Leu Pro Met Phe Gly Tyr Lys His Val Leu Thr Leu Thr Asp
210                 215                 220

Gln Val Thr Arg Phe Asn Glu Glu Val Lys Lys Gln Ser Val Ser Arg
225                 230                 235                 240

Asn Arg Asp Ala Pro Glu Gly Gly Phe Asp Ala Ile Met Gln Ala Thr
                245                 250                 255

Val Cys Asp Glu Lys Ile Gly Trp Arg Asn Asp Ala Ser His Leu Leu
            260                 265                 270

Val Phe Thr Thr Asp Ala Lys Thr His Ile Ala Leu Asp Gly Arg Leu
            275                 280                 285

Ala Gly Ile Val Gln Pro Asn Asp Gly Gln Cys His Val Gly Ser Asp
290                 295                 300

Asn His Tyr Ser Ala Ser Thr Thr Met Asp Tyr Pro Ser Leu Gly Leu
305                 310                 315                 320

Met Thr Glu Lys Leu Ser Gln Lys Asn Ile Asn Leu Ile Phe Ala Val
                325                 330                 335

Thr Glu Asn Val Val Asn Leu Tyr Gln Asn Tyr Ser Glu Leu Ile Pro
            340                 345                 350

Gly Thr Thr Val Gly Val Leu Ser Met Asp Ser Ser Asn Val Leu Gln
            355                 360                 365

Leu Ile Val Asp Ala Tyr Gly Lys Ile Arg Ser Lys Val Glu Leu Glu
370                 375                 380

Val Arg Asp Leu Pro Glu Glu Leu Ser Leu Ser Phe Asn Ala Thr Cys
385                 390                 395                 400

Leu Asn Asn Glu Val Ile Pro Gly Leu Lys Ser Cys Met Gly Leu Lys
                405                 410                 415

Ile Gly Asp Thr Val Ser Phe Ser Ile Glu Ala Lys Val Arg Gly Cys
```

420             425             430
Pro Gln Glu Lys Glu Lys Ser Phe Thr Ile Lys Pro Val Gly Phe Lys
            435                 440                 445

Asp Ser Leu Ile Val Gln Val Thr Phe Asp Cys Asp Cys Ala Cys Gln
            450                 455                 460

Ala Gln Ala Glu Pro Asn Ser His Arg Cys Asn Asn Gly Asn Gly Thr
465                 470                 475                 480

Phe Glu Cys Gly Val Cys Arg Cys Gly Pro Gly Trp Leu Gly Ser Gln
                485                 490                 495

Cys Glu Cys Ser Glu Glu Asp Tyr Arg Pro Ser Gln Gln Asp Glu Cys
                500                 505                 510

Ser Pro Arg Glu Gly Gln Pro Val Cys Ser Gln Arg Gly Glu Cys Leu
            515                 520                 525

Cys Gly Gln Cys Val Cys His Ser Ser Asp Phe Gly Lys Ile Thr Gly
            530                 535                 540

Lys Tyr Cys Glu Cys Asp Asp Phe Ser Cys Val Arg Tyr Lys Gly Glu
545                 550                 555                 560

Met Cys Ser Gly His Gly Gln Cys Ser Cys Gly Asp Cys Leu Cys Asp
                565                 570                 575

Ser Asp Trp Thr Gly Tyr Tyr Cys Asn Cys Thr Thr Arg Thr Asp Thr
            580                 585                 590

Cys Met Ser Ser Asn Gly Leu Leu Cys Ser Gly Arg Gly Lys Cys Glu
            595                 600                 605

Cys Gly Ser Cys Val Cys Ile Gln Pro Gly Ser Tyr Gly Asp Thr Cys
            610                 615                 620

Glu Lys Cys Pro Thr Cys Pro Asp Ala Cys Thr Phe Lys Lys Glu Cys
625                 630                 635                 640

Val Glu Cys Lys Lys Phe Asp Arg Glu Pro Tyr Met Thr Glu Asn Thr
                645                 650                 655

Cys Asn Arg Tyr Cys Arg Asp Glu Ile Glu Ser Val Lys Glu Leu Lys
            660                 665                 670

Asp Thr Gly Lys Asp Ala Val Asn Cys Thr Tyr Lys Asn Glu Asp Asp
            675                 680                 685

Cys Val Val Arg Phe Gln Tyr Tyr Glu Asp Ser Ser Gly Lys Ser Ile
690                 695                 700

Leu Tyr Val Val Glu Glu Pro Glu Cys Pro Lys Gly Pro Asp Ile Leu
705                 710                 715                 720

Val Val Leu Leu Ser Val Met Gly Ala Ile Leu Leu Ile Gly Leu Ala
                725                 730                 735

Ala Leu Leu Ile Trp Lys Leu Leu Ile Thr Ile His Asp Arg Lys Glu
            740                 745                 750

Phe Ala Lys Phe Glu Glu Glu Arg Ala Arg Ala Lys Trp Asp Thr Ala
            755                 760                 765

Asn Asn Pro Leu Tyr Lys Glu Ala Thr Ser Thr Phe Thr Asn Ile Thr
            770                 775                 780

Tyr Arg Gly Thr
785

<210> SEQ ID NO 12
<211> LENGTH: 64
<212> TYPE: DNA
<213> ORGANISM: Synthetic DNA
<220> FEATURE:
<221> NAME/KEY: misc_feature
<222> LOCATION: (1)..(64)

<223> OTHER INFORMATION: Integrin sequence alpha V1

<400> SEQUENCE: 12
gatcccggaa ttgtttatat cttcattcaa gagatgaaga tataaacaat tcctttttg      60 gaaa                                                                    64

<210> SEQ ID NO 13
<211> LENGTH: 64
<212> TYPE: DNA
<213> ORGANISM: Synthetic DNA
<220> FEATURE:
<221> NAME/KEY: misc_feature
<222> LOCATION: (1)..(64)
<223> OTHER INFORMATION: Integrin sequence alpha V2

<400> SEQUENCE: 13
gatcccgact ttcctgtgca tttaattcaa gagattaaat gcacaggaaa gtctttttg      60 gaaa                                                                    64

<210> SEQ ID NO 14
<211> LENGTH: 63
<212> TYPE: DNA
<213> ORGANISM: Synthetic DNA
<220> FEATURE:
<221> NAME/KEY: misc_feature
<222> LOCATION: (1)..(63)
<223> OTHER INFORMATION: Integrin sequence beta 31

<400> SEQUENCE: 14
gatcccacat caatttgatc tttgcttcaa gagagcaaag atcaaattga tgttttttgg      60
aaa                                                                     63

<210> SEQ ID NO 15
<211> LENGTH: 64
<212> TYPE: DNA
<213> ORGANISM: Synthetic DNA
<220> FEATURE:
<221> NAME/KEY: misc_feature
<222> LOCATION: (1)..(64)
<223> OTHER INFORMATION: Integrin sequence beta 32

<400> SEQUENCE: 15
gatccgttgt acctataaga atgagttcaa gagactcatt cttataggta caatttttg      60 gaaa                                                                    64

<210> SEQ ID NO 16
<211> LENGTH: 1233
<212> TYPE: DNA
<213> ORGANISM: Homo sapiens
<220> FEATURE:
<221> NAME/KEY: CDS
<222> LOCATION: (1)..(1233)
<223> OTHER INFORMATION: Sequence coding for neurotensin receptor

<400> SEQUENCE: 16

```
atg gaa acc agc agc ccg cgg ccc ccg cgg ccc agc tcc aac ccg ggg        48
Met Glu Thr Ser Ser Pro Arg Pro Pro Arg Pro Ser Ser Asn Pro Gly
1               5                  10                  15 ctg agc ctg gac gcc cgg ctg ggc gtg gac act cgc ctc tgg gcc aag        96
Leu Ser Leu Asp Ala Arg Leu Gly Val Asp Thr Arg Leu Trp Ala Lys
            20                  25                  30 gtg ctg ttc acc gcg ctc tac gca ctc atc tgg gcg ctg ggc gcg gcg       144
Val Leu Phe Thr Ala Leu Tyr Ala Leu Ile Trp Ala Leu Gly Ala Ala
        35                  40                  45
```

```
ggc aat gcg ctg tcc gtg cac gtg gtg ctg aag gcg cgg gcc ggg cgc      192
Gly Asn Ala Leu Ser Val His Val Val Leu Lys Ala Arg Ala Gly Arg
 50                  55                  60 gcg ggg cgc ctg cgc cac cac gtg ctc agc ctg gcg ctc gcg ggc ctg      240
Ala Gly Arg Leu Arg His His Val Leu Ser Leu Ala Leu Ala Gly Leu
 65                  70                  75                  80 ctg ctg ctg ctg gtc ggc gtg ccg gtg gag ctc tac agc ttc gtg tgg      288
Leu Leu Leu Leu Val Gly Val Pro Val Glu Leu Tyr Ser Phe Val Trp
                 85                  90                  95 ttc cac tac ccc tgg gtc ttc ggc gac ctg ggc tgc cgc ggc tac tac      336
Phe His Tyr Pro Trp Val Phe Gly Asp Leu Gly Cys Arg Gly Tyr Tyr
            100                 105                 110 ttc gtg cac gag ctg tgc gcc tac gcc acg gtg ctg agc gtg gca ggc      384
Phe Val His Glu Leu Cys Ala Tyr Ala Thr Val Leu Ser Val Ala Gly
        115                 120                 125 ctg agc gcc gag cgc tgc cta gcc gtg tgc cag ccc ctg cgt gcc cgc      432
Leu Ser Ala Glu Arg Cys Leu Ala Val Cys Gln Pro Leu Arg Ala Arg
    130                 135                 140 agc ctg ctg acg cca cgc cgg acc cgg tgg ctg gtg gcg ctc tcg tgg      480
Ser Leu Leu Thr Pro Arg Arg Thr Arg Trp Leu Val Ala Leu Ser Trp
145                 150                 155                 160 gcc gcc tcg ctc ggc ctc gcc ctg ccc atg gcc gtc atc atg ggg cag      528
Ala Ala Ser Leu Gly Leu Ala Leu Pro Met Ala Val Ile Met Gly Gln
                165                 170                 175 aag cac gaa ctc gag acg gcg gac ggg gag ccg gag ccc gcc tcg cga      576
Lys His Glu Leu Glu Thr Ala Asp Gly Glu Pro Glu Pro Ala Ser Arg
            180                 185                 190 gtg tgc acg gtg ctg gtg agc cgc acc gcg ctc caa gtc ttt atc cag      624
Val Cys Thr Val Leu Val Ser Arg Thr Ala Leu Gln Val Phe Ile Gln
        195                 200                 205 gtg aat gtg ctg gtg tcc ttc gtg ctc ccc ttg gca cta act gct ttc      672
Val Asn Val Leu Val Ser Phe Val Leu Pro Leu Ala Leu Thr Ala Phe
    210                 215                 220 ctg aat ggg gtc aca gtg agc cac ctg ctg gcc ctc tgc tcc caa gtg      720
Leu Asn Gly Val Thr Val Ser His Leu Leu Ala Leu Cys Ser Gln Val
225                 230                 235                 240 ccg tcc act tct acc ccg ggc agc tcc acc ccc agc cgc ctg gag ctg      768
Pro Ser Thr Ser Thr Pro Gly Ser Ser Thr Pro Ser Arg Leu Glu Leu
                245                 250                 255 ctg agt gag gag ggt ctc ctc agc ttc atc gta tgg aag aag acc ttt      816
Leu Ser Glu Glu Gly Leu Leu Ser Phe Ile Val Trp Lys Lys Thr Phe
            260                 265                 270 atc cag gga ggc cag gtc agc ctg gtg aga cat aaa gac gtg cgc cgg      864
Ile Gln Gly Gly Gln Val Ser Leu Val Arg His Lys Asp Val Arg Arg
        275                 280                 285 atc cgc agc ctc cag cgc agc gtc cag gtt ctc aga gcc atc gtg gtc      912
Ile Arg Ser Leu Gln Arg Ser Val Gln Val Leu Arg Ala Ile Val Val
    290                 295                 300 atg tat gtc atc tgc tgg ctg ccg tac cat gcc cgc agg ctc atg tac      960
Met Tyr Val Ile Cys Trp Leu Pro Tyr His Ala Arg Arg Leu Met Tyr
305                 310                 315                 320 tgc tac gta cct gat gac gcg tgg act gac cca ctg tac aat ttc tac     1008
Cys Tyr Val Pro Asp Asp Ala Trp Thr Asp Pro Leu Tyr Asn Phe Tyr
                325                 330                 335 cac tac ttc tac atg gtg acc aac aca ctt ttc tac gtc agc tca gct     1056
His Tyr Phe Tyr Met Val Thr Asn Thr Leu Phe Tyr Val Ser Ser Ala
            340                 345                 350 gtg act cct ctt ctc tac aac gcc gtg tcc tcc tcc ttc aga aaa ctc     1104
Val Thr Pro Leu Leu Tyr Asn Ala Val Ser Ser Ser Phe Arg Lys Leu
```

```
                         355                   360                   365
ttc ctg gaa gcc gtc agc tcc ctg tgt gga gag cac cac ccc atg aag      1152
Phe Leu Glu Ala Val Ser Ser Leu Cys Gly Glu His His Pro Met Lys
        370                 375                 380 cgg tta ccc ccg aag ccc cag agt ccc acc cta atg gat aca gct tca      1200
Arg Leu Pro Pro Lys Pro Gln Ser Pro Thr Leu Met Asp Thr Ala Ser
385                 390                 395                 400 ggc ttt ggg gat ccc cca gaa acc cgg acc tga                          1233
Gly Phe Gly Asp Pro Pro Glu Thr Arg Thr
                405                 410

<210> SEQ ID NO 17
<211> LENGTH: 410
<212> TYPE: PRT
<213> ORGANISM: Homo sapiens

<400> SEQUENCE: 17

Met Glu Thr Ser Ser Pro Arg Pro Pro Arg Ser Ser Asn Pro Gly
1               5                   10                  15

Leu Ser Leu Asp Ala Arg Leu Gly Val Asp Thr Arg Leu Trp Ala Lys
            20                  25                  30

Val Leu Phe Thr Ala Leu Tyr Ala Leu Ile Trp Ala Leu Gly Ala Ala
        35                  40                  45

Gly Asn Ala Leu Ser Val His Val Val Leu Lys Ala Arg Ala Gly Arg
    50                  55                  60

Ala Gly Arg Leu Arg His His Val Leu Ser Leu Ala Leu Ala Gly Leu
65                  70                  75                  80

Leu Leu Leu Leu Val Gly Val Pro Val Glu Leu Tyr Ser Phe Val Trp
                85                  90                  95

Phe His Tyr Pro Trp Val Phe Gly Asp Leu Gly Cys Arg Gly Tyr Tyr
            100                 105                 110

Phe Val His Glu Leu Cys Ala Tyr Ala Thr Val Leu Ser Val Ala Gly
        115                 120                 125

Leu Ser Ala Glu Arg Cys Leu Ala Val Cys Gln Pro Leu Arg Ala Arg
    130                 135                 140

Ser Leu Leu Thr Pro Arg Arg Thr Arg Trp Leu Val Ala Leu Ser Trp
145                 150                 155                 160

Ala Ala Ser Leu Gly Leu Ala Leu Pro Met Ala Val Ile Met Gly Gln
                165                 170                 175

Lys His Glu Leu Glu Thr Ala Asp Gly Glu Pro Glu Pro Ala Ser Arg
            180                 185                 190

Val Cys Thr Val Leu Val Ser Arg Thr Ala Leu Gln Val Phe Ile Gln
        195                 200                 205

Val Asn Val Leu Val Ser Phe Val Leu Pro Leu Ala Leu Thr Ala Phe
    210                 215                 220

Leu Asn Gly Val Thr Val Ser His Leu Leu Ala Leu Cys Ser Gln Val
225                 230                 235                 240

Pro Ser Thr Ser Thr Pro Gly Ser Ser Thr Pro Ser Arg Leu Glu Leu
                245                 250                 255

Leu Ser Glu Glu Gly Leu Leu Ser Phe Ile Val Trp Lys Lys Thr Phe
            260                 265                 270

Ile Gln Gly Gly Gln Val Ser Leu Val Arg His Lys Asp Val Arg Arg
        275                 280                 285

Ile Arg Ser Leu Gln Arg Ser Val Gln Val Leu Arg Ala Ile Val Val
    290                 295                 300
```

```
Met Tyr Val Ile Cys Trp Leu Pro Tyr His Ala Arg Arg Leu Met Tyr
305                 310                 315                 320

Cys Tyr Val Pro Asp Asp Ala Trp Thr Asp Pro Leu Tyr Asn Phe Tyr
            325                 330                 335

His Tyr Phe Tyr Met Val Thr Asn Thr Leu Phe Tyr Val Ser Ser Ala
            340                 345                 350

Val Thr Pro Leu Leu Tyr Asn Ala Val Ser Ser Phe Arg Lys Leu
            355                 360                 365

Phe Leu Glu Ala Val Ser Ser Leu Cys Gly Glu His His Pro Met Lys
370                 375                 380

Arg Leu Pro Pro Lys Pro Gln Ser Pro Thr Leu Met Asp Thr Ala Ser
385                 390                 395                 400

Gly Phe Gly Asp Pro Pro Glu Thr Arg Thr
                405                 410

<210> SEQ ID NO 18
<211> LENGTH: 65
<212> TYPE: DNA
<213> ORGANISM: Synthetic DNA
<220> FEATURE:
<221> NAME/KEY: misc_feature
<222> LOCATION: (1)..(65)
<223> OTHER INFORMATION: Functional sequence of neurotensin receptor
      used for siRNA

<400> SEQUENCE: 18
gatcccgtta tgacttttgg acagtcttca agagagactg tccaaaagtc ataatttttt        60
ggaaa                                                                    65

<210> SEQ ID NO 19
<211> LENGTH: 14
<212> TYPE: PRT
<213> ORGANISM: West Nile Virus
<220> FEATURE:
<221> NAME/KEY: misc_feature
<222> LOCATION: (10)..(10)
<223> OTHER INFORMATION: Xaa can be any naturally occurring amino acid

<400> SEQUENCE: 19

Ser Ile Pro Lys Leu Glu Ile Ala Gly Xaa Phe Lys Asp Leu
1               5                   10

<210> SEQ ID NO 20
<211> LENGTH: 1520
<212> TYPE: DNA
<213> ORGANISM: West Nile Virus
<220> FEATURE:
<221> NAME/KEY: misc_feature
<222> LOCATION: (1)..(11)
<223> OTHER INFORMATION: Primer sequence
<220> FEATURE:
<221> NAME/KEY: CDS
<222> LOCATION: (12)..(1520)
<223> OTHER INFORMATION: Sequence coding for the Domain III portion of
      the Envelope
      protein

<400> SEQUENCE: 20
cggaattcag c ttc aac tgt tta gga atg agc aac agg gac ttc ctg gag        50
             Phe Asn Cys Leu Gly Met Ser Asn Arg Asp Phe Leu Glu
               1               5                   10 gga gtg tct gga gct aca tgg gtt gat ctg gta ctg gaa gga gac agt        98
Gly Val Ser Gly Ala Thr Trp Val Asp Leu Val Leu Glu Gly Asp Ser
         15                  20                  25
```

-continued

| | |
|---|---|
| tgt gtg acc ata atg tca aaa gac aag cca acc att gat gtc aaa atg<br>Cys Val Thr Ile Met Ser Lys Asp Lys Pro Thr Ile Asp Val Lys Met<br>30                 35                     40                   45 | 146 |
| atg aac atg gaa gca gct aat ctc gca gat gtg cgt agc tac tgc tac<br>Met Asn Met Glu Ala Ala Asn Leu Ala Asp Val Arg Ser Tyr Cys Tyr<br>                50                     55                     60 | 194 |
| tta gct tcg gtc agt gat ctg tca aca aaa gcc gcg tgt cca acc atg<br>Leu Ala Ser Val Ser Asp Leu Ser Thr Lys Ala Ala Cys Pro Thr Met<br>              65                     70                     75 | 242 |
| ggt gaa gct cac aac gag aaa aga gcc gac cct gcc ttt gtt tgc aag<br>Gly Glu Ala His Asn Glu Lys Arg Ala Asp Pro Ala Phe Val Cys Lys<br>80                 85                     90 | 290 |
| caa ggc gtc gta gac aga gga tgg ggg aat gga tgc gga ctg ttt gga<br>Gln Gly Val Val Asp Arg Gly Trp Gly Asn Gly Cys Gly Leu Phe Gly<br>     95                    100                   105 | 338 |
| aag ggg agc att gac aca tgt gca aag ttt gcc tgt aca acc aag gca<br>Lys Gly Ser Ile Asp Thr Cys Ala Lys Phe Ala Cys Thr Thr Lys Ala<br>110                115                 120                125 | 386 |
| act ggt tgg att atc cag aag gaa aac atc aag tac gag gtt gcc ata<br>Thr Gly Trp Ile Ile Gln Lys Glu Asn Ile Lys Tyr Glu Val Ala Ile<br>                130                 135                140 | 434 |
| ttt gtg cat ggc ccg acg act gtc gaa tca cat ggc aat tat tca aca<br>Phe Val His Gly Pro Thr Thr Val Glu Ser His Gly Asn Tyr Ser Thr<br>145                150                 155 | 482 |
| cag ata ggg gct acc caa gca gga agg ttc agc ata act cca tcg gca<br>Gln Ile Gly Ala Thr Gln Ala Gly Arg Phe Ser Ile Thr Pro Ser Ala<br>                160                 165                170 | 530 |
| cca tcc tac acg ctg aag ttg ggt gag tat ggt gag gtc aca gtt gac<br>Pro Ser Tyr Thr Leu Lys Leu Gly Glu Tyr Gly Glu Val Thr Val Asp<br>175                180                 185 | 578 |
| tgt gag cca cgg tca gga ata gac act agc gct tac tac gtt atg tca<br>Cys Glu Pro Arg Ser Gly Ile Asp Thr Ser Ala Tyr Tyr Val Met Ser<br>190                195                 200                205 | 626 |
| gtg ggt gcg aag tcc ttc ttg gtt cac cga gaa tgg ttt atg gac ctg<br>Val Gly Ala Lys Ser Phe Leu Val His Arg Glu Trp Phe Met Asp Leu<br>                210                 215                220 | 674 |
| aac ctt cca tgg agt agc gct gga agc aca acg tgg agg aac cgg gaa<br>Asn Leu Pro Trp Ser Ser Ala Gly Ser Thr Thr Trp Arg Asn Arg Glu<br>225                230                 235 | 722 |
| aca ctg atg gag ttt gaa gaa cct cat gcc acc aaa caa tct gtc gta<br>Thr Leu Met Glu Phe Glu Glu Pro His Ala Thr Lys Gln Ser Val Val<br>                240                 245                250 | 770 |
| gct cta ggg tcg cag gaa ggt gcc ttg cac caa gct ctg gct gga gca<br>Ala Leu Gly Ser Gln Glu Gly Ala Leu His Gln Ala Leu Ala Gly Ala<br>255                260                 265 | 818 |
| att cct gtt gag ttc tca agc aac act gtg aag ttg aca tca gga cat<br>Ile Pro Val Glu Phe Ser Ser Asn Thr Val Lys Leu Thr Ser Gly His<br>270                275                 280                285 | 866 |
| ctg aag tgt agg gtg aag atg gag aag ttg cag ctg aag gga aca aca<br>Leu Lys Cys Arg Val Lys Met Glu Lys Leu Gln Leu Lys Gly Thr Thr<br>                290                 295                300 | 914 |
| tat ggt gta tgc tca aaa gca ttc aaa ttc gct agg act ccc gct gac<br>Tyr Gly Val Cys Ser Lys Ala Phe Lys Phe Ala Arg Thr Pro Ala Asp<br>305                310                 315 | 962 |
| act ggt cat gga acg gtg gtg ctg gaa ctg cag tat acc gga aaa gac<br>Thr Gly His Gly Thr Val Val Leu Glu Leu Gln Tyr Thr Gly Lys Asp<br>                320                 325                330 | 1010 |
| ggg cct tgc aaa gtg ccc att tct tct gtg gct tcc ctg aac gac ctt<br>Gly Pro Cys Lys Val Pro Ile Ser Ser Val Ala Ser Leu Asn Asp Leu<br>335                340                 345 | 1058 |

```
aca ccc gtt gga agg ctg gtg act gtg aat cca ttt gtg tct gtg gct      1106
Thr Pro Val Gly Arg Leu Val Thr Val Asn Pro Phe Val Ser Val Ala
350             355                 360                 365 acg gcc aac tcg aag gtt ttg att gaa ctc gaa ccc ccg ttt agt gac      1154
Thr Ala Asn Ser Lys Val Leu Ile Glu Leu Glu Pro Pro Phe Ser Asp
        370                 375                 380 tct tac atc gtg gtg ggg aga gga gaa cag cag ata aac cac cac tgg      1202
Ser Tyr Ile Val Val Gly Arg Gly Glu Gln Gln Ile Asn His His Trp
            385                 390                 395 cac aaa tct ggg agc agt att gga aag gct ttc acc act aca ctc aga      1250
His Lys Ser Gly Ser Ser Ile Gly Lys Ala Phe Thr Thr Thr Leu Arg
                400                 405                 410 gga gct caa cga ctt gca gct ctt gga gac act gcc tgg gat ttt gga      1298
Gly Ala Gln Arg Leu Ala Ala Leu Gly Asp Thr Ala Trp Asp Phe Gly
    415                 420                 425 tca gtc gga ggg gtt ttc acc tcg gta ggg aaa gcc ata cac caa gtt      1346
Ser Val Gly Gly Val Phe Thr Ser Val Gly Lys Ala Ile His Gln Val
430             435                 440                 445 ttt gga gga gcc ttt aga tca ctc ttt gga ggg atg tcc tgg atc aca      1394
Phe Gly Gly Ala Phe Arg Ser Leu Phe Gly Gly Met Ser Trp Ile Thr
        450                 455                 460 cag ggg ctt ctg gga gct ctt ctg ctg tgg atg gga att aac gcc cgt      1442
Gln Gly Leu Leu Gly Ala Leu Leu Leu Trp Met Gly Ile Asn Ala Arg
            465                 470                 475 gac agg tca att gct atg acg ttc ctt gcg gtt gga gga gtc ttg ctc      1490
Asp Arg Ser Ile Ala Met Thr Phe Leu Ala Val Gly Gly Val Leu Leu
                480                 485                 490 ttc ctt tcg gtc aac gtc cat gct gga tcc                              1520
Phe Leu Ser Val Asn Val His Ala Gly Ser
    495                 500

<210> SEQ ID NO 21
<211> LENGTH: 503
<212> TYPE: PRT
<213> ORGANISM: West Nile Virus

<400> SEQUENCE: 21

Phe Asn Cys Leu Gly Met Ser Asn Arg Asp Phe Leu Glu Gly Val Ser
1               5                   10                  15

Gly Ala Thr Trp Val Asp Leu Val Leu Glu Gly Asp Ser Cys Val Thr
            20                  25                  30

Ile Met Ser Lys Asp Lys Pro Thr Ile Asp Val Lys Met Met Asn Met
        35                  40                  45

Glu Ala Ala Asn Leu Ala Asp Val Arg Ser Tyr Cys Tyr Leu Ala Ser
    50                  55                  60

Val Ser Asp Leu Ser Thr Lys Ala Ala Cys Pro Thr Met Gly Glu Ala
65                  70                  75                  80

His Asn Glu Lys Arg Ala Asp Pro Ala Phe Val Cys Lys Gln Gly Val
                85                  90                  95

Val Asp Arg Gly Trp Gly Asn Gly Cys Gly Leu Phe Gly Lys Gly Ser
            100                 105                 110

Ile Asp Thr Cys Ala Lys Phe Ala Cys Thr Thr Lys Ala Thr Gly Trp
        115                 120                 125

Ile Ile Gln Lys Glu Asn Ile Lys Tyr Glu Val Ala Ile Phe Val His
    130                 135                 140

Gly Pro Thr Thr Val Glu Ser His Gly Asn Tyr Ser Thr Gln Ile Gly
145                 150                 155                 160
```

```
Ala Thr Gln Ala Gly Arg Phe Ser Ile Thr Pro Ser Ala Pro Ser Tyr
                165                 170                 175

Thr Leu Lys Leu Gly Glu Tyr Gly Glu Val Thr Val Asp Cys Glu Pro
            180                 185                 190

Arg Ser Gly Ile Asp Thr Ser Ala Tyr Tyr Val Met Ser Val Gly Ala
        195                 200                 205

Lys Ser Phe Leu Val His Arg Glu Trp Phe Met Asp Leu Asn Leu Pro
    210                 215                 220

Trp Ser Ser Ala Gly Ser Thr Thr Trp Arg Asn Arg Glu Thr Leu Met
225                 230                 235                 240

Glu Phe Glu Glu Pro His Ala Thr Lys Gln Ser Val Val Ala Leu Gly
                245                 250                 255

Ser Gln Glu Gly Ala Leu His Gln Ala Leu Ala Gly Ala Ile Pro Val
            260                 265                 270

Glu Phe Ser Ser Asn Thr Val Lys Leu Thr Ser Gly His Leu Lys Cys
        275                 280                 285

Arg Val Lys Met Glu Lys Leu Gln Leu Lys Gly Thr Thr Tyr Gly Val
    290                 295                 300

Cys Ser Lys Ala Phe Lys Phe Ala Arg Thr Pro Ala Asp Thr Gly His
305                 310                 315                 320

Gly Thr Val Val Leu Glu Leu Gln Tyr Thr Gly Lys Asp Gly Pro Cys
                325                 330                 335

Lys Val Pro Ile Ser Ser Val Ala Ser Leu Asn Asp Leu Thr Pro Val
            340                 345                 350

Gly Arg Leu Val Thr Val Asn Pro Phe Val Ser Val Ala Thr Ala Asn
        355                 360                 365

Ser Lys Val Leu Ile Glu Leu Glu Pro Pro Phe Ser Asp Ser Tyr Ile
    370                 375                 380

Val Val Gly Arg Gly Glu Gln Gln Ile Asn His His Trp His Lys Ser
385                 390                 395                 400

Gly Ser Ser Ile Gly Lys Ala Phe Thr Thr Thr Leu Arg Gly Ala Gln
                405                 410                 415

Arg Leu Ala Ala Leu Gly Asp Thr Ala Trp Asp Phe Gly Ser Val Gly
            420                 425                 430

Gly Val Phe Thr Ser Val Gly Lys Ala Ile His Gln Val Phe Gly Gly
        435                 440                 445

Ala Phe Arg Ser Leu Phe Gly Gly Met Ser Trp Ile Thr Gln Gly Leu
    450                 455                 460

Leu Gly Ala Leu Leu Leu Trp Met Gly Ile Asn Ala Arg Asp Arg Ser
465                 470                 475                 480

Ile Ala Met Thr Phe Leu Ala Val Gly Gly Val Leu Leu Phe Leu Ser
                485                 490                 495

Val Asn Val His Ala Gly Ser
            500
```

MOLECULES, COMPOSITIONS, METHODS AND KITS FOR APPLICATIONS ASSOCIATED WITH FLAVIVIRUSES

CROSS-REFERENCE TO RELATED APPLICATIONS

This application is a continuation-in-part of the U.S. Utility patent application Ser. No. 10/763,450, filed on Jan. 22, 2004, now abandoned, entitled the same, which claims the benefit of the prior filing date of U.S. Provisional Patent Application No. 60/442,157, filed Jan. 22, 2003, entitled "Interaction Between Cell Receptor Protein and Flavivirus Attachment Domain/s and Uses Thereof" by Dr. Mary NG Mah Lee and Justin CHU Jang Hann, the disclosures of which are incorporated herein by reference in their entirety.

FIELD OF THE DISCLOSURE

The present disclosure relates to the field of virology, and in particular to molecules, compositions, methods and kits for applications associated with flaviviruses.

BACKGROUND OF THE DISCLOSURE

The family Flaviviridae contains at least 70 arthropod-transmitted viruses, many of which infect humans and other vertebrates. A subgroup of the Flaviviridae family, the Japanese encephalitis serocomplex, includes West Nile Virus, St. Louis encephalitis, Murray Valley encephalitis and kunjin viruses. West Nile virus, in particular, is most commonly found in Africa and the Middle East.

All flaviviruses, including West Nile Virus, St Louis encephalitis, dengue, Japanese encephalitis, yellow fever and kunjin viruses share similar size, symmetry and appearance. Despite the fact that flaviviruses may use different process to enter a host cell, such as endocytotis (described for West Nile Virus and Kunjin Virus) and direct fusion of the cell (described for dengue and Encephalitis Virus), entry of all flaviviruses into the host-cell involves an interaction between the virus and a receptor of the cell.

Several studies have shown that the viral envelope protein of flaviviruses plays a crucial role in mediating virus-host cellular receptor interaction. Based on crystallography data of tick-borne encephalitis flavivirus viral envelope protein, Rey and colleagues (1995) noted that each viral envelope protein monomer is folded into 3 distinct domains. A central domain I is the antigenic domain that carries the N-glycosylation site. Domain II of the viral envelope protein is believed to be responsible for pH-dependent fusion of the viral envelope protein to the endosomal membrane during uncoating, and domain III is important for flavivirus binding to host cells.

With reference to West Nile virus, Beasley and Barrett (2002) focused on the importance of subportions of the Domain III in West Nile virology. They identified and mapped as epitopes, portions of Domain III whose neutralization by single monoclonal antibodies may result in neutralization of the virus.

The specific interaction between flaviviruses and a vertebrate cell surface or surface membrane receptor is unknown. Without knowledge of the details of this interaction, it has proven difficult to specifically treat or prevent the disease. Therefore, there is clearly a need for the identification of the cell receptor, as well as the domain/s of the flavivirus that mediate their respective interactions.

SUMMARY OF THE DISCLOSURE

The present disclosure overcomes the problems and disadvantages of the prior art.

According to a first aspect of the present disclosure, a method for controlling a flavivirus entry into a cell is disclosed, comprising administering to the cell an agent functionally interfering with a flavivirus receptor protein, the receptor protein being an integrin.

The integrin preferably comprises integrin subunit β3 or integrin subunit αV, and most preferably is an αVβ3 integrin. The agent functionally interfering with a flavivirus receptor protein is preferably a functional blocking antibody against the integrin, or a competitive ligand for the integrin, in particular an RGD peptide or a natural ligand selected from the group consisting of fibronectin, vitronectin, laminin and chrondriotin.

According to a second aspect, a method for controlling flavivirus entry into a cell is disclosed, comprising administering to the cell an agent interfering with the expression of a flavivirus receptor protein, the receptor protein being integrin.

The agent interfering with the expression of the flavivirus receptor protein is preferably a siRNA against the integrin.

According to a third aspect, a kit for controlling flavivirus entry into a cell is disclosed, comprising: the flavivirus; an agent functionally interfering with an integrin. The flavivirus and the agent are to be used in the method disclosed herein.

Preferably, the agent functionally interfering with an integrin is a functional blocking antibody against the integrin or a competitive ligand for the integrin.

According to a fourth aspect, a further kit for controlling flavivirus entry into a cell, is disclosed, comprising: the flavivirus; and an agent interfering with expression of an integrin. The flavivirus and the agent interfering with the expression of the integrin are to be used according to the method disclosed herein.

An agent functionally interfering with an integrin may also be included in the kit disclosed herein and is to be used according to the method comprising its administration disclosed herein. The agent interfering with the expression of an integrin is preferably an SiRNA against the integrin.

According to a fifth aspect, a further method for controlling a flavivirus entry into a cell is disclosed, comprising administering to the cell an agent functionally interfering with an ATPase in the plasma membrane of the cell, preferably a functionally blocking antibody against the ATPase.

According to sixth aspect, a kit for controlling a flavivirus entry into a cell is disclosed, comprising: the flavivirus; and an agent functionally interfering with an ATPase located in the plasma membrane of the cell. The flavivirus and the agent are to be used according to the method disclosed herein.

An agent functionally interfering with an integrin and/or an agent interfering with the expression of an integrin may also be included in the kit and are to be used according to the methods comprising the respective administration herein also disclosed.

According to a seventh aspect, a method for controlling a flavivirus entry into a cell is also disclosed, which comprises administering to the cell an agent functionally interfering with a flavivirus receptor protein, the receptor protein being a neurotensin receptor.

Preferably, the agent functionally interfering with a flavivirus receptor protein is a functional blocking antibody against the neurotensin receptor, or a competitive ligand for the neurotensin receptor, in particular neurotensin.

According to an eighth aspect, a kit for controlling a flavivirus entry into a cell is disclosed, comprising: the flavivirus; and an agent functionally interfering with a neurotensin receptor in the cell. The flavivirus and the agent are to be used according to the method disclosed herein.

An agent functionally interfering with an integrin, an agent interfering with the expression of an integrin and/or an agent functionally interfering with an ATPase in the plasma membrane of the cell may also be included in the kit and are to be used according to the methods comprising the respective administration herein also disclosed.

According to a ninth aspect, a method for controlling a flavivirus entry into a cell is disclosed, the flavivirus exhibiting a flavivirus envelope protein, the flavivirus envelope protein comprising a domain III, the method comprising administering to the cell an agent functionally interfering with the domain III of the flavivirus envelope protein. Preferably the domain III of the virus comprise a portion having a sequence substantially homologous to SEQ ID NO: 20 or SEQ ID NO: 21.

According to a further aspect, a method for treating a flavivirus infection in a vertebrate is disclosed, the flavivirus exhibiting a flavivirus envelope protein, the flavivirus envelope protein comprising a domain III. The method comprises administering to the vertebrate a pharmaceutically effective amount of an agent functionally interfering with the domain III of the envelope protein of the flavivirus, able to inhibit the entry of the flavivirus in the cell.

According to a further aspect, a pharmaceutical composition for the treatment of a flavivirus infection in a vertebrate is disclosed, the flavivirus exhibiting an envelope protein comprising a domain III. The pharmaceutical composition comprises a pharmaceutically effective amount of an agent interfering with the domain III of the envelope protein able to inhibit the entry of the Flavivirus in the host cell and a pharmaceutically acceptable carrier, vehicle or auxiliary agent.

Both in the method of treating and pharmaceutical composition, the agent is preferably one of the functionally interfering agent able to inhibit the entry in the cell mentioned above. In particular, a functional blocking antibody against the domain III, preferably a polyclonal antibody, an integrin protein, preferably comprising one or both of the subunits αV and β3, or a neurotensin receptor protein or an ATPase, preferably an F-ATPase or V-ATPase, or portions thereof may be used.

According to a further aspect, a method for inducing immunity to a flavivirus in a vertebrate susceptible to the infection of the flavivirus is disclosed, the flavivirus exhibiting an envelope protein comprising a domain III. The method comprises administering to the vertebrate an immunogenic amount of a polypeptide comprising the domain III, of the envelope protein of the flavivirus, preferably comprising a portion substantially homologous to SEQ ID NQ: 20 or SEQ ID NO: 21.

According to a further aspect, a vaccine for a flavivirus, the flavivirus exhibiting an envelope protein comprising a domain III, is disclosed. The vaccine comprises as an active agent a polypeptide comprising the domain III of the envelope protein of the flavivirus.

According to a further aspect, a method for diagnosing a flavivirus infection in a vertebrate susceptible to infection by the flavivirus is disclosed, comprising contacting a sample tissue from the vertebrate, with an integrin or neurotensin protein associated with an identifier; and detecting presence or absence of a flavivirus-integrin complex or flavivirus-neurotensin complex by detecting presence of the identifier.

According to a further aspect, a kit for the diagnosis of flavivirus infection in a vertebrate, susceptible to be infected with the flavivirus, the flavivirus exhibiting an envelope protein comprising domain III is disclosed. The kit comprises at least one agent able to bind the domain III, associated with an identifier, and one or more reagents able to detect the identifier. The agent able to bind domain III and the reagents are to be used according to the diagnostic method disclosed above.

According to a further aspect, a diagnostic method to analyze a cell susceptibility to flavivirus infection, is disclosed, comprising contacting the cell with an identifier for the presence or expression of an integrin, neurotensin receptor and/or ATP-ase and detecting the presence of the identifier associated to presence or expression of an integrin, neurotensin receptor and/or ATP-ase in the cell.

According to another aspect, a kit to analyze cell susceptibility to flavivirus infection is disclosed comprising an identifier for the presence or expression of an integrin, neurotensin receptor and or ATP-ase, and a reagent able to detect the presence of the identifier; the identifier and the reagent to be used in the method disclosed above.

According to a further aspect, an isolated and purified plasma membrane polypeptide of approximately 105 KDa comprising a sequence substantially homologous to SEQ ID NO:1, SEQ ID NO:2, SEQ ID NO:3, SEQ ID NO:4, and SEQ ID NO:5 is disclosed.

In the methods, kits, composition and vaccine disclosed herein, the flavivirus is preferably a member of the Japanese encephalitis serocomplex, in particular West Nile Virus, and the vertebrate is preferably a mammal, in particular a human being.

BRIEF DESCRIPTION OF THE FIGURES

In the present disclosure, reference will be made to the enclosed Figures, which provide non-limiting examples of the inventive compositions, method and kits devised by the inventors.

FIG. 2A shows the results of a Virus Overlay Protein Binding Assay (VOPBA) performed on plasma membrane proteins extracted from Vero cells before purification under non-denaturing conditions (Lane 1) as compared to those of proteins purified from the supernatants of uninfected cells (Lane 2). Molecular size markers are indicated on the left side of the Figure by arrows.

FIG. 2B shows the results of a VOPBA performed on plasma membrane proteins extracted from N2A cells extracted before purification under non-denaturing conditions (Lane 1) as compared to those of proteins purified from the supernatants of uninfected cells (Lane 2). Molecular size markers are indicated on the left side of the Figure by arrows.

FIG. 3 shows results of a VOPBA performed on plasma membrane proteins from Vero cells and N2A cells after papain treatment (Lane 2—Vero cells; lane 4—N2A), as compared to those of the untreated cells (Lane 1—Vero cells; lane 3—N2A). Molecular size markers are indicated on the left side of the Figure by arrows.

FIG. 11A is a diagram showing the inhibition of West Nile Virus binding in Vero cells pre-incubated with functional blocking integrin antibodies. On the x-axis, the concentration of functional blocking integrin antibodies is shown. On the y-axis, the percentage reduction in virus infection is shown. INTB1=Integrin β1, INTB2=Integrin β2, INTB31=integrin beta 3, INTB32=integrin beta 3 subunit, INTB4=integrin β4, INTB5=Integrin β5, ALPHAV=Integrin αV, ALPHA V/B3=Integrin αVβ3, ALPHA5/B5=Integrin α5 β5.

FIG. 11B is a diagram showing the inhibition of West Nile Virus entry in Vero cells pre-incubated with functional blocking integrin antibodies. On the x-axis the concentration of functional blocking integrin antibodies is shown. on the y-axis the percentage reduction in virus infection is shown. INTB1=monoclonal antibodies against Integrin β1, INTB2=Integrin β2, INTB31=monoclonal antibodies against integrin beta 3 subunit purchased from Chemicon,USA, INTB32=monoclonal antibodies against integrin beta 3 subunit purchased from Santa Cruz Biotech, USA., INTB4=monoclonal antibodies against integrin β4, INTB5=monoclonal antibodies against Integrin β5, ALPHAV=monoclonal antibodies against Integrin αV, ALPHA V/B3=monoclonal antibodies against Integrin αVβ3, ALPHA5/B5=monoclonal antibodies against Integrin α5 β5.

FIG. 12 is a diagram showing the inhibition of Japanese Encephalitis Virus entry into Vero cells by functional blocking integrin antibodies. On the x-axis the integrin blocked by the specific anti integrin antibody is shown. On the y-axis the % inhibition in virus entry is shown. INTB1=monoclonal antibodies against Integrin β1; INTB2=monoclonal antibodies against Integrin β2, INTB31=monoclonal antibodies against integrin beta 3 subunit purchased from Chemicon, USA, INTB32=monoclonal antibodies against integrin beta 3 subunit purchased from Santa Cruz Biotech, USA.; INTB4=monoclonal antibodies against integrin β4; INTB5=monoclonal antibodies against Integrin β5, ALPHAV=monoclonal antibodies against Integrin αV; ALPHA V/B3=monoclonal antibodies against Integrin αVβ3; ALPHA5/B5=monoclonal antibodies against Integrin α5 β5.

FIG. 13 is a diagram showing the effect of divalent cations chelator EDTA on the entry of West Nile Virus (WNV) and Japanese Encephalitis Virus (JEV) in Vero cells. On the x-axis, the concentration of EDTA administered is shown. The y-axis shows percentage reduction of virus infection.

FIG. 14 is a diagram showing a competitive entry study of West Nile Virus (WNV) and Japanese Encephalitis Virus (JEV) with physiological ligands on Vero cells pretreated with such ligands. On the x-axis, the competitive ligands used, are shown. On the y-axis, the percentage reduction of virus infection is shown. RGE1=RGE-peptide; RGD1=RGD-peptide; FIBRO1=Fibronectin; VITRO1=Vitronectin; LAMININ 1=laminin; CHONSUL1=Chrondriotin; Heparin=Heparin.

FIG. 15 shows distribution and localization of integrin αVβ3 (A) and 105 KDa plasma membrane glycoprotein (B) in Vero cells by immunofluroscence staining.

FIG. 16 shows results of gene silencing of integrin αVβ3 subunits αV (B) and β3 (D) in Vero cells compared to control for αV (A) and β3 (C). Presence of the subunits is shown by immunofluorescence staining.

FIG. 17 is a diagram showing the effects of down-regulation of integrin αV and β3 subunits to the entry of WNV into Vero cells. On x-axis concentration of siRNA used is reported. On y-axis percentage inhibition of WNV entry is reported. INTAlpha V1=Integrin alpha V subunit region 1, INTalpha2=Integrin alpha V subunit region 2, INTB31=Integrin beta 3 subunit region 1, INTB32 =Integrin beta 3 subunit region 2, GAPDH=Glyceraldehyde-3-phosphate dehydrogenase.

FIG. 18 is a diagram showing effects of administration of antibodies against ATPases. On the x-axis, the antibodies against the respective protein are indicated. On the y-axis, the percentage reduction of virus entry is indicated. ATPB1=monoclonal antibodies against plasma membrane ATPase beta subunit, ATPB2=polyclonal antibodies against plasma membrane ATPase beta subunit, ATPA1=monoclonal antibodies against plasma membrane ATPase alpha subunit, ATPA2=polyclonal antibodies against plasma membrane ATPase alpha subunit, CALTYPE1=monoclonal antibodies against calcium dihydropyridine receptor alpha, CALTYPE2=monoclonal antibodies against calcium dihydropyridine receptor beta, VATPASE1=monoclonal antibodies against VATPase E, VATPASE2=monoclonal antibodies against VATPase.

FIG. 19 is a diagram showing blockage of WNV entry by antibodies against neurotensin receptor, in Vero cells (black column) and in A172 neuroblastoma cells (grey column). On the x-axis, the concentration of anti-neurotensin receptor is shown. The y-axis shows the percentage reduction of virus entry.

FIG. 20 is a diagram showing WNV competing binding of neurotensin receptor with its natural ligand in A172 neuroblastoma cells. On the x-axis, the concentration of neurotensin administered before incubation of the cells with WNV is shown. The y-axis shows percentage inhibition of virus entry.

DETAILED DESCRIPTION OF THE DISCLOSURE

Figure 1A:
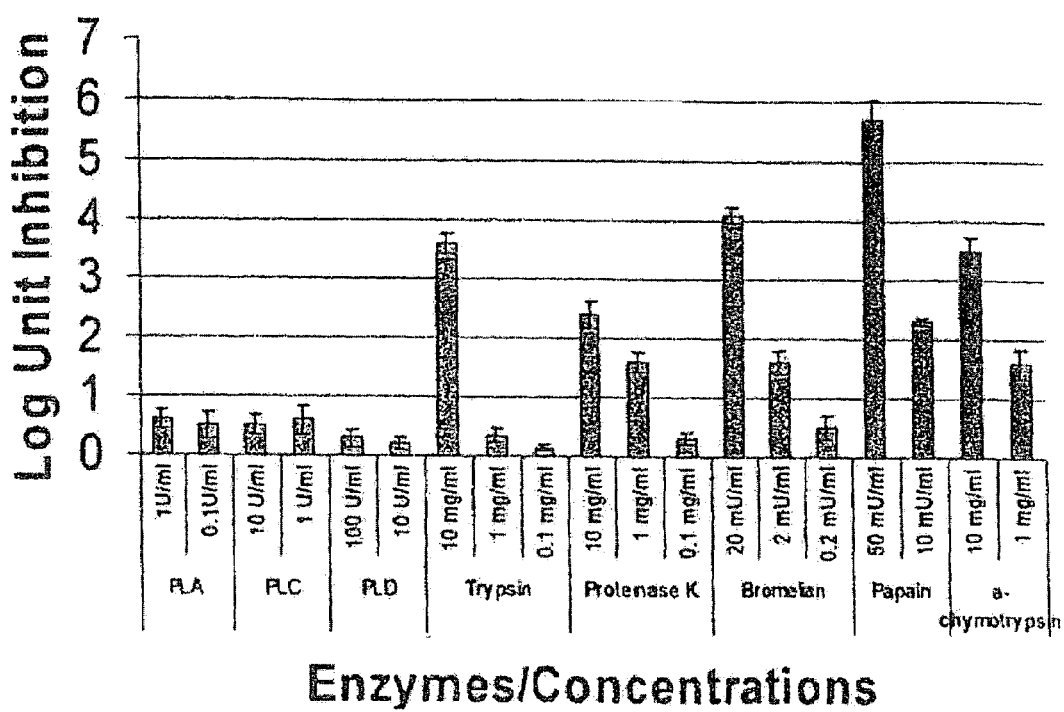
FIG. 1A shows a diagram reporting the effect of phospholipases and proteases treatment on West Nile virus binding molecules present on the surface of intact Vero cells. The y-axis shows the inhibition of West Nile virus entry expressed as the number of log unit inhibition with respect to untreated samples. On the x-axis, the dosage of the substance administered is reported. PLA=Phospholipase $A_2$, PLC=Phospholipase C, PLD=Phospholipase D

A method for controlling the entry of a flavivirus into a cell is described. In particular, the method is based on the identification of integrins as receptors which mediate entry of the flavivirus into the cell.

In their quality as flavivirus receptors, integrins have been found to surprisingly mediate entry of a wide number of flaviviruses using diverse processes to enter the host cell, such as endocytosis and cell fusion. In particular, integrins have been shown to mediate the entry in the cell of flaviviruses belonging to the Japanese Encephalitis Serocomplex, in particular West Nile Virus, St. Louis encephalitis, Murray Valley encephalitis, as well as the entry of other flaviviruses such as dengue and kunjin.

Additionally, the activity of integrins as flavivirus receptors disclosed herein applies to a wide range of cell systems, including brain cells, and to a wide number of organisms, including vertebrates and human beings.

Integrins have been identified to be flavivirus receptors through a series of experiments extensively described in the examples that follow.

In particular, in a first series of experiments, described in the examples 1 to 9, the receptor has been first identified as a protease sensitive glycoprotein with complex N-linked sugars containing α-mannose residues, localized on the cell membrane. In particular, a 105-KDa glycoprotein exhibiting all these properties has been isolated (see example 2).

The experiments have been carried out on Vero cells and N2A cells. Both are cells lines highly permissive for West Nile Virus, which has been used as a model for flaviviruses. Vero cells is a Green Monkey cell line and has been used as a cell system to isolate the receptor for WNV. N2A is a mouse derived brain cell line, which has been used as an alternative to human brain cells, since West Nile virus has shown tropism to brain cells during infection in mammals.

West Nile virus, in particular the Sarafend strain, has been used in these experiments. West Nile Virus has been used as a representative of the flavivirus and in particular of the flavivirus belonging to the Japanese Encephalitis Serocomplex group. Other flaviviruses of the Japanese Encephalitis Serocomplex group, including kunjin ,as well as flaviviruses not belonging to such group, such as dengue, were also used to extend the analysis on the integrins' activity as flavivirus receptors to the entire flavivirus family.

The experiments extensively described in examples 10 and 11 confirm the 105 KDa glycoprotein's ability to act as a receptor for West Nile and other flaviviruses, in particular those of the Japanese Encephalitis serocomplex group, including St. Louis encephalitis, Murray Valley Encephalitis, as well as dengue and kunjin. In particular in view of those results, a significant receptor activity for any flaviviruses belonging to the flavivirus family is expected. In particular, receptor activity for the flavivirus having an E protein substantially homologous to the E protein of a member of the Japanese Serocomplex group, such as yellow fever and tick borne, is expected.

Further analysis of the 105 KDa protein has confirmed location of the receptor on the membrane (example 12) and the fact that the receptor is an integrin (example 13). In particular, further experiments assaying flavivirus entry inhibition, sequencing of the 105 KDa protein and Virus Overlay Protein Binding Assays, described in examples 11 to 17, have identified the 105 KDa protein as a αVβ3 integrin and a significant receptor activity of integrins comprising subunits other than αV and β3.

In particular, experiments reported in examples 13 to 17 showed a significant ability of integrins to act as receptors for flaviviruses wherein subunits have an independent ability to act as a receptor for the virus. In particular, a particularly significant ability of integrin subunits αV and β3 to act as a receptor was observed. However a better efficiency is obtained when both subunits are present.

These results have been obtained in Vero cells and N2A cells. However, since integrins are expressed in most types of cells, including brain cells of vertebrates, and since flaviviruses, and in particular WNV, have been shown to afflict a range of other mammals such as horses and humans, as well as other vertebrates such as birds, the scope of these results can be extended to these other systems as well.

The administration of an agent able to functionally interfere with the integrin has been shown to affect the flavivirus entry in the host cell (see examples 1-22).

Therefore, the present disclosure shows that administration of an agent that functionally interferes with integrin affects flavivirus entry in the host cell. In particular, agents able to interfere with the functionality of the attachment domain of the integrin are functionally interfering agents of this disclosure.

Functionally interfering agents can enhance or inhibit the integrin functionality. In particular, interfering agents able to functionally inhibit integrins, such as functional blocking antibodies and competitive ligands, are considered to be a functionally interfering agent able to inhibit the entry of flavivirus.

Preferably, the functionally blocking antibodies are polyclonal antibodies, in particular against the 105 KDa protein, the integrin subunits $\alpha V$, $\beta 3$, $\alpha V \beta 3$ or $\alpha V \beta 5$.

The competitive ligand can be a natural ligand, such as for example fibronecitin, vitronectin or laminin, or a synthetic ligand, for example RGD peptide or chemically synthesized peptides that are complementary to the binding region in the integrin, which ligand can be identified and manufactured by a person skilled in the art, based on the information provided in the present application.

Proteases such as papain, glycosidases, lectins, and cycloheximide are also considered functionally interfering agents able to inhibit the integrin functionality.

These functionally interfering agents were used at a range of concentrations that are non-cytotoxic to the cells used in our system. In particular, functionally inhibitors of the integrin can be administered at following amounts: papain 10-50 mUnit/ml; Lectin and in particular Concanavalin-A phytohemagglutinin) 100-1000 µg/ml; cycloheximide about 100 µg/ml; Endoglycosidase 10-100 mUNIT/ml; O-glycosidase 0.1-1 mUNIT/ml; mannosidase 100-1000 µg/ml; Fucosidase 10-100 mUNIT/ml.

With reference to competitive ligands, effective concentrations that will block the entry of West Nile virus will be in the ranges that follows: RGE peptide: 0.01-30 µg/ml;RGD peptide: 0.01-30 µg/ml;Fibronectin: 0.01-40 µg/ml; Vitronectin: 0.01-40 µg/ml;Laminin: 0.01-40 µg/m; Chrondriotin sulphate: 0.01-40 µg/ml;Heparin: 0.01-40 µg/ml. These ligands can be administered before an infection occurs or during an infection to block the entry of the subsequent newly produced virus progeny from entry. The ligand needs to be incubated with the cells for at least 30 min for effective binding to the cells and can be present for more than 1 hr. The temperature for incubating the ligand with cells can be in the range of about 4° C. to 40° C.

With reference to the antibodies gainst integrin subunits, the effective concentrations of the functional blocking integrin (all the integrin used) antibodies that will block the entry of West Nile virus will be in the range of about 0.025 µg/ml-40 µg/ml. These antibodies can be administered before an infection occurs or during an infection to block the entry of the subsequent newly produced virus progeny from entry. The antibodies are preferably incubated with the cells for at least 10 min for effective binding to the cells and can be present for more than 1 hr. The temperature for incubating the antibodies with cells can be in the range of about 4° C. to 40° C.

The present disclosure also shows that agents interfering with the expression of the integrin are able to affect the entry of the flavivirus into the host cell.

In particular, interference with the expression of the integrin may result in inhibition or enhancement of such expression. For example, a silencer or preferably a short interfering RNA is suitable for use with the present invention and allows flavivirus activity to be inhibited. Other agents interfering with the expression of the integrin are identifiable by a person skilled in the art based on the information provided in the present application.

The present disclosure shows that entry of flavivirus is also affected by administration of an agent functionally interfering with the functionality of an ATPase in the cell. In particular the ATPases as intended herein include but are not limited to the plasma membrane associated ATPases (known as F-ATPases) and the vacuolar ATPases that can be localized to the plasma membrane as well as the membrane of endocytic vesicles and lysosomes.

Functionally interfering agents can enhance or inhibit the ATP-ase functionality. In particular, interfering agents able to functionally inhibit the ATPases, such as functional blocking antibodies and competitive ligands, are examples of functionally interfering agents able to inhibit the entry of flavivirus.

Preferably, the functionally blocking antibodies are monoclonal and polyclonal antibodies in particular against extracellular subunits of ATPases (plasma membrane) as well as V-ATPases. It has been shown that such antibodies are particularly effective in inhibiting flavivirus entry (See Example 19).

The competitive ligand can be a natural ligand or a synthetic ligand, such as chemically synthesized peptides that are complementary to binding regions in the ATPase, which can be identified and manufactured by a person skilled in the art based on the information provided in the present application.

Administration of an agent that functionally interferes with a neurotensin receptor affects flavivirus entry in the host cell is dislcosed. Neurotensin receptors are present in the brain and gastrointestinal tract and are involved in neurotransmission.

Functionally interfering agents can enhance or inhibit the neurotensin functionality. In particular, interfering agents able to functionally inhibit a neurotensin receptor, such as functional blocking antibodies and competitive ligands, are examples of functionally interfering agents able to inhibit the entry of flavivirus Preferably, the functionally blocking antibodies are monoclonal and polyclonal antibodies, directed, in particular, against the extracellular portion of the neurotensin receptor.

More specifically, the inventors show that, in particular competitive natural ligands such as neurotensin and antibodies against the receptor, inhibit the entry of the virus (See Examples 20-21). Other competitive ligands known to compete with neurotensin for neurotensin receptor can used. For example, Neuromedin N, 8 bromo-cAMP, IBMX and forskolin are competitive ligands competing with neurotensin for the neurotensin receptor (Shi & Bunney 1992), which are expected to inhibit the entry of the virus.

The competitive ligand can also be a synthetic ligand, such as chemically synthesized peptides that are complementary to the binding region in the neurotensin receptor. Also in this case, ligands can be identified and manufactured by a person skilled in the art based on the information provided in the present application.

The present disclosure provides a further method for interefering with flavivirus entry. According to this further method, domain III in the envelope protein of the flavivirus has been found to bind the flavivirus receptor in the host cell.

Experiments of competitive binding between the domain III of the virus envelope protein, expressed in soluble form and West Nile and dengue viruses, extensively reported in Example 22, show that the domain III of the envelope protein is the attachment domain of the envelope protein for the receptor protein in the cell.

Therefore, administration of an agent that functionally interferes with domain III of the envelope protein also affects flavivirus entry in the host cell. The agent functionally interfering with the domain III activity can enhance or inhibit the functionality of domain III. Preferably, the functionally interfering agent is able to inhibit the functionality of domain III. In particular, agents such as a competitive ligand of domain III or an antibody against domain III, are functionally interfering agent able to inhibit the functionality of the domain III.

In particular, the competitive ligand can be a competitive natural ligand of domain III such as an integrin, and more specifically an integrin comprising at least one of $\alpha V$ and $\beta 3$ integrin subunits, preferably an integrin comprising both subunits $\alpha V$ and $\beta 3$. The competitive natural ligand can be also a neurotensin receptor or an ATPase, preferably an F-ATPase or V-ATPase or a molecule substantially homologous thereto. The competitive ligand can also be a synthetic ligand, such as chemically synthesized peptides that are complementary to domain III or the binding region in the integrin or neurotensin or ATPase, which can be identified and manufactured by a person skilled in the art based on the information provided in the present application. The antibody against the domain III is preferably a polyclonal antibody against domain III, most preferably a functional blocking polyclonal antibody against domain III.

An antibody against a membrane 105 KDa polypeptide having a sequence substantially homologous to SEQ ID NO:1, SEQ ID NO:2, SEQ ID NO:3, SEQ ID NO: 4 and SEQ ID NO:5 is also here disclosed.

A kit of parts for controlling and assaying entry of the flavivirus in a cell is also disclosed, comprising the flavivirus and at least one among the functionally interfering agents here described and/or agents interfering with the integrin expression.

The flavivirus and the at least one among the functionally interfering agents are comprised in the kit independently in one or more compositions wherein each is in a composition together with a suitable vehicle carrier or auxiliary agent.

In particular, the flavivirus and functionally interfering agents or expression-interfering agents interfering with the expression can be provided in the kits, with suitable instructions and other necessary reagents, in order to perform the methods here disclosed. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

Further details concerning the identification of the suitable carrier agent or auxiliary agent of the compositions, and generally manufacturing and packaging of the kit, can be identified by the person skilled in the art upon reading of the present disclosure.

A method for inducing immunity to a flavivirus in a vertebrate susceptible to infection to the flavivirus is also disclosed. In particular, the method is effective for immunizing against infection to a flavivirus having an envelope protein comprising the domain III and comprises administering an immunogenic effective amount of an amino acidic molecule comprising a domain III of the envelope protein of the flavivirus. Preferably, the domain III comprises a portion having a sequence substantially homologous to SEQ ID NO: 20 or SEQ ID NO: 21.

Accordingly, also a vaccine for flavivirus infection is disclosed, comprising, as an active agent, a polypeptide comprising domain III of the envelope protein of the flavivirus. When the flavivirus is West Nile Virus, the polypeptide preferably comprise a portion having a sequence substantially homologous to SEQ ID NO: 20 or SEQ ID NO: 21.

Also a DNA vaccine comprising as an active agent a vector wherein the domain III sequence has been disclosed, in particular an adenovirus replication defective vector is expected to be effective, as well as a chimera peptide vaccine against a flavivirus comprising as an active agent a chemically synthesized peptide of the flavivirus envelope domain III region, in particular when the flavivirus is West Nile Virus or dengue.

The vaccine may advantageously contain other components, such as adjuvant, attenuated flavivirus, killed flavivirus or subunits thereof, and/or other immunogenic molecules against the flavivirus, in particular against the envelope protein of the flavivirus. The manufacturing process and components to be included in the vaccine are known as such to the person skilled in the art and will not be disclosed here in detail.

Also a method of treating a flavivirus infection in a vertebrate in need of such a treatment, in particular humans, is disclosed. This method comprises administering to a subject in need of such treatment an immunologically effective dose of the vaccine here disclosed.

The vaccine disclosed herein may be administered by any suitable route, which delivers an immunoprotective amount of the domain III and other immunogenic components of the vaccine to the subject. Routes of administration of the vaccine, such as, for example, parenteral route, intramuscular route or deep subcutaneous route, are identifiable by a person skilled in the art. Other modes of administration may also be employed, where desired, such as oral administration or via other parenteral routes, i.e., intradermally, intranasally, or intravenously.

A person skilled in the art can determine the appropriate immunoprotective and non-toxic dose of such vaccine to be administered. The appropriate immunoprotective and non-toxic amount of the active agents in the vaccine are in the range of the effective amounts of antigen in conventional vaccines including active agents. The specific dose level for a specific patient will be determined with reference to the age, sex, and general health of the patient. Also, the synergistic effect with other drugs administered as well as the diet of the patient, the time and route of administration, and the degree of protection to be sought, will be taken in consideration to determine the appropriate immunoprotective dose for the patient. The administration can be repeated at suitable intervals, if necessary.

A method for treating a flavivirus infection in a vertebrate, when the flavivirus exhibits a flavivirus envelope protein comprising a domain III is also disclosed. A pharmaceutically effective amount of an agent functionally interfering with the domain III of the envelope protein of the flavivirus is administered.

Also a pharmaceutical composition is disclosed herein, for treatment of a flavivirus infection in a vertebrate when the flavivirus exhibits an envelope protein comprising domain III. The pharmaceutical composition disclosed comprises a pharmaceutically effective amount of an agent interfering with domain III of the envelope protein and a pharmaceutically acceptable carrier, vehicle or auxiliary agent.

The agent functionally interfering with domain III of the flavivirus in the methods of treatment and pharmaceutical composition can be any agent functionally interfering with domain III, able to inhibit the entry of the flavivirus in the cell herein disclosed. Preferably, the agent is a functional blocking antibody against domain III, most preferably a functional blocking polyclonal antibody against domain III, in particular murine antibodies. Also preferred is a competitive ligand of domain III, which can be a competitive natural ligand such as an integrin including at least one of subunits αV or β3, most preferably the integrin αVβ3, a neurotensin receptor or an ATPase, preferably a F-ATPase or a V-ATPase. Preferred agents functionally interfering with domain III, able to inhibit virus entry also include competitive synthetic ligands, such as chemically synthesized peptides that are complementary to domain III or the binding region on the integrin αV β3, neurotensin receptor and/or F-ATPase or V-ATPase.

A pharmaceutically acceptable carrier, vehicle or auxiliary agent as used herein can be identified by a person skilled in the art as suited to the particular agent and to the particular dosage form desired. The composition may be prepared in various forms for administration, identifiable by a person skilled in the art.

The agent functionally interfering with domain III as described above may be administered using any amount and any route of administration effective for attenuating infectivity of the virus. Thus, the expression "pharmaceutically effective amount", as used herein, refers to a nontoxic but sufficient amount of the antiviral agent to provide the desired treatment of viral infection.

The agent described herein may be administered as such, or in the form of a precursor from which the active agent can be derived. Such a precursor is a derivative of a compound described herein, the pharmacologic action of which results from the conversion by chemical or metabolic processes in vivo to the active compound. Such a precursor may be prepared according to procedures well known in the field of medicinal chemistry and pharmaceutical formulation science for each agent described herein.

The administration of the agent functionally interfering with domain III may be performed by routes identifiable by the person skilled in the art depending on the agent administered and the nature and severity of the infection to be treated.

The exact amount required for the treatment of a subject, and route of administration of such amount will vary from subject to subject, depending on the species, age, and general condition of the individual patient, the severity of the infection, the particular antiviral agent and its mode of administration, etc.

In view of the inhibitory effect on flavivirus infection, the agent interfering with domain III of the flavivirus envelope protein will be useful not only for therapeutic treatment of virus infection, but also for virus infection prophylaxis.

A method for diagnosing a flavivirus infection in a vertebrate susceptible to infection by the flavivirus is also disclosed. The method comprises: contacting a sample tissue from the vertebrate with an agent able to bind domain III of the envelope protein of the virus, in particular an antibody against domain III, a ligand of domain III or a molecule substantially homologous thereto, associated with an identifier; and detecting presence or absence of a flavivirus-integrin complex or flavivirus-neurotensin complex by detecting presence of the identifier. Alternatively, the identifier can be associated with the sample tissue. Preferably, the antibody against domain III are polyclonal antibodies, and the ligand is a competitive natural ligand such as integrin, a neurotensin receptor protein or an ATPase or a competitive synthetic ligand.

For example, a plasma membrane of the sample tissue or cell line can be extracted, for example with the protocol given in the reference (Chu and Ng, 2003). The extracted plasma membrane can be coated onto 96 well plates and Cy5-labelled WNV particles can be added for the interaction. After extensive washing to remove background noise, the presence of WNV particles binding to the receptor molecules can be detected, for example by fluorescence in an ELISA plate reader.

A kit for the diagnosis of a flavivirus infection comprising at least one of the above agents able to bind domain III, optionally associated or to be associated with an identifier, and one or more reagents able to detect the identifier, is also disclosed, wherein the agent able to bind domain III and the reagents are used according to the diagnostic method herein disclosed.

The agent able to bind domain III and the one or more reagents able to detect the identifier, can be independently included in one or more compositions wherein they are comprised together with a suitable vehicle carrier or auxiliary agent. The identifier can also be included in such compositions or in a separate composition to be associated with the agent able to bind the domain or with the cell or sample to be tested.

The identifier and the reagent able to detect the identifier, are identifiable by a person skilled in the art. Other compositions and/or components that may be suitably included in the kit and are also identifiable by a person skilled in the art.

Also a diagnostic method to detect whether a sample tissue or cell line is susceptible to flavivirus infection is disclosed, comprising contacting a cell with an identifier for the presence or expression of an integrin, neurotensin receptor and or ATPase to be associated with the presence or expression of an integrin, neurotensin receptor and or ATPase, and detecting the presence of the identifier associated to presence or expression of an integrin, neurotensin receptor and/or ATP-ase in the cell.

For example, an approach to detect whether a sample tissue or cell line is susceptible to flavivirus infection can be that of detecting the presence or expression of integrin alphaV beta 3 or neurotensin by staining these cells with antibodies against these receptors and detect for fluorescence. An exemplary alternative can be to use real-time quantitative PCR to detect the presence of mRNA for integrin or neurotensin receptor in the tissue sample or cells.

A diagnostic kit to detect whether a sample tissue or cell line is susceptible to flavivirus infection is also disclosed, comprising an identifier for the presence or expression of an integrin, neurotensin receptor and or ATP-ase, and a reagent able to detect the presence of the identifier. The identifier and the reagent able to detect the presence of the identifier are to be used in the method to detect whether a sample tissue or cell line is susceptible to flavivirus infection here disclosed.

The identifier and the reagent can be included in one or more compositions where the identifier and/or the reagent are included with a suitable vehicle, carrier or auxiliary agent.

In both of the diagnostic kits herein disclosed, the agents and identifier reagents can be provided in the kits, with suitable instructions and other necessary reagents, in order to perform the methods here disclosed. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

Further details concerning the identification of the suitable carrier agent or auxiliary agent of the compositions, and generally manufacturing and packaging of the kit, can be identified by the person skilled in the art upon reading of the present disclosure.

Methods, kits, vaccine and pharmaceutical compositions disclosed herein are particularly used when the flavivirus is a member of the Japanese encephalitis serocomplex, preferably West Nile Virus, Japanese Encephalitis virus, West Valley or a virus such as Dengue and Kunjin virus. Preferably, the vertebrate is a mammal, and, in particular, a human being.

A person skilled in the art can identify modalities, dosages, timing of administration of the methods herein disclosed as well as vehicle carrier auxiliary agents, relative concentration, formulation and modalities of administration of the compositions herein disclosed.

As used herein, the term "antibody" may be a polyclonal or monoclonal antibody unless differently specified. The relevant preparation, is identifiable by a person skilled in the art upon reading of the present disclosure. In the specific examples given, murine polyclonal antibodies were used. Monoclonal antibodies may be obtained by any technique that provides for the production of antibody molecules by continuous cell line culture. These techniques are well known and routinely used in academic and industrial settings. Some techniques include but are not limited to the hybridoma technique of Kohler and Milstein, (1975, Nature 256:495-497; and U.S. Pat. No. 4,376,110), the human B-cell hybridoma technique (Kosbor et al., 1983, Immunology Today 4:72; Cole et al., 1983, Proc. Natl Acad. Sci. USA 80:2026-2030), and the EBV-hybridoma technique (Cole et al., 1985, Monoclonal Antibodies And Cancer Therapy, Alen R. Liss, Inc., pp. 77-96).

Antibody fragments, which retain the ability to recognize the antigen of interest, are included as well.

The antibodies are produced using techniques known to those skilled in the art and disclosed, for example, in immunization techniques in vivo or in vitro. These techniques are well known and routinely used in academic and industrial settings.

As used herein, the terms "polypeptide", and "protein" refer to a polymer of amino acid residues with no limitation concerning a minimum length of the product. The definition encompasses peptides, oligopeptides, dimers, multimers, and the like, full-length proteins and fragments thereof. The terms also include polypeptides subjected to post-expression modifications such as, for example, glycosylation, acetylation, phosphorylation and the like. Additionally, the term "polypeptide" refers also to a modified protein including protein comprising deliberate or accidental modifications of the original sequence, such as deletions, additions and substitutions, so long as the protein maintains the desired activity.

As used herein, the term "homology" refers to the percent similarity between two polynucleotide or two polypeptide moieties. Two DNA, or two polypeptide, sequences, are "substantially homologous" to each other when the sequences exhibit at least about 50%, preferably at least about 70%, more preferably at least about 80%-85%, preferably at least about 90%, and most preferably at least about 95%-98% sequence similarity over a defined length of the molecules. As used herein, substantially homologous also refers to sequences showing complete identity to the specified DNA or polypeptide sequence.

As used herein the term "agent functionally interfering" refers to any kind of interference with the functionality of the molecule, which results in a different functionality of the molecule compared with the functionality registered in absence of the agent. This includes enhancing and inhibiting the functionality of the molecule. Examples of interference with the functionality of the molecule may be obtained include but are not limited to binding the molecule, interference by steric hindrance with the molecule, modify functional components of the molecule, interfere with the expression of the molecule.

The following examples are provided to describe the invention in further detail. These examples, which set forth a preferred mode presently contemplated for carrying out the invention, are intended to illustrate and not to limit the invention.

EXAMPLES

General materials and methods used throughout the experiments will first be presented.

Maintenance of Cell Lines

Vero cells (Green monkey kidney) were grown in Medium 199 (M199) containing 10% inactivated fetal calf serum (FCS). Murine neuroblastoma (N2A) cells were maintained in Dulbecco's modified Eagle's medium supplemented with 10% FCS. Polarized Vero C1008 cells were grown on 0.4 µm porous support membrane insert immersed in M199 supplemented with 10% FCS. The polarity of the cell monolayers was monitored by measuring the transepithelial electrical resistance with millicell-ERS apparatus. The net resistance of the confluent cell monolayers was maintained at 50-70 $\Omega.cm^2$ as calculated based on Blau & Compans (1995). Neurons are isolated from mice and maintained in Dulbecco's modified Eagle's medium supplemented with 10% FCS.

Virus Growth & Purification

Vero cells were used to propagate a Flavivirus, West Nile (Sarafend) virus throughout this study. Confluent monolayers of Vero cells were infected with West Nile virus at a multiplicity of infection (MOI) of 10 PFU/ml. At 24 hr post infection (p.i.), the supernatant was harvested by centrifugation at 5000 rpm for 10 minutes. West Nile viruses were then concentrated and partially purified by centrifugal filter device at 2000 rpm for 2 hours. The partially purified viruses were then applied to a 5 ml 25% sucrose cushion for further purification. Sucrose gradient was centrifuged at 25,000 rpm for 2.5 hours at 4° C. in a SW55 rotor. Finally, the purified virus pellet was re-suspended in TNE buffer (50 mM Tris-HCl, 100 mM NaCl, 1 mM EDTA). The re-suspended virus was aliquoted, snapped frozen and stored at −80° C. The titer of the purified virus preparation was determined by plaque assay on Vero cells and was found to be $9 \times 10^8 - 5 \times 10^9$ PFU/ml. As a control, supernatant of uninfected Vero cells were processed as described above. A similar method was used to propagate Kunjin virus cells, a closely related virus in the same subgroup, and Dengue virus cells, another flavivirus.

Antibodies and Reagents

The antibody for West Nile virus envelope (E) protein was a monospecific polyclonal antibody raised in rabbit. The secondary antibody conjugated to Texas Red (TR) was purchased. Fifteen-nanometer Protein-A colloidal gold was also purchased for antibody detection.

Polyclonal antibodies against the 105 kDa and WNV envelope DIII protein have been produced according to the following. The 105-kDa plasma membrane protein (from Vero cells) or WNV envelope DIII protein was excised from the SDS-10% PAGE gels, homogenized, and incubated with ImmunEasy mouse adjuvant (Qiagen, USA) at a concentration 3 μg of protein per 30 μl of adjuvant. The antigen-adjuvant mixture was used to immunize BALB/c mice five times subcutaneously at 14-day intervals. Mouse sera were collected 12 days after the last booster. Mouse sera were purified using Econo-Pac serum IgG purification kits (Bio-Rad, USA) and dialyzed overnight with PBS. The purified immunoglobulins were stored at −20° C. Sera were tested by Western blotting detection for the presence and specificity of antibody against the 105-kDa membrane protein or DIII protein.

Cell Membrane Protein Preparation

The plasma membrane proteins are prepared as described by Martinez-Barrage and del Angel (2001) and Salas-Benito and del Angel (1997). The integrity of extracted membrane proteins was determined by electron microscopy as described by Atkinson and Summers (1971). The concentration of the protein was determined by Bradford assay with bovine serum albumin (BSA) as the standard. Approximately 800 μg of proteins were obtained. The membrane protein preparation was aliquoted and stored at −20° C.

Example 1

Protease, Phospholipase, Glycosidase and Lectin Treatment of Cells

To determine the biochemical components (e.g. lipids, proteins or carbohydrates) of West Nile virus receptor molecules on the surface of Vero cells, cells were pretreated with a panel of enzymes or chemicals that would destroy the individual membrane components.

Cell monolayers (Vero cells or N2A) of approximately $5\times10^6$ cells were washed twice with phosphate buffer saline (PBS) before enzyme treatment. Cell monolayers were incubated with the proteases and phospholipases, glycosidases and lectins (as listed below) in PBS at a pH of 7.0 for 45 min at 25° C. After treatment, cell monolayers were washed twice with PBS supplemented with 2% FCS to remove the enzymes. Cell monolayers were then incubated with West Nile virus (MOI=10) at 37° C. for 1 hour. Excess virus particles were inactivated with sodium citrate buffer (pH 2.8) for 10 minutes and the cell monolayer washed twice with PBS. Vero cells were then incubated at 37° C. for 12 hours. At 12 hours p.i., virus titers from the treated samples were determined by plaque assays. Three independent experiments were conducted for each set of enzymes used.

The enzymes used were; Proteases: Proteinase K (EC 3.4.21.64) from *Tritirachium album*, concentration of 10 μg/ml, 1 μg/ml & 0.1 μg/ml; α-chymotrypsin (EC 3.4.21.1) from bovine pancreas, concentration of 10 μg/ml & 1 μg/ml; trypsin (EC 3.4.21.4) from bovine pancreas, concentration of 10 μg/ml, 1 μg/ml & 0.1 μg/ml; Bromelain (EC 3.4.22.32) from pineapple stem, concentration of 20 mUnit/ml, 2 mUnit/ml & 0.2 mUnit/ml; Papain (EC 3.4.22.2) from *Carica papaya*, concentration of 50 mUnit/ml & 10 mUnit/ml. Phospholipases: Phospholipase $A_2$ (EC 3.1.1.4) from bovine pancreas, concentration of 1 UNIT/ml & 0.1 UNIT/ml; Phospholipase C (EC 3.1.1.4.3) from *Clostridium perfringes*, concentration of 10 UNIT/ml & 1 UNIT/ml; Phospholipase D (EC 3.1.4.4) from peanut, concentration of 100 UNIT/ml & 10 UNIT/ml; Glycosidases: Endoglycosidase H (EC 3.2.1.96) from *Streptomyces plicatus*, concentration of 100 mUNIT/ml & 10 mUNIT/ml; O-glycosidase (EC3.2.1.97) from *Diploccus pneumoniae*, concentration of 1 mUNIT/ml & 0.1 mUNIT/ml; α-mannosidase (EC 3.2.1.24) from almonds, concentration of 1000 μ/ml, 100 μg/ml & 10 μg/ml; α-Fucosidase (EC 3.2.1.11) from almond meal, concentration of 100 mUNIT/ml & 10 mUNIT/ml; Heparinase I (EC 4.2.2.7) and Heparinase III (EC 4.2.2.8) from *Flavobacterium heparinum*, concentration of 1 UNIT/ml & 0.1 UNIT/ml;. Lectins: Concanavalin-A from Jack bean, wheat germ agglutinin from *Triticum vulgaris*, phytohemagglutinin from *Phaseolus* spp., concentration of 1000 μg/ml & 100 μg/ml ; Sodium periodate concentration of 1 mM & 0.1 mM. Cell viability after enzyme treatment was assessed by Trypan blue staining and observation under phase contrast microscope BX 60.

Treatment with glycosidases, sodium periodate and lectins was made to investigate possible involvement of carbohydrate moieties on the plasma membrane for West Nile Virus. In particular, lectins (highly specific carbohydrate binding molecules) are widely used to determine the nature of carbohydrates involved in ligand-receptor interaction (Liener et al., 1986). Vero cells were then incubated with lectins such as Wheat germ agglutinin (which binds to GlcNacβ1-4 on N-linked glycans), concanavalin A (which binds to α-linked terminal mannose residues on N-linked glycans) and phytohemagglutinin (which binds oligosaccharides) to assess their effects on West Nile virus entry.

The enzymes or chemicals were used at concentrations known to be effective in reducing the entry of other known viruses (Borrow and Oldstone, 1992; Ramos-Castaneda et al., 1997; Salas-Benito and del Angel, 1997; Martinez-Barragan and del Angel, 2001). Results are expressed as the number of log unit inhibition with respect to untreated samples. At the same time, cell viability after treatments was also assessed by Trypan blue exclusion method. The number of viable cells after treatments was not significantly different from untreated (control) numbers.

Figure 1B:
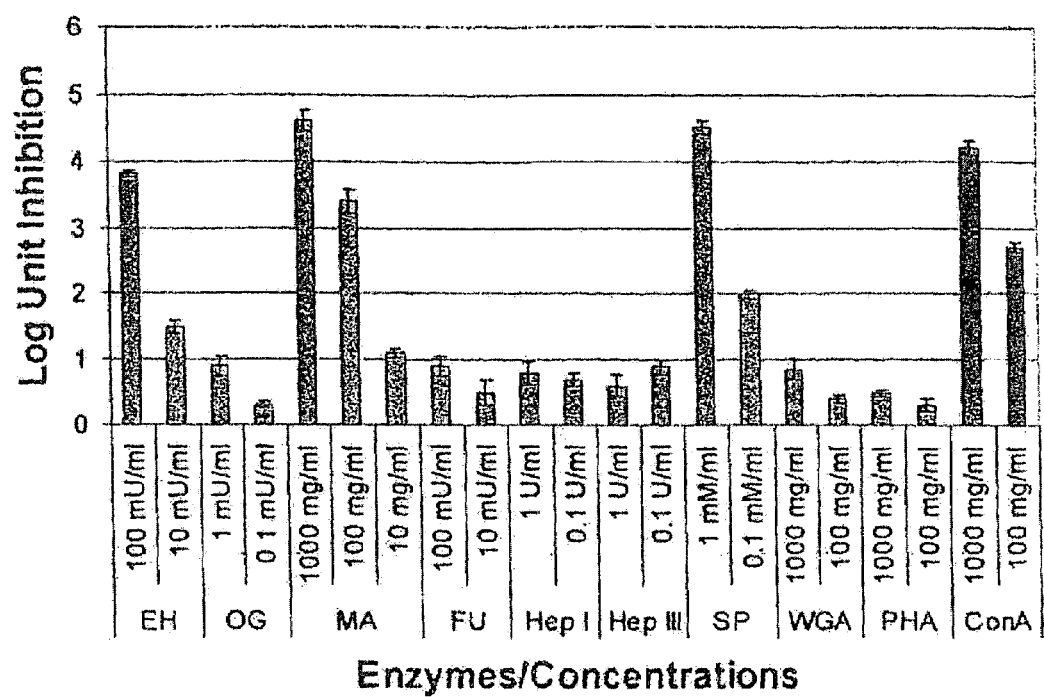
FIG. 1B shows a diagram reporting the effect of enzyme, sodium periodate and lectin treatment on West Nile virus binding molecules present on the surface of intact Vero cells. The y-axis shows the inhibition of West Nile virus entry expressed as the number of log unit inhibition with respect to untreated samples. On the x-axis, the dosage of substance administered is reported. EH=Endoglycosidase H, OG=O-Glycosidase, MA=α-Mannosidase; FU=α-Fucosidase; HepI=Heparinase I; HepIII=Heparinase III; SP=Sodium Periodate; WGA=Wheat Germ Agglutinin; PHA=phytohemagglutinin; ConA=Concanavalin-A.

FIGS. 1A and 1B show the effects of phospholipases, proteases, glycosidases, sodium periodate and lectins treatments on Vero cells and the subsequent ability of the cells to allow West Nile virus infection.

In particular, results shown in FIG. 1A, demonstrate that treatment of Vero cells with the three phospholipases does not cause any significant reduction in the productive yields of West Nile virus. Vero cells were also treated with a panel of proteases which included both serine and thiol proteases. Pretreatment of Vero cells with proteases exhibited a dosage-dependent inhibition of West Nile virus entry. Papain, a cysteine endopeptidase that solubilized integral membrane protein, showed the highest inhibition (approximately a 5-log unit inhibition) of West Nile virus infection. Therefore, these results show that the cellular receptor molecule responsible for West Nile virus entry is of a proteineous nature.

In particular, results shown in FIG. 1B demonstrate the effects of treatment with heparinases, glycosidases and sodium periodate. With reference to heparinases, pretreatment of a cell with heparinases has no effect on the entry of West Nile virus. This result was further supported by a virus entry blockage study using anti-heparan sulfate proteoglycan treatments of cells.

As per the glycosidases, both Endoglycosidase H and α-mannosidase (which hydrolyzes N-linked oligossacharides with mannose structures and α-mannose residues respectively) had a significant inhibition on West Nile virus binding and entry into Vero cells. In agreement with this result, pretreatment of cells with sodium periodate also substantially reduced the binding ability of the cells for West Nile virus. Sodium periodate works by oxidizing cell surface carbohydrate residues, but without altering protein or lipid epitopes. As for O-glycosidase, α-fucosidase and Heparinase I and III treatments, these enzymes had minimal effect on West Nile virus infection. In this series of glycosidase treatments, protease inhibitors cocktails were included to prevent possible contamination by proteases.

With reference to treatment with lectins, blocking of the mannose residues on N-linked glycans with concanavalin-A on the cell surfaces prevented the entry of West Nile virus into Vero cells.

Therefore, these preliminary results suggested that the West Nile virus cellular receptor molecule(s) on Vero and N2A cells is a glycoprotein with complex N-linked sugars containing α-mannose residues.

Example 2

Isolation of Receptor Protein

In these experiments, plasma membrane proteins were isolated and purity was checked under the electron microscope. The purity of the plasma membrane extract was considered acceptable with reference to Atkinson and Summers (1971). Equal quantities of the membrane proteins were loaded into different gel lanes and separated by SDS-PAGE and transferred onto nitrocellulose membranes. The nitrocellulose membranes were incubated sequentially with purified West Nile virus, rabbit polyclonal mono-specific antibody against the viral envelope protein and detection by secondary anti-rabbit antibodies conjugated with alkaline phosphatase with addition of substrate (NBT).

In particular, in order to isolate the West Nile virus binding cell receptor proteins in Vero and N2A plasma membrane extracts, VOPBAs were performed. Membrane proteins (80 μg) from either Vero or N2A cells were separated by sodium dodecyl sulfate-10% polyacrylamide gel electrophoresis (SDS-PAGE) as described by Sambrook and co-workers (1989). Proteins separated by SDS-PAGE were electrophoretically transferred onto a nitrocellulose membrane using a Western Blotting transfer apparatus for 3 hours at 4° C. The nitrocellulose membrane was soaked overnight in a milk buffer (5% skim milk and 0.5% BSA) to block non-specific binding sites and to allow re-naturation of the separated proteins. The membrane was rinsed with PBS (three times) and incubated sequentially with (a) the purified West Nile virus (prepared as describe above) for 6 hours at 4° C. (b) mono-specific polyclonal antibodies against West Nile virus envelope protein for 1 hour at 37° C. (c) secondary antibody (anti-rabbit IgG) conjugated with alkaline phosphatase (Chemicon Int, USA) for 45 minutes at 37° C. All incubations were carried out on a rocking platform and membranes were washed three times with a washing buffer (containing 50 mM Tris and 200 mM NaCl with 0.05% Tween 20). Non-specific binding of the virus particles was reduced with a high salt buffer wash. The presence of virus binding was detected by the addition of substrate, nitroblue tetrazolium. Finally, the membranes were washed with distilled water and dried (and/or put in stripping and re-probing protocol).

A 105-KDa band was detected. The corresponding 105-kDa plasma membrane protein (from Vero cells) was excised from the SDS-10% PAGE gels, homogenized and incubated with ImmunEasy mouse adjuvant at a concentration recommended by the manufacturer, Qiagen. The antigen-adjuvant mixture was used to immunize BALB/C mice five times subcutaneously at 14-day intervals. Mouse sera were collected 12 days after the last booster. Mouse sera were purified using Econo-Pac serum IgG purification kits and dialyzed overnight with PBS. The purified immunoglobulins were stored at −20° C. Sera were tested by Western blotting detection for the presence and specificity of antibody against the 105-kDa cell receptor protein.

Results are shown in FIGS. 2A and 2B. West Nile virus was observed to bind to a 105-kDa band in the membrane preparations of both Vero and N2A cells (FIGS. 2A and 2B, respectively, Lane 1). No bands were observed when supernatants of uninfected cells (prepared as according to the supernatants of West Nile virus-infected cells) were incubated under the same conditions (FIGS. 2A and 2B, respectively, Lane 2).

To ensure this was a specific interaction between the virus and the 105-kDa cell receptor protein, several procedures were carried out. In particular, despite high salt (200 mM NaCl) and detergent (0.05% Tween 20) washing, West Nile virus still binds strongly to the 105-kDa cell receptor proteins.

Example 3

Protease Treatment of Membrane Proteins

To affirm the results of enzymes and chemical treatments of intact Vero cells reported in the previous examples, VOPBAs were also performed on plasma membrane protein extracts that were treated with protease (papain).

After papain treatment of both vero and N2A cells, the membrane proteins were isolated and prepared and VOPBAs were performed according to the procedure described in example 2.

The results are shown in FIG. 3. WN virus binding to the membrane proteins of both Vero and N2A cells after papain treatment at the concentration of 50 mUnit/ml is abolished (Lanes 2 & 4 respectively) as compared to that of the untreated cells (Lanes 1 & 3 respectively). These results confirm that the receptor is of a proteinaceous nature. Additionally, since also after this treatment a 105 KDa band was observed, the existence of a 105-KDa virus receptor was further confirmed.

Example 4

Kinetics of West Nile Virus Binding Molecules

Following the experiments reported in example 3, the kinetics of West Nile virus binding molecules returning to the cell surface after removal with papain was also examined.

Vero cells (approximately $5 \times 10^6$ cells) were treated with papain at 50 mUnit/ml in PBS or PBS (untreated) for 45 minutes at 25° C. Another set of Vero cells was incubated with 100 μg/ml of cycloheximide to block new protein synthesis, for 2 hours prior to papain treatments. Treated cells were washed twice with PBS supplemented with 2% FCS to inactivate the enzyme. Fresh M199 plus 10% FCS with or without cycloheximide (100 μg/ml) were added to the cells. The cells were then incubated at 37° C. in 5% $CO_2$. At specific times after incubation (0, 2 & 4 hours), plasma membrane proteins were extracted as herein described and VOPBA was performed.

Figure 4:
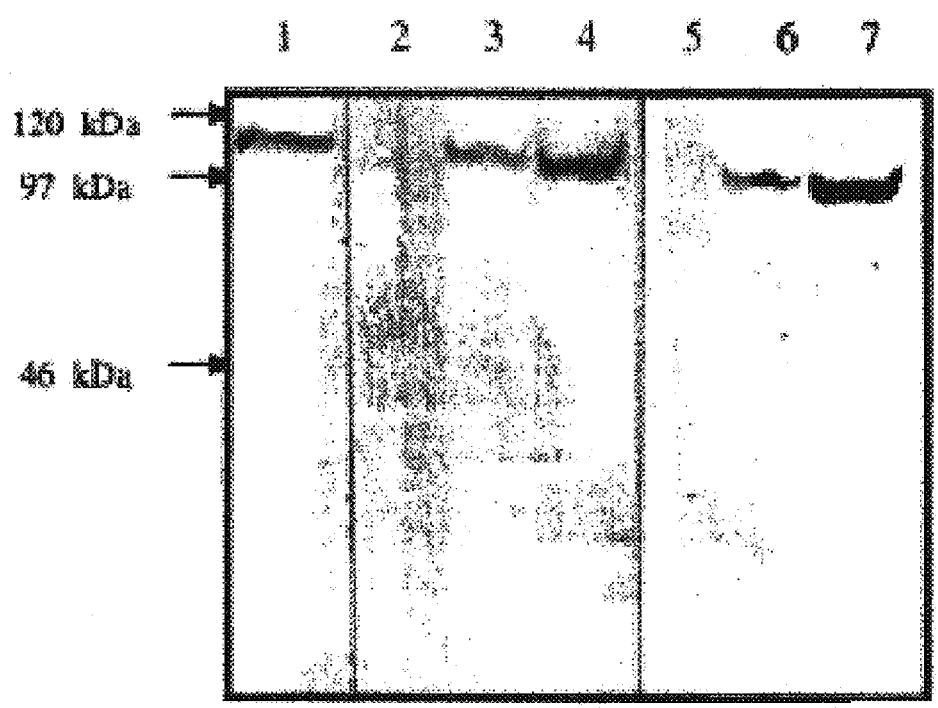
FIG. 4 shows results of a VOPBA performed on plasma membrane proteins from Vero cells after papain treatment (Lane 2—after 0 hours; lane 3—after 2 hours; Lane 4—after 4 hours), as compared to those of untreated cells (Lane 1) and those of treated cells further subjected to cycloheximide treatment (Lane 2—after 0 hour; lane 3 —after 2 hours; Lane 4—after 4 hours). Molecular size markers are indicated on the left side of the Figure by arrows.

The results of these experiments are shown in FIG. 4. Vero cells were first treated with papain (50 mU/ml) for 45 minutes at room temperature and after protease (papain) removal after 0, 2 and 4 hours, virus binding was determined by VOPBA. No virus binding was observed at 0 hr following the removal of the protease [FIG. 4—Lane 2 (without cycloheximide and Lane 5 (with cycloheximide)] when compared to the membrane protein that is not treated with papain (Lane 1). West Nile virus binding to the 105-kDa cell receptor protein was observed after 2 hours with the removal of the protease and reached its original level within 4 hours (FIG. 4—Lanes 3 & 4 respectively). Despite the blockage of new protein synthesis by cycloheximide, virus binding was also observed after 2 hours and 4 hours (FIG. 4—Lanes 6 & 7 respectively). This indicates the presence of abundant pre-existing internal pools of the 105-kDa cell receptor proteins that were rapidly trafficked to the cell surface after removal without the need for new protein synthesis to occur.

Example 5

Glycosidase Periodate and Lectins Treatement of Membrane Proteins

Carbohydrate residues on cell surfaces have been shown to be important for the initial binding of viruses, which would then mediate the subsequent entry of the virus through its high affinity receptor. The nature and roles of carbohydrate residues present on the 105-kDa protein for West Nile virus binding were further assessed by VOPBA.

In particular, VOPBAs were also performed on plasma membrane protein extracts (obtained with the procedure reported in example 4) that were treated with glycosidases (Endoglycosidase H, α-mannosidase and O-glycosidase), sodium periodate and lectins.

After each treatment, membrane proteins were isolated and prepared, and VOPBAs performed according to the procedures described in example 2.

Figure 5A:
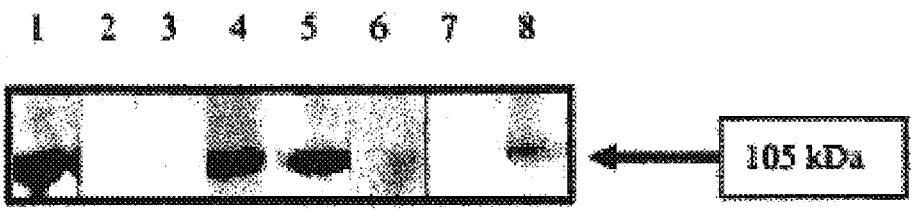
FIG. 5A shows results of a VOPBA performed on plasma membrane proteins extracted from Vero cells (Lanes 1 to 4) and N2A cells (Lanes 5 to 8) either left untreated (Lanes 1 and 5) or subjected to α-mannosidase (Lanes 2 and 6), Endoglycosidase H (Lanes 3 and 7) and O-glycosidase (Lanes 4 and 8). A molecular size marker is indicated on the right side of the Figure by an arrow.
Figure 5B:
FIG. 5B shows results of a VOPBA performed on plasma membrane proteins obtained from Vero cells pretreated with lectins, concananvalin-A [Lane 1 (untreated), Lane 2 (10 µg/ml) and Lane 3 (100 µg/ml)] and phytohemagglutinin [Lanes 4 (untreated), Lane 5 (10 µg/ml) and Lane 6 (100 µg/ml)]. A molecular size marker is indicated on the right side of the Figure by an arrow.
Figure 5C:
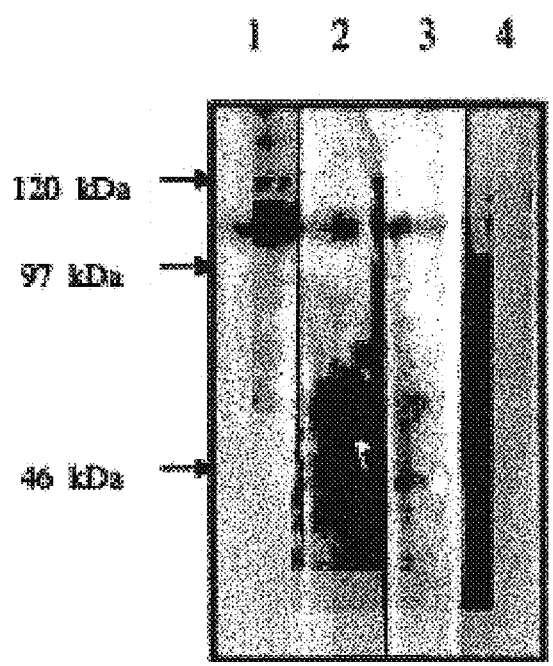
FIG. 5C shows results of a VOPBA performed on plasma membrane proteins obtained from Vero cells either left untreated (Lane 1) or treated with 0.1 mM (Lane 2), 1 mM (Lane 3) and 10 mM (Lane 4) of sodium periodate. Molecular size markers are indicated on the left side of the Figure by arrows.

Results of these experiments are shown in FIGS. 5A to 5C. FIG. 5A shows the results of glycosidase treatments of membrane proteins. No binding of West Nile virus was observed after treatment with α-mannosidase and Endoglycosidase H in both Vero (Lanes 2 and 3) and N2A (Lanes 6 and 7) plasma membrane protein extracts, when compared with the untreated membrane proteins (Vero cells—Lane 1 and N2A cells—Lane 5). In contrast, O-glycosidase treatment of the membrane proteins (Vero cells—Lane 4 and N2A cells—Lane 8) did not affect the binding of West Nile virus to the 105-kDa protein band. It could be deduced that virus binding to the 105-kDa cell receptor protein is neither mediated by O-linked sugars nor contains O-linked glycoslation. The nature of carbohydrates present in the 105-kDa cell receptor proteins necessary for West Nile virus binding was further assessed by lectin treatments using VOPBA.

Based on the results shown in FIG. 5B, concananvalin-A was observed to block the binding of West Nile virus to the 105-kDa cell receptor proteins in a dosage-dependent manner [Lane 1 (untreated), Lane 2 (10 µg/ml) and Lane 3 (100 µg/ml)]. On the other hand, phytohemagglutinin had no effect in blocking virus binding to the cell receptor proteins [equal intensities—Lane 4 (untreated), Lane 5 (10 µg/ml) and Lane 6 100 µg/ml)].

Similarly, FIG. 5C shows that binding of West Nile virus to the sodium periodate-treated membrane proteins was reduced in a dosage-dependent manner (FIG. 5C, Lane 1—untreated, Lane 2—0.1 mM, Lane 3—1 mM and Lane 4—10 mM). These results have provided more evidence that the 105-kDa cell receptor protein contains carbohydrate groups with high mannose residues that are important for virus binding.

Therefore, treatment of membrane proteins with Endoglycosidase H or α-mannosidase abolished virus binding (FIG. 5A) while sodium periodate exhibited a dosage dependent inhibition of West Nile virus binding to the 105-kDa cell receptor protein (FIG. 5C). Since Endoglycosidase H cleaves only the high mannose residues of N-linked oligosaccharides on glycoproteins and concanavanlin-A binds specifically to mannose residues (FIG. 5B), this further emphasizes importance of N-linked sugars with mannose residues on the 105-kDa cell receptor protein for West Nile virus binding.

Example 6

β-Mercaptoethanol Treatment of Membrane Proteins

To investigate the possible presence of di-sulfide-linked bridges in the 105-KDa plasma protein, plasma membrane extracts according to the procedure reported in example 4, were also treated with 5 mM of β-mercaptoethanol.

Figure 6:
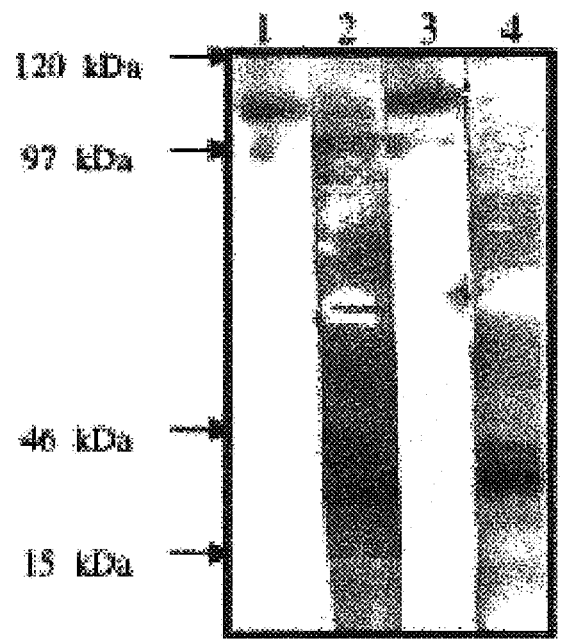
FIG. 6 shows results of a VOPBA performed on membrane proteins from Vero cells and N2A cells after β-mercaptoethanol treatment (Lane 2—Vero cells; lane 4 —N2A) as compared to those of the untreated cells (Lane 1—Vero cells and Lane 3—N2A cells). Molecular size markers are indicated on the left side of the Figure by arrows.

Interestingly, a faint 105-kDa band and a series of protein bands ranging from 30 to 40-kDa were observed after treatment with β-mercaptoenthanol, followed by VOPBA [FIG. 6—Lanes 2 (Vero cells) & 4 (N2A cells)]. Lanes 1 and 3 are untreated samples from Vero and N2A cells, respectively. These results may suggest that treatment with β-mercaptoethanol did not disrupt virus binding and virus binding occurs mainly through the interaction with the carbohydrate moieties instead of the peptide portion of the glycoprotein.

Consistent with treatment of the membrane proteins with β-mecaptoethanol, West Nile virus was observed to bind to a series of protein bands ranging from 30 to 40-kDa (FIG. 6). This may indicate that the 105-kDa cell receptor protein is made up of di-sulfide linked subunits. However, it might be equally plausible that the virus binding protein is actually 30 kDa, and upon cell lysis it becomes cross-linked via inadvertent di-suflide linkage to other proteins.

To investigate the actual molecular weight of the virus binding protein, the plasma membrane extraction procedure was repeated in the presence of alkaylating agent (iodoacetamide) to block thiol reactivities. Consistent with the result obtained in the absence of alkaylating agent, West Nile virus binds to a single 105-kDa protein.

Furthermore, the action of β-mecaptoethanol did not seem to affect virus binding to the protein subunits. This interesting result suggests either that West Nile virus binding did not require a folding dependent di-sulfide bridge or that the West Nile virus binds to the carbohydrates residues on the protein not affected by the action of β-mecaptoethanol. The latter is in line with the above observations that the carbohydrate residues on the membrane protein are necessary for virus binding.

Example 7

Western Blot Analysis

For analysis of the specificity of the anti-105-kDa polyclonal antibodies, plasma membrane proteins from Vero cells were separated using SDS-polyacrylamide gel electrophoresis and transferred to nitrocellulose membrane (Biorad, USA). The Western blot procedure was carried out as described in Chu and Ng (2002). The blot was then incubated overnight in the anti-105-kDa protein antibodies or pre-immune serum at room temperature on an orbital shaker for 1 hour. Reactions were then detected by staining with alkaline-phophatase conjugated goat anti-mouse IgG (Chemicon Int, USA) with the addition of substrate, nitroblue tetrazolium (NBT).

Figure 7:
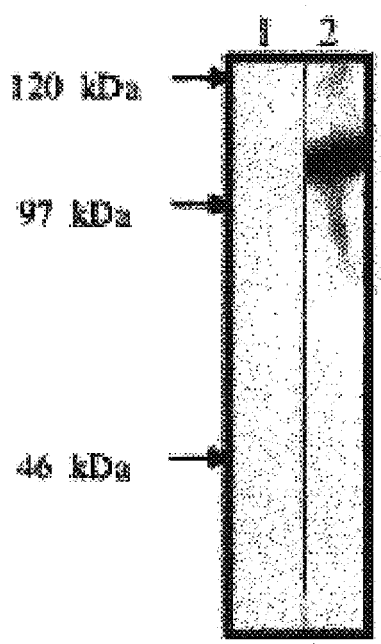
FIG. 7 shows results of a Western Blotting performed on membrane proteins from plasma membrane extracts of Vero cells. Incubation of separated membrane proteins with the preimmune serum (Lane 1) and the anti-105-kDa protein polyclonal antibodies at a dilution of 1:500 (Lane 2) was performed. Molecular size markers are indicated on the left side of the Figure by arrows.

Results are shown in FIG. 7. The murine polyclonal antibody generated against the 105-kDa protein was shown to be specific for the 105-kDa protein (from Vero cells) by Western blot assay (FIG. 7, Lane 2) while no bands were observed after incubation with preimmune serum (FIG. 7, Lane 1). This murine polyclonal antibody was also specific for the 105-kDa cell receptor protein from N2A cells.

Example 8

Indirect Immunofluorescence Confocal Microscopy

To determine the localization of the 105-kDa proteins on Vero cells, immunofluorescence assays were carried out. To determine whether the 105-kDa cell receptor protein is differentially expressed in polarized cells, immunofluorescence assays coupled with optical sectioning by laser scanning confocal microscopy were also carried out with Vero C1008 cells. The Vero C1008 is a polarized cell line derived from Vero cells. These epithelial cells have distinct apical and basolateral domains of the plasma membrane.

For immunofluorescence microscopy, cell monolayers were grown on cover slips or 0.4 μm porous support membrane inserts. The subsequent procedure is similar to that described in Chu & Ng (2002). The primary antibody used was anti-105-kDa polyclonal antibody (with a 1:100) and the fluorochrome were Texas Red (TR)-conjugated secondary antibodies. The specimens were viewed with laser scanning confocal inverted microscope (excitation wavelength of 543 nm for TR) using oil immersion objectives.

Figure 8A:
FIG. 8A shows Vero cells processed for immunofluorescence and confocal microscopy. The arrows indicate the 105-kDa proteins distributed along the plasma membrane as shown by the red staining.

Results are shown in FIG. 8A. The 105-kDa cell receptor protein was mainly localized to the plasma membrane as detected by the anti-105-kDa protein antibodies using indirect immunofluorescence. This is a typical localization pattern for cell surface molecules. Despite methanol fixation and permeabilization, the murine polyclonal antibodies against the 105-kDa protein still bind specifically to the plasma membrane (arrows).

Figure 8B:
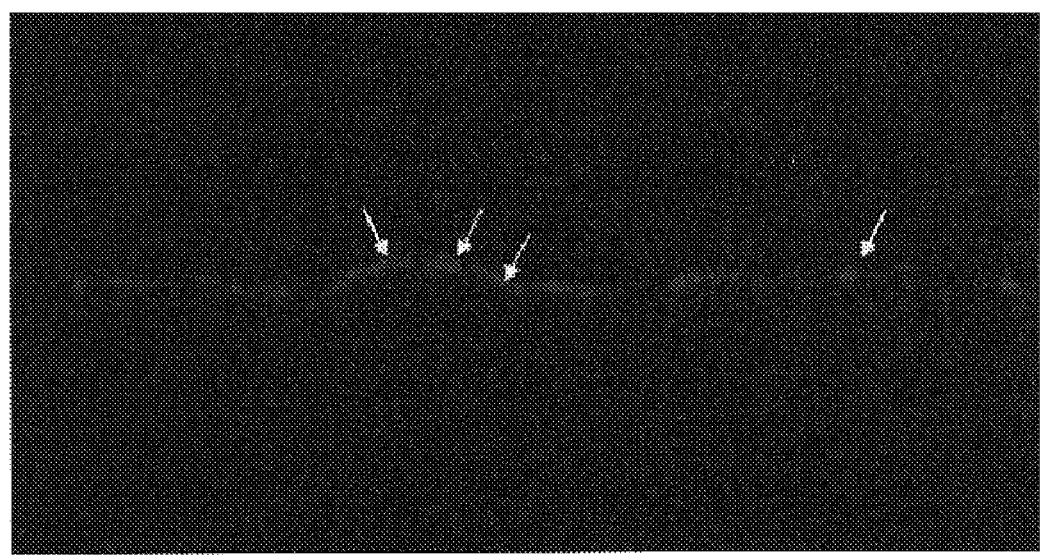
FIG. 8B shows apical localization of the 105-kDa membrane proteins on Z-section (cross-section) of polarized Vero C1008 epithelial cells. The arrows indicate the 105-kDa membrane proteins at the apical surface of the cells.

Results of experiments performed in polarized cells are shown in FIG. 8B. In polarized epithelial cells (Vero C1008), there was a high level of expression of the 105-kDa proteins at the apical surface as compared to the basolateral surface (FIG. 8B). This result could explain for the preferential entry of West Nile virus through the apical surface of the polarized Vero C1008 cells as illustrated in a previous study (Chu and Ng, 2002).

Example 9

Cryo-Immunolabelling Electron Microscopy

To confirm the results of example 8, cryo-immuno-labelling electron microscopy also was carried out.

Vero cells were incubated with West Nile virus (MOI=100) at 4° C. for 30 minutes to allow virus attachment to the plasma membrane. The cells were then processed for cryo-electron microscopy using the Tokuyasu method (1984) with some modifications as described in Ng and colleagues (2001). Briefly, the cells were fixed in 4% paraformaldehyde and 0.2% glutaldehyde followed by embedding in gelatin. The gelatin block with the cells was immersed in cryo-protectant, rapidly frozen before cryo-ultramicroscopy, using an ultramicrotome (UCT) having a cryo-attachment.

For immuno-labeling, the primary antibody was the anti-105-kDa membrane protein (1:100 dilution) followed by conjugation with Protein A colloidal gold (at dilution 1:20). The sections were viewed under the CM120 Biotwin transmission electron microscope.

Figure 9:
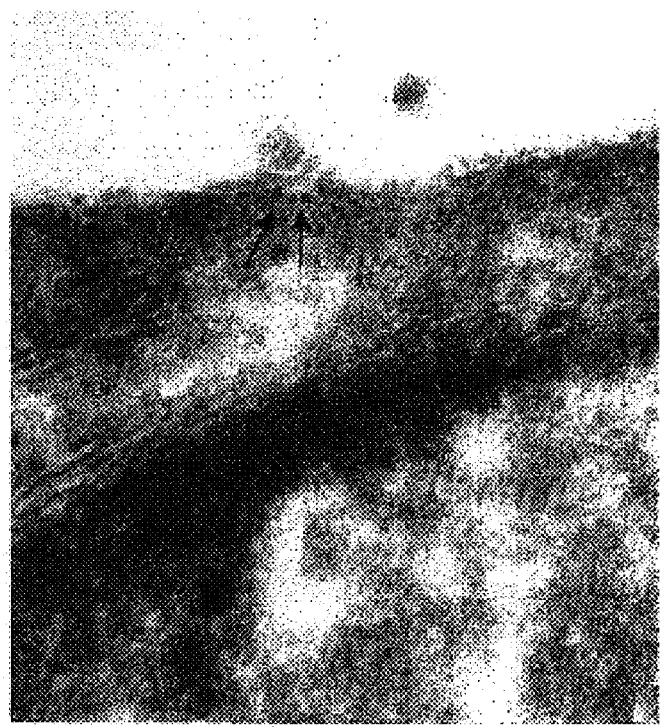
FIG. 9 shows Immunogold-labeling of the 105-kDa proteins on cryo-sections of Vero cells. The arrow indicates the binding of West Nile virus to the 105-kDa membrane protein indicated by arrows at the site of virus attachment.

Results are shown in FIG. 9. In particular, localization of the 105-kDa protein was confirmed by the immuno-gold labeling of cryo-sections. More particularly, at the ultrastructural level, West Nile virus was observed to bind to the 105-kDa cell receptor proteins as defined by the 10 nm gold particles—(arrows) at the plasma membrane. The use of immuno-cryo electron microscopy revealed the specific binding of West Nile virus to the 105-kDa cell receptor protein.

Example 10

Inhibition of Binding of West Nile Virus to Membrane Cells by Receptor Protein Polyclonal Antibodies Inhibition of binding of West Nile virus to membrane cells by 105-KDa protein was tested.

After pre-incubation with the 105 KDa protein antibodies, membrane cells proteins were isolated and prepared, and VOPBAs performed according to the procedure reported in example 2.

Figure 10:
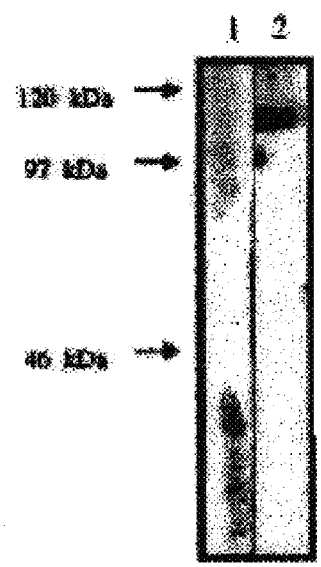
FIG. 10 shows a VOPBA of Vero plasma membrane protein pre-incubated with anti-105 kDa murine antibodies (Lane 1) compared to that of untreated cells (Lane 2). Molecular size markers are indicated on the left side of the Figure by arrows.

Results are shown in FIG. 10. The pre-incubation of the 105 kDa protein antibodies on the separated membrane proteins through VOPBA also prevented the binding of West Nile virus (FIG. 10, Lane 1). Virus binding occurred in the absence of the 105-kDa protein antibodies (Lane 2). Hence, these results provide strong evidence that the 105-kDa cell receptor protein is a possible cellular receptor for West Nile virus and other closely-related flaviviruses.

Example 11

Inhibition of West Nile Virus Infection by Receptor Protein Polyclonal Antibodies This set of experiments was carried out to determine if the antibodies against the 105-kDa protein recognized the same cell receptor protein for West Nile virus entry. Blockage of West Nile virus cellular receptors with specific antibodies against the cell receptor protein would prevent virus entry.

Confluent monolayer of Vero cells were first washed twice with PBS and preincubated with preimmune serum or the anti-105-kDa polyclonal antibodies for 1 hour at 37° C. After incubation, cells were washed thrice with PBS and infected with West Nile virus, Kunjin virus (a flavivirus in the same subgroup as West Nile virus), Dengue (another flavivirus) (MOI=10). At appropriate p.i. time periods, supernatants from the virus-infected cells were processed for plaque assays. For control purposes, the above procedures were repeated with an unrelated poliovirus infection.

Results are shown in Table 1 below.

TABLE 1

| WN | Kunjin | Polio |
|---|---|---|
| Log unit inhibition of infectivity by pre-immune sera at the following dilutions. | | |
| 1:10 | 1:100 | 1:1000 |
| 0.25 ± 0.56 | 0.15 ± 0.85 | 0.20 ± 0.50 |
| 0.35 ± 0.22 | 0.28 ± 0.60 | 0.32 ± 0.68 |
| 0.95 ± 0.25 | 0.89 ± 0.87 | 0.88 ± 0.75 |
| Log unit inhibition of infectivity by anti-105 kDa Membrane Protein at the following dilutions. | | |
| 1:10 | 1:100 | 1:1000 |
| 6.5 ± 0.80 | 4.5 ± 0.45 | 0.6 ± 0.50 |
| 4.0 ± 0.35 | 2.8 ± 0.60 | 0.35 ± 0.20 |
| 0.85 ± 0.90 | 0.90 ± 0.55 | 0.75 ± 0.20 |

The entry of West Nile and kunjin virus was strongly inhibited, while preimmune sera did not cause any inhibition. In contrast, the entry of poliovirus, a non-related picornavirus, was not affected in the presence of the 105-kDa protein antibody.

These results therefore strongly support the conclusion that the 105-kDa glycoprotein is the receptor for West Nile virus. Additionally, since the anti-105-kDa membrane protein antibodies were also effective in blocking the entry of the flavivirus kunjin virus, other flaviviruses of the Japanese encephalitis serocomplex subgroup, such as St. Louis encephalitis, Murray Valley encephalitis, kunjin viruses, dengue virus 1, dengue virus 2, dengue virus 3 and dengue virus 4, might also utilize this 105-kDa cell receptor protein for entry into host cells.

Example 12

Location of the 105-kda Cell Receptor Protein in Vertebrates and Organs

Detection of the cell receptor protein from plasma membrane extracts from cells of several species, including vertebrates, utilizing a West Nile virus antibody and/or the cell receptor protein antibody is expected. Exemplary species comprise crows, horses, mice and humans, to determine if the cell receptor protein is present in these groups and if it can bind a flavivirus. This is shown by providing membrane proteins, loaded into different gel lanes, separated by SDS-PAGE and transferred onto nitrocellulose membrane. The nitrocellulose membranes are incubated sequentially with purified West Nile virus, rabbit polyclonal mono-specific antibody against the viral envelope protein and then detected by secondary anti-rabbit antibodies conjugated with alkaline phosphatase with addition of substrate (NBT), for example.

The nitrocellulose membranes can be stripped and re-probed with the 105 kDa protein antibody. Exemplary incubation of separated membrane proteins with preimmune serum and antibodies at a dilution of 1:500 for crows, horses, mice and humans is contemplated, as well as use of Goat anti-mouse IgG conjugated with alkaline phosphatase, at a dilution of 1:2000. The antibody binding generated will be highly specific for 105-kDa membrane protein in a range of species. Antibody binding found in all species indicates that the cell receptor protein is present in a wide range of vertebrates. This would account for the wide pathogenicity of the West Nile virus among vertebrates.

Example 13

Peptide Sequencing of the 105-kda Cell Receptor Protein

Peptide sequencing of the 105 KDa membrane-associated glycoprotein was carried out to determine the identity of the glycoprotein following the procedure disclosed in Sagara et al, 1998

The amino acidic sequences reported in the sequence listing as SEQ ID NO: 1, SEQ ID NO: 2, SEQ ID NO: 3, SEQ ID NO: 4 and SEQ ID NO: 5, have been obtained as a result. These sequences closely match to those of the integrin superfamily after performing a database protein homology search in the databases Entrez Protein and NCBI, following procedures known to the person skilled in the art. Therefore, the peptide sequencing shows that the 105 KDa glycoprotein belongs to the integrin superfamily.

Example 14

105-kda Cell Receptor Protein Identity

To determine the specific integrin molecule(s) or its (their) subunit of the integrin superfamily that mediate binding and entry of West Nile Virus, Vero cells were pre-incubated with a panel of functional blocking antibodies against integrins (α1, α2, α3, α4, α5, α6, αV, β1, β2, β3, β4, β5—Chemicon USA and Santa Cruz Biotech, USA) following procedures disclosed in Sagara et al 1998 at 4° C. (to determine virus binding) or 37° C. (to determine virus entry). Antibodies from different In particula antibodies from different companies has been used to ensure reliability of results on inhibitory effect on West Nile virus binding to Vero cells.

Radioactive labeled West Nile Virus were then added to the treated cells and further incubated for 1 h at 4° C. or 37° C. Excess and unbound particles were inactivated in acid glycine buffer (pH3) and removed by washing with PBS for three times. Results concerning virus binding are shown in FIG. 11A. Results concerning virus entry are shown in FIG. 11B. A significant inhibition of the entry of the virus is shown by treatment of antibodies aginst all the integrins subunits tested. Antibodies against integrin αVβ3 and its individual subunits (αV and β3) showed the highest inhibition of West Nile virus binding and entry. Anti αVβ5 integrin antibodies also show some extent of West Nile virus binding and entry. In particular αVβ5 is also capable of blocking the binding of West Nile virus and much lesser effect on the entry of West Nile Virus, showing that integrin alpha V is functioning as the specific binding molecule for WNV.

This experiment is repeated with another closely related flavivirus, Japanese Encephalitis Virus using all the anti integrin antibodies at 25 μg/ml. Results are shown in FIG. 12. Antibodies against integrin subunits (αV and β3) and integrin αVβ3 strongly inhibit the entry of Japanese Encephalitis Virus into Vero cells.

Therefore, the results obtained show that αVβ3 is the receptor molecule for both West Nile and Japanese Encephalitis virus and that both the integrin subunits of αV and β3 are required in binding to West Nile and Japanese Encephalitis virus.

Example 15

Role of Divalent Cations in the Binding of WNV and JEV

Confluent Vero cells were first washed with phosphate buffered saline (pH 7.4) and added with fresh culture medium M199 with 1% FCS containing EDTA (3-12 mM). The cells were incubated with EDTA for 2 hrs at 37° C. After the incubation period, Vero cells were added with radiolabelled WNV particles and assess for its entry into Vero cells.

Figures 13, 14:
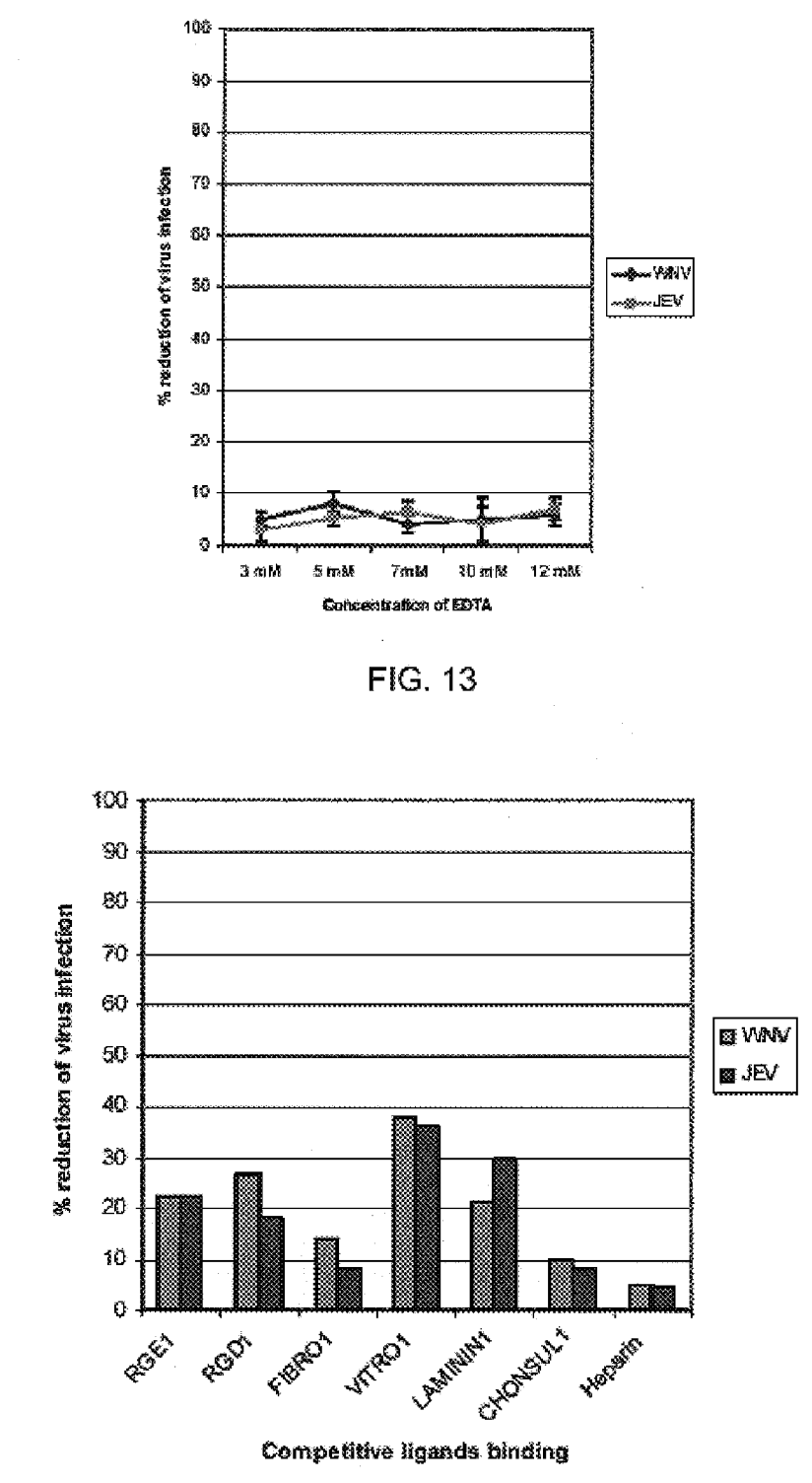

Divalent cations ($Ca^{2+}$) have been shown to be involved in the specific binding of physiological ligands to integrin. The possible requirement of divalent cations for binding of WNV to integrins was investigated by using EDTA (divalent cations chelators). Vero cells were treated with EDTA at a series of concentration that has been shown to inhibit the binding of physiological ligands to integrin. Results are shown in FIG. 13. Vero cells treated with EDTA did not block the binding and subsequent entry of West Nile virus. Therefore, removal of divalent cations from the culture environment did not have any effect on the entry of WNV into Vero cells.

Example 16

Competitive Physiological Ligand Binding Assay

Competitive physiological ligand binding assay with fibronectin, vitronectin, heparin, chrondriotin sulphate, laminin and the peptides RGD1 and RGE1 reported in the sequence listing as SEQ ID NO: 6 and SEQ ID NO:7 was carried out. In particular Vero cells were incubated with different concentrations of ECM proteins, RGD peptides, or anti-integrin antibodies at 4° C. or 37° C. for 1 hr, washed, incubated with 50 µl of radiolabeled WNV, JEV at 37° C. for 1 hr and assessed for virus entry.

Results are shown in FIG. 14. Binding of fibronectin vitronectin, laminin, and RGD peptide to cell surface has results only in partial inhibition of west Nile virus infection. At the same time, the partial inhibition by RGD peptide and physiological ligand (vitronectin) for integrin αVβ3 may propose that the binding of WNV to integrin may not be highly dependent on the usage of RGD motif on envelope protein of virus.

Previous studies have shown that many ligands and viruses can bind to integrin independently in the absence of RGD motif. Furthermore, site-directed mutagenesis of RGD motif in Murray Valley virus (flavivirus-JE serogroup) also shows consistent results that binding of Murray Valley virus to cells is independent of RGD motif on its envelope protein.

Example 17

Distribution and Localization of the 105 KDa Glycoprotein

To compare and confirm the results of experiments reported in examples 14 to 16, cell surface staining by immunofluorescence assay was carried out with antibodies against 105 KDa membrane protein and integrin αVβ3, respectively. Vero cells were fixed with methanol and processed for immunofluorescence staining. For immunofluorescence microscopy, cell monolayers were grown on cover slips and fixed with cold absolute methanol for 10 min. Subsequent procedure is similar to that described in Chu & Ng (2002). Antibodies against integrin αVβ3 and 105 KDa plasma membrane glycoprotein were used as the primary antibodies, respectively. Primary antibodies and specific secondary antibodies conjugated with FITC were added subsequently. The primary antibody utilized was an anti-105-kDa polyclonal antibody (1:100) and anti-integrin alphaV beta 3 monoclonal antibody (1:500), at indicated dilutions. The fluorochrome used was an FITC conjugated secondary antibody. The specimens were viewed with Olympus IX81 using oil immersion objectives.

Results are shown in FIGS. 15 A and B, respectively. In particular, integrins αVβ3 are distributed along the plasma membrane and focal adhesion through the cytoplasm (see FIG. 15A). Similar distribution patterns of the 105 KDa glycoprotein were also observed when compared to integrin αVβ3 shown in FIG. 15A. Thus, a similar distribution pattern between the 105 KDa glycoprotein and integrin αVβ3 is observed.

Therefore, these data show that the WNV virus binding 105 KDa plasma membrane protein is the integrin αVβ3.

Example 18

Gene Knockout and Down Regulation of Integrin αVβ3 in Vero Cells

To further confirm that integrin subunits αV and β3 are the receptor molecules for West Nile Virus, gene knockout by means of RNA intefering was carried out. Ten short gene sequences from the full length integrin αV gene sequence (SEQ ID NO: 8) and twelve short gene sequences from the full length integrin β3 gene sequence (SEQ ID NO:10) were selected and ligated into BamHI and HindIII digested pSilencer 3.0. In particular the following integrin sequences reported on the sequence listing as from SEQ ID NO: 12 to SEQ ID NO 15, were used: Integrin alpha V1 (SEQ ID NO: 12), Integrin alpha V2: (SEQ ID NO: 13); Integrin beta 31 (SEQ ID NO: 14); Integrin beta 32: (SEQ ID NO: 15). All twenty-two clones were selected and sequenced to verify in-frame insertion. All clones were then transfected into Vero cells and screened for down regulation of integrin expression.

In particular, plasmid constructs (psilencer 3.0-H1, Ambion, USA) containing different regions of the integrin alpha V beta 3 subunits (shown below) were constructed. Transfections were performed using Lipofectamine PLUS reagents from Invitrogen (USA) as specified by the manufacturer. In brief, Vero cells were grown on coverslips in 24-wells tissue culture plate until 75% confluency. 1 to 5 µg of the respective constructs was complexed with 4 µl of PLUS reagent in 25 µl of OPTI-MEM medium (GIBCO) for 15 min at room temperature. The mixture was then added to 25 µl of OPTI-MEM containing 2 µl of lipofectamine. After incubation for another 15 min, the DNA-liposome complexes were added to the cells. Following incubation for 3 h at 37° C., 1 ml of complete growth medium was added and incubated for another 24 hrs before virus entry assay was carried out. The down regulation of integrin was checked by immunofluorescence assay using antibodies against integrin alphaV and beta 3.

The transfection efficiency was determined to be approximately 35%. Results are shown in FIG. 16. Control formed by immunofluorescence staining of integrin αV and β3 on Vero cells using anti integrin αV and β3 antibodies is shown in FIGS. 16A and 16C. Those Figures respectively show that integrins αV and β3 are both mainly distributed at the cell surface and the focal adhesion junction. Vero cells transfected with pSilencer-siRNA integrin αV or integrin β3 shown in FIG. 16B and FIG. 16D respectively, show down regulation of integrin αV and β3 on Vero cells.

Figures 17, 18:
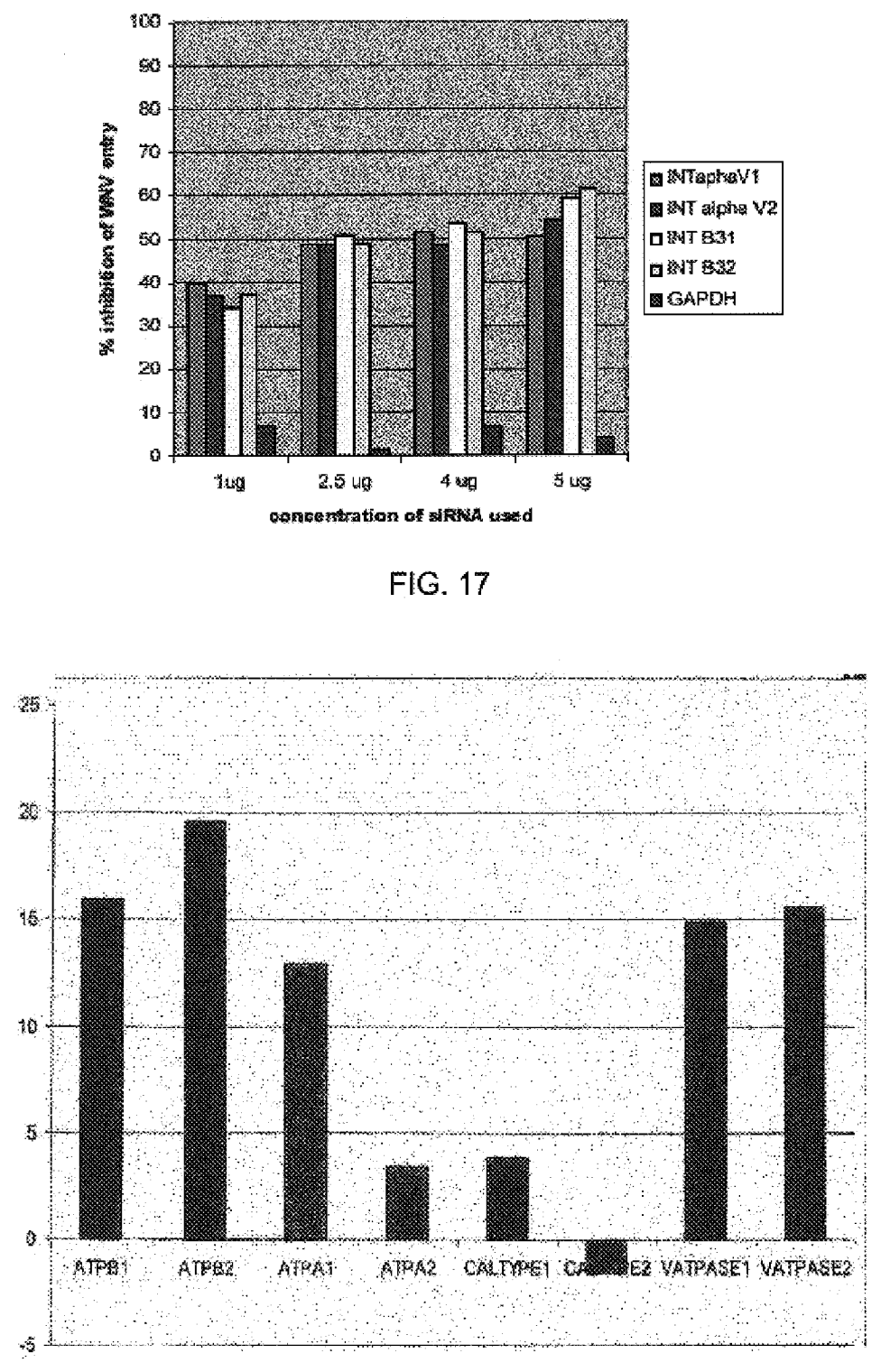

In particular, a number of these clones can strongly down-regulate the expression of integrin αV or β3 by 80%. These integrin down-regulated clones were selcted for WNV virus entry study. Results are shown in FIG. 17. The down-regulation of either integrin αV or β3 strongly inhibited the entry of West Nile Virus as compared to internal control of GADPH.

Example 19

ATPases Antibody Blocking Virus Entry Assays

Antibody Blocking Virus Entry Assays (ABVEA) performed using antibodies against various plasma membrane-associated proteins have shown significant inhibition of virus entry of blockage of ATPases (data not shown). To investigate the role of an ATPase as co-receptor of the West Nile Virus, a further series of ABVEA was performed using antibodies raised against plasma membrane related ATPases.

In particular Vero cells were grown in 96 wells microtitre plates till confluent. Cells were washed thrice with PBS and incubated with antibodies against ATPase beta subunit, ATPase alpha subunit, calcium dihydropyridine receptor alpha, calcium dihydropyridine receptor beta, VATPase E and VATPase for 1 hr at 37° C. Excess antibodies were removed by washing thrice with PBS. 50 µl of radiolabeled WNV were added and incubated for another 1 hr at 37° C. Excess virus were then inactivated and washed with acid glycine buffer (pH 2.8). Penetrated virus were then determined.

Results are shown in FIG. 18. The blocking of both plasma membrane associated ATPases and vacuolar ATPases with their respective antibodies seem to exert an inhibitory effect on the entry process of WNV. In general, ATPases are required to generate energy for many cellular activities across the plasma membrane. Hence, ATPases may act as co-receptor for WNV binding and providing the necessary energy for the endocytosis process of WNV.

Example 20

Neurotensin Antibody Blocking Virus Entry Assays

By using human brain cDNA library screening for interacting partners with WNV envelope protein in Yeast-2 hybrid system (not shown), a neurotensin receptor was obtained after several rounds of stringent selection. DNA sequence coding for neurotensin receptor is reported in the sequence listing as SEQ ID NO: 16, the amino acid sequence reported as SEQ ID NO: 17.

ABVEA were performed with antibodies against the neurotensin receptor in A172 neuroblastoma cells and in Vero cells as a control.

In particular Vero cells were grown in 96 wells microtitre plates till confluent. Cells were washed thrice with PBS and incubated with antibodies against nerotensin receptor for 1 hr at 37° C. Excess antibodies were removed by washing thrice with PBS. 50 µl of radiolabeled WNV were added and incubated for another 1 hr at 37° C. Excess virus were then inactivated and washed with acid glycine buffer (pH 2.8). Penetrated virus were then determined.

Figures 19, 20:
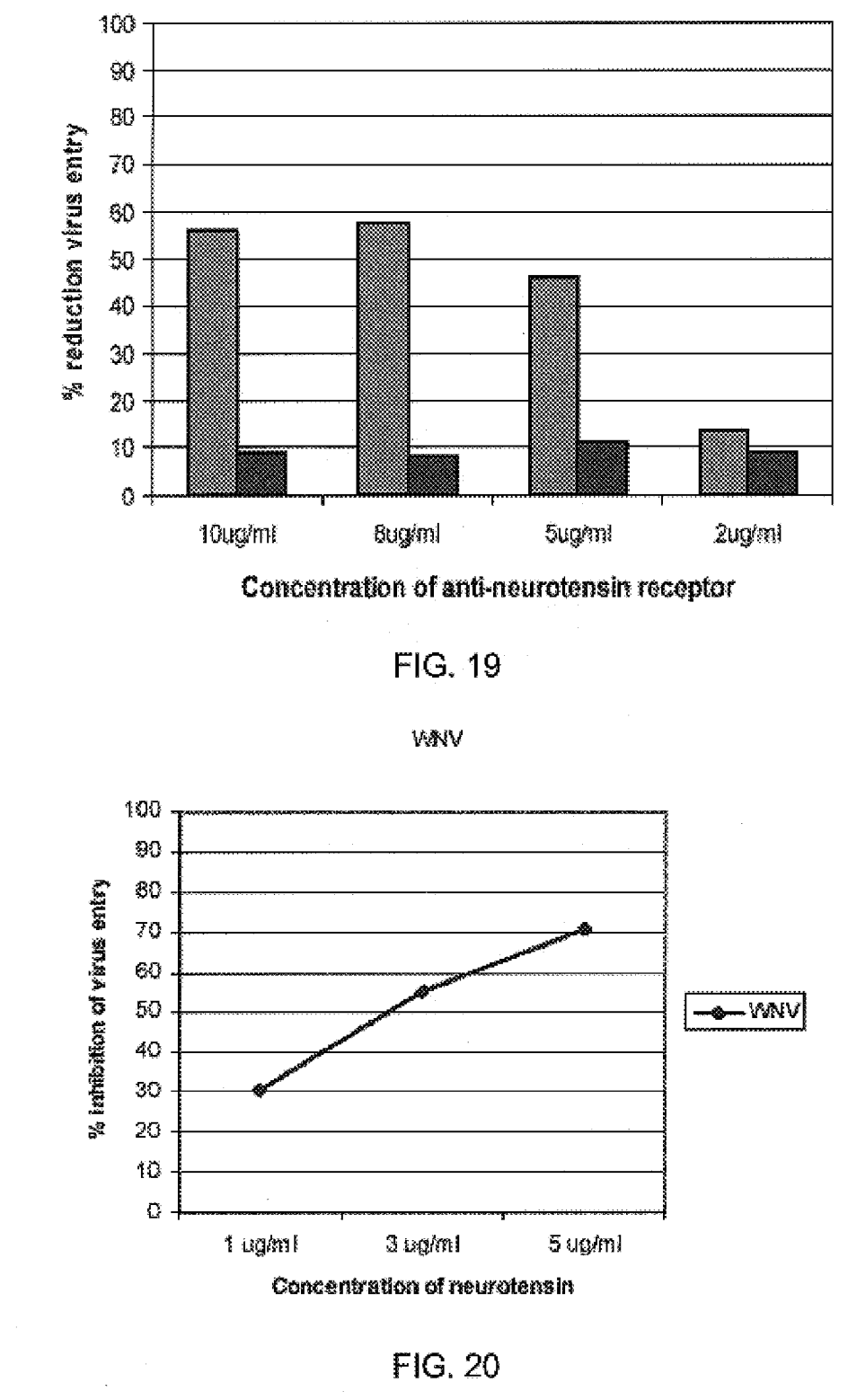

Results are shown in FIG. 19. Both A172 and Vero cells were pre-incubated with different concentrations of antibodies against neurotensin receptors and followed by incubation with radiolabeled WNV. Entry of WNV is significantly inhibited by anti-neurotensin receptor antibodies in A172 cells but not in Vero cells.

These results have been confirmed by WNV competitive binding assays of neurotensin receptor with its natural ligand. Results of such assays are shown in FIG. 20. Neurotensin (natural ligand) competitively blocked entry of WNV into A172 cells. A172 cells were pretreated with neurotensin at a different concentration before incubation of cells with readiolabeled WNV. Entry of WNV is blocked in a dosage dependent manner.

Example 21

Effect of Neurotensin Down Regulation to West Nile Virus Entry in A172 Cells

Work has been carried out to knockout the expression of neurotensin receptor in A172 cells and assess for West Nile virus entry. Three short gene sequences from the full length neurotensin receptor sequence were selected and ligated in BamHI and HindII digested pSilencer 3.0 (not shown). In particular the sequence reported in the sequence listing as SEQ ID NO: 18 was used.

Plasmid constructs (psilencer 3.0-H1, Ambion, USA) containing the neurotensin receptor sequence reported in the sequence listing as SEQ ID NO: 18 was transfected into A172 cells. Transfections were performed using Lipofectamine PLUS reagents from Invitrogen (USA) as specified by the manufacturer. In brief, Vero cells were grown on coverslips in 24-wells tissue culture plate until 75% confluency. 1 to 5 ug of the respective constructs was complexed with 4 µl of PLUS reagent in 25 µl of OPTI-MEM medium (GIBCO) for 15 min at room temperature. The mixture was then added to 25 µl of OPTI-MEM containing 2 µl of lipofectamine. After incubation for another 15 min, the DNA-liposome complexes were added to the cells. Following incubation for 3 h at 37° C., 1 ml of complete growth medium was added and incubated for another 24 hrs before virus entry assay was carried out.

Figure 21A:
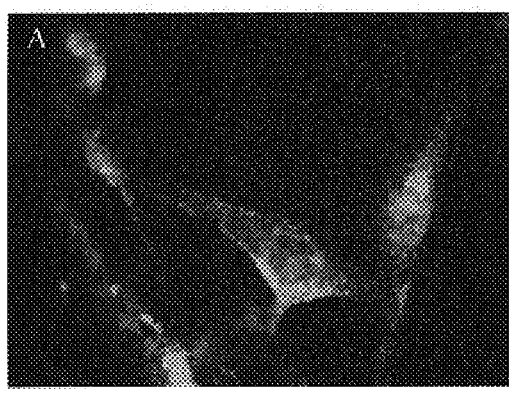
FIG. 21 shows immunofluorescence assays performed in A172 cells (A), and in A172 cells transfected with pSilencer-siRNA neurotensin receptor (B).
Figure 21B:
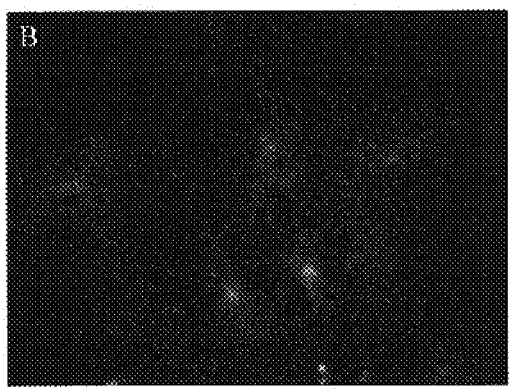

Clones were selected and sequenced to verify in frame insertion (not shown). All clones were then transfected into A172 cells and screened for down-regulation of neurotensin receptor expression. The down regulation of neurotensin receptor was checked by immunofluorescence assay using antibodies against neurotensin receptor. To demonstrate expression and localization of the receptor immunofluorescence assay with the antineurotensin receptor, antibodies were used. Results are shown in FIG. 21. A172 cells transfected with pSilencer-siRNA expressing siRNA against the neurotensin receptor showed a down regulation of plasma membrane neurotensin receptor expression (B). No down regulation was observed instead in the control, where in absence of transfection with pSilencer-siRNA neurotensin receptor is expressed predominantly on the plasma membrane and within cytoplasmic vesicles (A).

Example 22

West Nile Virus Attachment Domain

West Nile virus envelope domain III (350-390) was cloned into *E. coli* expression vector pET16b (Novogen, USA) and expressed as His-tagged fusion protein. The DIII protein was expressed as a soluble protein and was purified through a nickel column. The purified DIII protein was separated by 10% SDS PAGE and followed by transferring to nitrocellulose membrane. The recombinant DIII is detected with monoclonal antibodies against E protein of WNV and anti-His antibodies. The monoclonal anti-E protein and anti-His antibodies were used at a concentration of 1:500 and 1:200 respectively. The secondary antibodies conjugated with alkaline phosphatase were added subsequently. Detection of DIII protein was carried out by adding the substrate (nitroblue tetrazolium) to the blot.

Vero cells were first incubated with different concentration (5 to 100 µg/ml) of DIII protein or BSA for 30 min at 37° C. Excess or unbound protein is removed by washing thrice with PBS. Radiolabeled WNV or Dengue virus (250 plaque forming unit, PFU) is added and incubated for 1 h at 37° C. Virus entry into Vero cells was determined by radioactive counts from a scintillation counter.

The production of murine poluyclonal antibodies against West Nile virus DIII protein was carried out as previously described by Chu and Ng, 2003. The pool sera from 6 DIII protein immunized Balb/c mice were diluted in a series of concentration 1:2 to 1:8192. Equal volume (50 µl) of anti-DIII antibodies and WNV (500 PFU) were incubated for 1 h before overlaying onto Vero cells monolayer. Excess or unbound virus-antibody complexes were removed by washing thrice with PBS. Plaques were stained with crystal violet after 4 days of incubation at 37° C. Virus diluent was used as a control for anti-DIII antibodies.

The portion of West Nile Virus coding for the domain III is reported herein as SEQ ID NO: 20. This sequence encodes for domain III of the Envelope protein according to the well known genetic code. A person skilled in the art can easily identify the domain III coding portions inside the sequence as well as the amino acid sequence, as encoded by SEQ ID NO: 21.

The amino acid sequence of domain III coded by the sequence reported as SEQ ID NO: 20 is designated as SEQ ID NO: 21. A soluble form of recombinant domain III from 350 to 390 of the envelope protein of West Nile virus envelope protein (E protein) was doned into *E. coli* expression vector pET16b (Novogen, USA) and expressed as His-tagged fusion protein. The protein had comprised a sequence reported in the sequence listing as SEQ ID NO:20. The DIII protein was able to be expressed as a soluble protein. Recombinant DIII protein was separated by 10% SDS PAGE and followed by transfering to nitrocellulose membrane. The recombinant DIII is detected with monoclonal antibodies against E protein of WNV and anti-His antibodies. The results are shown in FIG. 22.

Figure 22A:
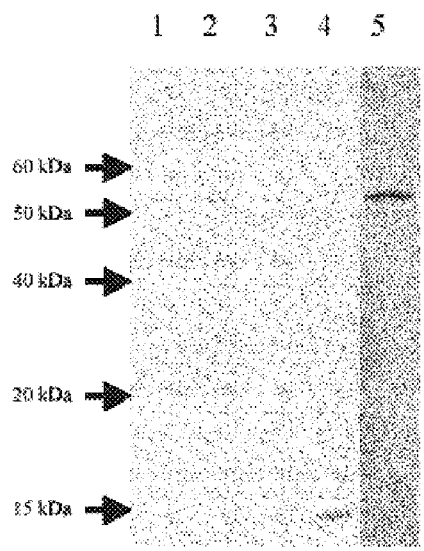
FIG. 22 shows results of a Western Blotting carried out with monoclonal antibodies against (A) E-protein of WNV and (B) anti-His lysate, whole cell lysate where domain II of WNV was cloned and expressed as His-tagged fusion protein. (A) lane 1=IBV nucleocapsid protein; lane 2=Dengue infected whole cells lysate; lane 3=buffer; lane 4=DIII protein; and lane 5=West Nile virus infected whole cell lysate. (B) lane 1=IBV nucleocapsid protein; lane 2=buffer; lane 3=DIII protein; and lane 4=West Nile virus infected whole cell lysate. Molecular size markers are indicated on the left side of the Figure by arrows.
Figure 22B:
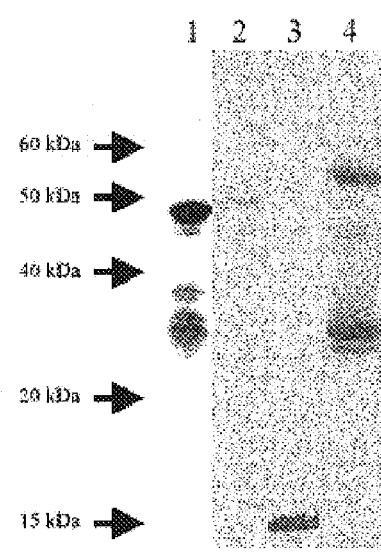

Also polyclonal antibodies (not shown) against West Nile virus E-protein were able to detect the expressed recombinant E domain III (FIG. 22).

Figure 23:
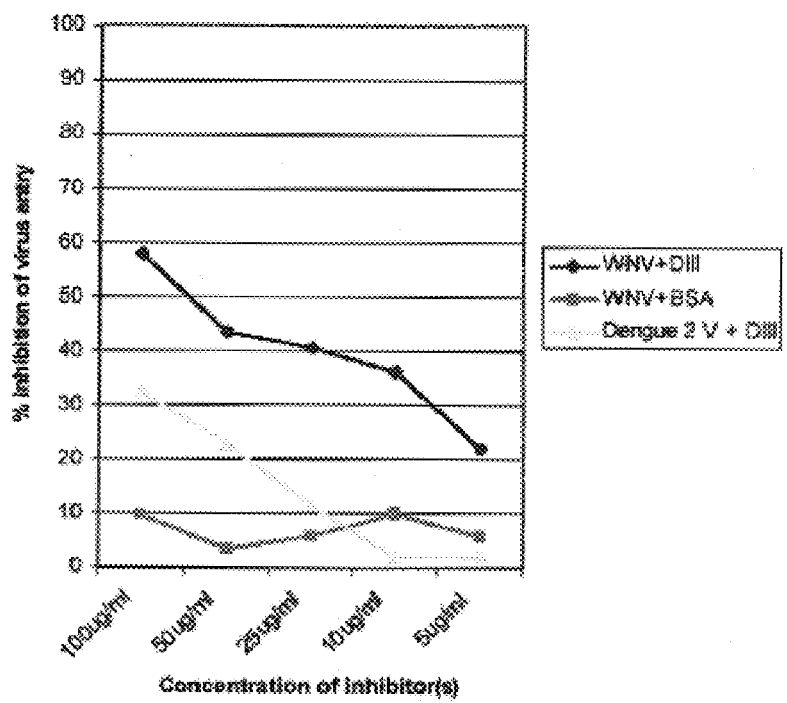
FIG. 23 is a diagram showing results of competitive inhibition of WNV and Dengue virus entry with soluble recombinant WNV envelope DIII. On the x-axis, concentration of inhibitor(s) is reported. On the y-axis, percentage inhibition of virus entry is reported.

Subsequently, Vero cells were first incubated with different concentration of DIII protein or BSA. Radiolabeled WNV or Dengue virus is added and assay for virus entry. Results are shown in FIG. 23. Entry of WNV is significantly blocked in the presence of DIII protein while BSA did not have any effect on the entry of WNV. Recombinant WNV envelope DIII protein can also slightly block the entry of Dengue virus at high concentration used. Therefore, recombinant E domain III was also able to competitively inhibit the binding of West Nile virus in a dosage dependent manner.

Figure 24:
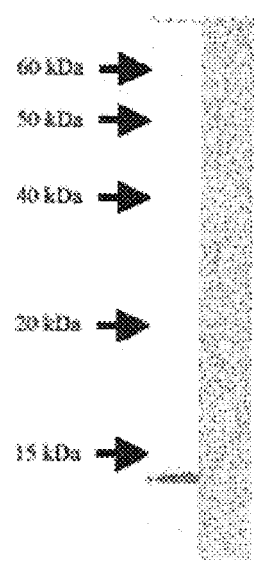
FIG. 24 shows production of murine polyclonal antibodies against recombinant DIII protein. Lane 1=recombinant DIII protein with anti-DIII protein polyclonal murine antibodies; and lane 2=DIII protein with pre-immunized murine sera. Molecular size markers are indicated on the left side of the Figure by arrows.

In addition, murine polyclonal antibodies were produced against the recombinant domain III (FIG. 24). A single 13 KDA protein band (DIII protein) was detected by the murine polyclonal antibodies.

Figure 25:
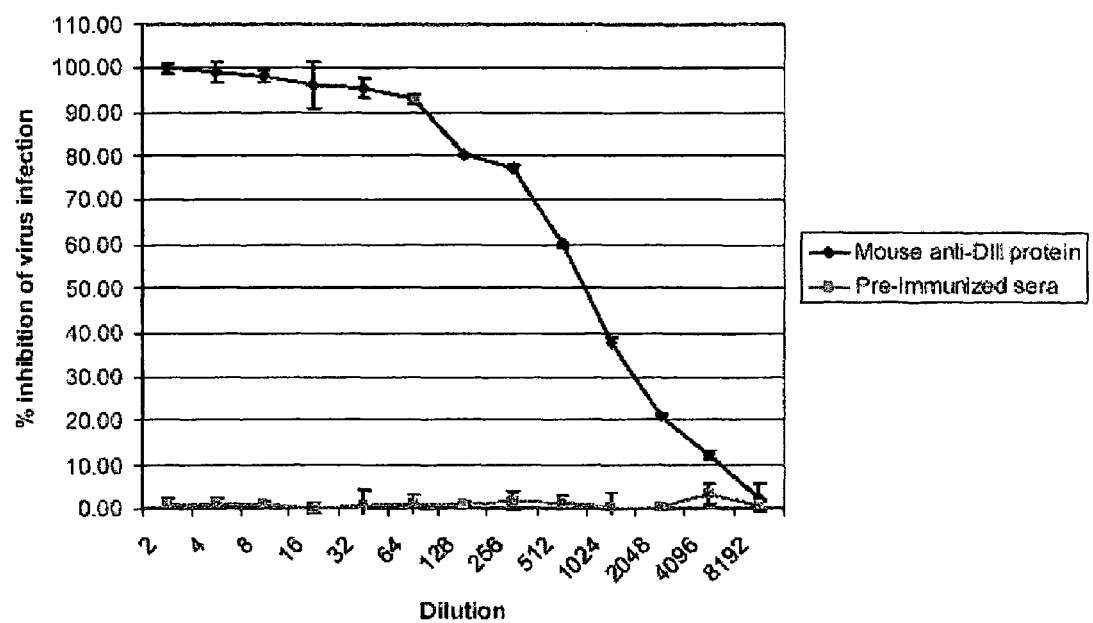
FIG. 25 is a diagram showing results of plaque neutralization of WNV with murine polyclonal antibodies against envelope DIII protein. On the x-axis, various grades of dilution used are reported. On the y-axis, percentage inhibition of virus infection is reported.

These murine polyclonal antibodies were used in plaque neutralization assay of WNV. Recombinant DIII is expressed, purified and injected into 6 Balb/c mice. pool sera were obtained and diluted in a series of concentration as shown in the graph below. Equal volume of anti-DIII antibodies and WNV (500 PFU) were incubated for 1 h before overlaying onto Vero cells monolayer. Plaques were stained with crystal violet. Virus diluent was used as a control for anti-DIII antibodies. Results shown in FIG. 25 demonstrate that murine polyclonal antibodies against DIII protein are capable of neutralizing the West Nile virus Together, these data define that domain III of West Nile virus E protein is responsible for binding to the surface of the cells.

The disclosures of each and every publication and reference cited herein are incorporated herein by reference in their entirety.

The present disclosure has been explained with reference to specific embodiments. Other embodiments will be apparent to those of ordinary skill in the art in view of the foregoing description. The scope of protection of the present disclosure is defined by the appended claims.

REFERENCES

[1] Adlish, J. D., Lahijani, R. S., and St Jeor, S. C. 1990. Identification of a putative cell receptor for human cytomegalovirus. Virology. 176, 3337-3345.

[2] Agnello, V., Abel, G., Elfahal, M., Knight, G. B., and Zhang, Q. X. 1999. Hepatitis C virus and other flaviviridae viruses enter cells via low density lipoprotein receptor. Proc Natl Acad Sci USA. 96, 12766-12771.

[3] Atkinson, P. H., and Summers, D. F. 1971. Purification and properties of HeLa cell plasma membranes. J Biol Chem. 246, 5162-5175.

[4] Beasley D W C., Barrett A D T. 2002. Identification of neutralizing epitopes within structural domain III of the West Nile virus envelop protein. J. Virol. Vol 76, No. 24, 13097-13100.

[5] Bielefeldt-Ohmann, H., Meyer, M., Fitzpatrick, D. R., and Mackenzie, J. S. 2001. Dengue virus binding to human leukocyte cell lines: receptor usage differs between cell types and virus strains. Virus Res. 73, 81-89.

[6] Blau, D. M., and Compans, R. W. 1995. Entry and release of measles virus are polarized in epithelial cells. Virology. 210, 91-99.

[7] Borrow, P., and Oldstone, M. B. 1992. Characterization of lymphocytic choriomeningitis virus-binding protein(s): a candidate cellular receptor for the virus. J Virol. 66, 7270-7281.

[8] Bruett, L., Barber, S. A., and Clements, J. E. 2000. Characterization of a membrane-associated protein implicated in visna virus binding and infection. Virology. 271, 132-141.

[9] Cao, W., Henry, M. D., Borrow, P., Yamada, H., Elder, J. H., Ravkov, E. V., Nichol, S. T., Compans, R. W., Campbell, K. P., and Oldstone, M. B. 1998. Identification of alpha-dystroglycan as a receptor for lymphocytic choriomeningitis virus and Lassa fever virus. Science. 282, 2079-2081.

[10] Castle, E., and Wengler, G. 1987. Nucleotide sequence of the 5'-terminal untranslated part of the genome of the flavivirus West Nile virus. Arch Virol. 92, 309-313.

[11] Castle, E., Leidner, U., Nowak, T., Wengler, G., and Wengler, G. 1986. Primary structure of the West Nile flavivirus genome region coding for all nonstructural proteins. Virology. 149, 10-26.

[12] Castle, E., Nowak, T., Leidner, U., Wengler, G., and Wengler, G. 1985. Sequence analysis of the viral core protein and the membrane-associated proteins V1 and NV2 of the flavivirus West Nile virus and of the genome sequence for these proteins. Virology. 145, 227-236.

[14] Chen, Y., Maguire, T., Hileman, R. E., Fromm, J. R., Esko, J. D., Linhardt, R. J., and Marks, R. M. 1997. Dengue virus infectivity depends on envelope protein binding to target cell heparan sulfate. Nat Med. 3, 866-871.

[15] Choi, A. H., Paul, R. W., and Lee, P. W. 1990. Reovirus binds to multiple plasma membrane proteins of mouse L fibroblasts. Virology. 178, 316-320.

[16] Chu, J. J. H., and Ng, M. L. 2002. Infection of polarized epithelial cells with flavivirus West Nile: Polarized entry and egression of virus occur through apical surface. J Gen Virol. 83, 2427-2435.

[17] Chu, J. J. H., and Ng, M. L. 2002. Trafficking mechanism of West Nile (Sarafend) virus structural proteins. J Med Virol. 67, 127-136.

[18] Chu J J, Ng M L (2003) Characterization of a 105-kDa plasma membrane associated glycoprotein that is involved in West Nile virus binding and infection. Virology. 1;312 (2):458-469.

[19] Cole et al., 1983, Proc. Natl Acad. Sci. USA 80:2026-2030.

[20] Cole et al., 1985, Monoclonal Antibodies And Cancer Therapy, Alen R. Liss, Inc., pp77-96

[21] Crane, S. E., Buzy, J., and Clements, J. E. 1991. Identification of cell membrane proteins that bind visna virus. J Virol. 65, 6137-6143.

[22] Crill, W. D., and Roehrig, J. T. 2001. Monoclonal antibodies that bind to domain III of dengue virus E glycoprotein are the most efficient blockers of virus adsorption to Vero cells. J Virol. 75, 7769-7773.

[23] De Madrid, A. T., and Porterfield, J. S. 1974. The flaviviruses (group B arboviruses): a cross-neutralization study. J Gen Virol. 23, 91-96.

[24] George, S., Gourie-Devi, M., Rao, J. A., Prasad, S. R., and Pavri, K. M. 1984. Isolation of West Nile virus from the brains of children who had died of encephalitis. Bull World Health Organ. 62, 879-882.

[25] Gollins, S. W., and Porterfield, J. S. 1985. Flavivirus infection enhancement in macrophages: an electron microscopic study of viral cellular entry. J Gen Virol. 66, 1969-1982.

[26] Hase, T., Summers, P. L., and Eckels, K. H. 1989a. Flavivirus entry into cultured mosquito cells and human peripheral blood monocytes. Arch Virol. 104, 129-143.

[27] Hase, T., Summers, P. L., Eckels, K. H., and Putnak, J. R. 1989b. Morphogenesis of flaviviruses. Subcell Biochem. 15, 275-305.

[28] Hase, T., Summers, P. L., and Ray, P. 1990. Entry and replication of Japanese encephalitis virus in cultured neurogenic cells. J Virol Methods. 30, 205-214.

[29] Hasegawa, H., Yoshida, M., Shiosaka, T., Fujita, S., and Kobayashi, Y. 1992. Mutations in the envelope protein of Japanese encephalitis virus affect entry into cultured cells and virulence in mice. Virology. 191, 158-165.

[30] Heinz, F. X., Auer, G., Stiasny, K., Holzmann, H., Mandl, C., Guirakhoo, F., and Kunz, C. 1994. The interactions of the flavivirus envelope proteins: implications for virus entry and release. Arch Virol Suppl. 9, 339-348.

[31] Helenius, A. 1995. Alphavirus and flavivirus glycoproteins: structures and functions. Cell. 81, 651-653.

[32] Kimura, T., Kimura-Kuroda, J., Nagashima, K., and Yasui, K. 1999. Analysis of virus-cell binding characteristics on the determination of Japanese encephalitis virus susceptibility. Arch Virol 139, 239-251.

[33] Kohler and Milstein. 1975, Nature 256:495-497; and U.S. Pat. No. 4,376,110)

[34] Kopecky, J., Grubhoffer, L., Kovar, V., Jindrak, L., and Vokurkova, D. A. 1999. A putative host cell receptor for tick-borne encephalitis virus identified by anti-idiotypic antibodies and virus affinoblotting. Intervirology. 42, 9-16.

[35] Kosbor et al., 1983, Immunology Today 4:72;

[36] Liener, I. I., Sharon, N. and Goldstein, I. J. 1986. The Lectins: properties, functions and applications in biology and medicine. Academic Press, London & Florida.

[37] Martinez-Barragan, J. J., and del Angel, R. M. 2001. Identification of a putative coreceptor on Vero cells that participates in dengue 4 virus infection. J Virol. 75, 7818-7827.

[38] Ng, M. L., and Lau, L. C. 1988. Possible involvement of receptors in the entry of Kunjin virus into Vero cells. Arch Virol. 100, 199-211.

[39] Ng, M. L., Tan, S. H. and Chu, J. J. H. 2001. Transport and budding at two distinct sites of visible nucleocpasids of West Nile (Sarafend) virus. J Med Virol. 65, 758-764.

[40] Putnak, J. R., Kanesa-Thasan, N., and Innis, B. L. 1997. A putative cellular receptor for dengue viruses. Nat Med. 3, 828-829.

[41] Ramos-Castaneda, J., Imbert, J. L., Barron, B. L., and Ramos, C. 1997. A 65-kDa trypsin-sensible membrane cell protein as a possible receptor for dengue virus in cultured neuroblastoma cells. J Neurovirol. 3, 435-440.

[42] Rappole, J. H., Derrickson, S. R., and Hubalek, Z. 2000. Migratory birds and spread of West Nile virus in the Western Hemisphere. Emerg Infect Dis. 6, 319-328.

[43] Rey, F. A., Heinz, F. X., Mandl, C., Kunz, C., and Harrison, S. C. 1995. The envelope glycoprotein from tick-borne encephalitis virus at 2 A resolution. Nature. 375, 291-298.

[44] Rice, C. M. 1996. Flaviviridae: the viruses and their replication. In Virology. N. D. Fields, D. M. Knipe, P. M. Kowley, et al., Eds.: 931-959. Lippincott-Raven. Philadelphia, Pa.

[45] Sagara Y, Ishida C, Inoue Y, Shiraki H, Maeda Y. (1998). 71-kilodalton heat shock cognate protein acts as a cellular receptor for syncytium formation induced by human T-cell lymphotropic virus type 1. J Virol.72(1):535-41.

[46] Salas-Benito, J. S., and del Angel, R. M. 1997. Identification of two surface proteins from C6/36 cells that bind dengue type 4 virus. J Virol. 71, 7246-7252.

[47] Sambrook, J., Fritsch, E. F., and Maniatis, T. (ed.). 1989. Molecular Cloning : a laboratory manual, $2^{nd}$ ed. Cold Spring Harbor Laboratory, Cold Spring Harbor, N.Y.

[48] Schneider-Schaulies, J. 2000. Cellular receptors for viruses: links to tropism and pathogenesis. J Gen Virol. 81, 1413-1429.

[49] Se-Thoe, S. Y., Ling, A. E., and Ng, M. L. 2000. Alteration of virus entry mode: a neutralization mechanism for Dengue-2 virus. J Med Virol. 62, 364-376.

[50] Shi W. X., Bunney B. S. 1992. Actions of neurotensin: a review of the electrophysiological studies. Ann NY Acad. Sci. Vol. 668; 1129-145.

[51] Taylor, H. P., and Cooper, N. R. 1990. The human cytomegalovirus receptor on fibroblasts is a 30-kilodalton membrane protein. J Virol. 64, 2484-2490.

[52] Thullier, P., Demangel, C., Bedouelle, H., Megret, F., Jouan, A., Deubel, V., Mazie, J. C., and Lafaye, P. 2001. Mapping of a dengue virus neutralizing epitope critical for the infectivity of all serotypes: insight into the neutralization mechanism. J Gen Virol. 82, 1885-1892.

[53] Tokuyasu, K. T. 1984. Immuno-cryoultramicrotomy. In: Polak J M, Varnell I M, editors. Immunolabelling for electron microscopy. Amsterdam: Elsevier Science. P71-82.

[54] Verdin, E. M., King, G. L., and Maratos-Flier, E. 1989. Characterization of a common high-affinity receptor for reovirus serotypes 1 and 3 on endothelial cells. J Virol. 63, 1318-1325.

[55] Wengler, G., Castle, E., Leidner, U., Nowak, T., and Wengler, G. 1985. Sequence analysis of the membrane protein V3 of the flavivirus West Nile virus and of its gene. Virology. 147, 264-274.

[56] Wengler, G., Wengler, G., and Gross, H. J. 1978. Studies on virus-specific nucleic acids synthesized in vertebrate and mosquito cells infected with flaviviruses. Virology. 89, 423-437.

The invention claimed is:

1. A method for controlling entry of a flavivirus into a cell, the flavivirus exhibiting a flavivirus envelope protein, the flavivirus envelope protein comprising a domain III of the flavivirus envelope protein, the method comprising administering to the cell an agent that functionally interferes with binding of the domain III of the flavivirus envelope protein to a flavivirus receptor protein, wherein the agent comprises a polypeptide having an amino acid sequence that exhibits at least 80% sequence identity to amino acids 350 to 390 of a flavivirus envelope sequence as set forth in SEQ ID NO: 21, and wherein the flavivirus receptor protein is one of an integrin and a neurotensin receptor.

2. The method of claim 1, wherein the domain III comprises a sequence that is substantially homologous to SEQ ID NO: 21.

3. The method of claim 1, wherein the flavivirus is selected from the group consisting of Japanese Encephalitis Virus, West Nile Virus, St. Louis encephalitis virus, Murray Valley encephalitis virus, Dengue virus and Kunjin virus.

4. The method of claim 1, wherein the flavivirus receptor protein is an integrin.

5. The method of claim 4, wherein in the integrin comprises at least one subunit selected from the group consisting of integrin subunit αV, integrin subunit β3 and integrin subunit β5.

6. The method of claim 1, wherein the flavivirus receptor protein is a neurotensin receptor.

7. The method of claim 1, wherein the agent is a ligand of the flavivirus receptor protein.

8. The method of claim 7, wherein the ligand competes with the flavivirus envelope protein domain III for the binding of the domain III of the flavivirus envelope protein to the flavivirus receptor protein.

9. The method of claim 1, wherein the agent comprises a polypeptide having an amino acid sequence that exhibits at least 85% sequence identity to amino acids 350 to 390 of a flavivirus envelope sequence as set forth in SEQ ID NO: 21.

10. The method of claim 1, wherein the agent comprises a polypeptide having an amino acid sequence that exhibits at least 90% sequence identity to amino acids 350 to 390 of a flavivirus envelope sequence as set forth in SEQ ID NO: 21.

11. The method of claim 1, wherein the agent comprises a polypeptide having an amino acid sequence that exhibits at least 95% sequence identity to amino acids 350 to 390 of a flavivirus envelope sequence as set forth in SEQ ID NO: 21.

12. The method of claim 1, wherein the agent comprises a polypeptide having an amino acid sequence that exhibits at least 98% sequence identity to amino acids 350 to 390 of a flavivirus envelope sequence as set forth in SEQ ID NO: 21.

13. The method of claim 1, wherein the agent comprises a polypeptide having an amino acid sequence that exhibits complete identity to amino acids 350 to 390 of a flavivirus envelope sequence as set forth in SEQ ID NO: 21.

* * * * *